US009090923B2

(12) United States Patent
Watanabe et al.

(10) Patent No.: US 9,090,923 B2
(45) Date of Patent: *Jul. 28, 2015

(54) BRANCHED ALPHA-GLUCAN, ALPHA-GLUCOSYLTRANSFERASE WHICH FORMS THE GLUCAN, THEIR PREPARATION AND USES

(71) Applicant: Hayashibara Co., Ltd, Okayama-shi (JP)

(72) Inventors: Hikaru Watanabe, Okayama (JP); Takuo Yamamoto, Okayama (JP); Tomoyuki Nishimoto, Okayama (JP); Keji Tsusaki, Okayama (JP); Kazuyuki Oku, Okayama (JP); Hiroto Chaen, Okayama (JP); Shigeharu Fukuda, Okayama (JP)

(73) Assignee: HAYASHIBARA CO., LTD., Okayama-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/160,749

(22) Filed: Jan. 22, 2014

(65) Prior Publication Data

US 2014/0134676 A1  May 15, 2014

Related U.S. Application Data

(62) Division of application No. 13/666,220, filed on Nov. 1, 2012, now Pat. No. 8,673,608, which is a division of application No. 12/597,660, filed as application No. PCT/JP2008/057879 on Apr. 23, 2008, now Pat. No. 8,324,375.

(30) Foreign Application Priority Data

Apr. 26, 2007   (JP) ................. 2007-117369

(51) Int. Cl.
| | | |
|---|---|---|
| *C12P 19/18* | (2006.01) |
| *A21D 2/18* | (2006.01) |
| *A23C 9/13* | (2006.01) |
| *A23C 9/154* | (2006.01) |
| *A23L 1/09* | (2006.01) |
| *A23L 1/19* | (2006.01) |
| *A23L 1/20* | (2006.01) |
| *A23L 1/305* | (2006.01) |
| *A23L 2/39* | (2006.01) |
| *A61K 8/73* | (2006.01) |
| *A61K 31/716* | (2006.01) |
| *A61Q 19/00* | (2006.01) |
| *C08B 37/00* | (2006.01) |
| *C12N 9/10* | (2006.01) |
| *C12P 19/04* | (2006.01) |
| *C12R 1/06* | (2006.01) |
| *C12R 1/09* | (2006.01) |

(52) U.S. Cl.
CPC . *C12P 19/18* (2013.01); *A21D 2/18* (2013.01); *A23C 9/1307* (2013.01); *A23C 9/1544* (2013.01); *A23L 1/095* (2013.01); *A23L 1/19* (2013.01); *A23L 1/2005* (2013.01); *A23L 1/3053* (2013.01); *A23L 2/39* (2013.01); *A61K 8/73* (2013.01); *A61K 31/716* (2013.01); *A61Q 19/00* (2013.01); *C08B 37/0009* (2013.01); *C12N 9/1051* (2013.01); *C12P 19/04* (2013.01); *C12R 1/06* (2013.01); *C12R 1/09* (2013.01); *A23V 2002/00* (2013.01)

(58) Field of Classification Search
None
See application file for complete search history.

(56) References Cited

U.S. PATENT DOCUMENTS

| 4,521,252 A | 6/1985 | Miyake et al. |
| 5,455,168 A | 10/1995 | Maruta et al. |

FOREIGN PATENT DOCUMENTS

| GB | 2106912 A | 4/1983 |
| JP | 58072598 A | 4/1983 |
| JP | 7143876 A | 6/1995 |
| JP | 2001011101 A | 1/2001 |
| WO | 2006054474 A1 | 5/2006 |

OTHER PUBLICATIONS

Shokuhin-To-Kaihatsu, "Market trend of dietary fiber," food processing and ingredients, 1999, pp. 24-27, vol. 34, No. 2.

(Continued)

*Primary Examiner* — Ruth Davis
*Assistant Examiner* — Emily Cordas
(74) *Attorney, Agent, or Firm* — Browdy and Neimark, PLLC

(57) ABSTRACT

The present invention has objects to provide a glucan useful as water-soluble dietary fiber, its preparation and uses. The present invention solves the above objects by providing a branched α-glucan, which is constructed by glucose molecules and characterized by methylation analysis as follows:

(1) Ratio of 2,3,6-trimethyl-1,4,5-triacetyl-glucitol to 2,3,4-trimethyl-1,5,6-triacetyl-glucitol is in the range of 1:0.6 to 1:4;

(2) Total content of 2,3,6-trimethyl-1,4,5-triacetyl-glucitol and 2,3,4-trimethyl-1,5,6-triacetyl-glucitolis 60% or higher in the partially methylated glucitol acetates;

(3) Content of 2,4,6-trimethyl-1,3,5-triacetyl-glucitol is 0.5% or higher but less than 10% in the partially methylated glucitol acetates; and (4) Content of 2,4-dimethyl-1,3,5,6-tetraacetyl-glucitol is 0.5% or higher in the partially methylated glucitol acetates; a novel α-glucosyltransferase which forms the branched α-glucan, processes for producing them, and their uses.

5 Claims, 10 Drawing Sheets

(56) References Cited

OTHER PUBLICATIONS

Shoten, "Low-molecular weight water-soluble dietary fiber," series of food ingredients sciences of dietary fibers, 1997, pp. 116-131.

Yamamoto et al., "Purification and some properties of dextrin dextranase from acetobacter capsulatus ATCC 11894," Bioscience, biotechnology, and biochemistry, 1992, pp. 169-173, vol. 56, No. 2.

Suzuki et al., "Functional characteristics of a bacterial dextrin dextranase from acetobacter capsulatum ATCC 11894," journal of applied glycoscience, 2001, pp. 143-151, vol. 48, No. 2.

"Methods for analyzing nutritional components (appendix 1-3 of nutrition labeling standard) in nutrition labeling standard," notification No. 146 of ministry of health, labour, and welfare, 1996, pp. 19-27.

Holt et al., "Bergey's manual of systematic bacteriology," 1986, vol. 2, Williams & Wilkins.

Ribosomal database project: release 10, "RDP release 10, update 15:: Oct. 5, 2009:: 1,104,383 16S rRNAs," URL: http://rdp.cme.msu.edu/index.jsp.

"Handbook of amylases and related enzymes: Their sources, isolation methods, properties and applications," the amylase research society of Japan, 1988, Pergamon press Inc., Tokyo, Japan.

Ooshima et al., "Non-cariogenicity of the disaccharide palatinose in experimental dental caries of rats," Infection and immunity, 1983, pp. 43-49, vol. 39, No. 1.

Okada et al., "Digestion and fermentation of pullulan," Journal of Japanese Society of Nutrition and Food Sciences, 1990, pp. 23-29, vol. 43, No. 1.

Reeves et al., "AIN-93 purified diets for laboratory rodents: Final report of the American institute of nutrition ad hoc writing committee on the reformulation of the AIN-76A rodent diet," Journal of nutrition, 1993, pp. 1939-1951, vol. 123.

Watanabe et al., "A novel glucanotransferase that produces a cyclomaltopentaose cyclized by an alpha-1, 6-Linkage," J. Appl. Glycosci., 2007, pp. 109-118, vol. 54.

Kralj, et al "Molecular Characterization of a Novel Glucosyltransferase from *Lactobacillus reuteri* Strain 121 Synthesizing a Unique, Highly Branched Glucan with alpha-(1-->4) and alpha-(1-->6) Glucosidic Bonds," Applied and Evironmental Microbiology, 68(9): 4283-4291 (Sep. 1, 2002).

Tsusaki, et al "Structure of a novel highly branched alpha-glucan enzymatically produced from maltodextrin," Carbohydrate Research, 334(16): 2151-2156 (Nov. 2, 2009).

Shokuhin-To-Kaihatsu "Market Trend I—Market Report: Dietary Fiber," Food Processing and Ingredients, 34(2): 24-27 (1999).

Jiang et al., Acta Pharmaceutica Sinica 2005, 40(4):347-350.

WO2006054474 A1 (WIPO machine translation of description).

WO2006054474 A1 (WIPO machine translation of claims).

BRANCHED ALPHA-GLUCAN, ALPHA-GLUCOSYLTRANSFERASE WHICH FORMS THE GLUCAN, THEIR PREPARATION AND USES

TECHNICAL FIELD

The present invention relates to a branched α-glucan, an α-glucosyltransferase which forms the branched α-glucan, their preparation and uses. More particularly, the present invention relates to a branched α-glucan, which is constructed by glucose molecules and characterized by methylation analysis as follows:

(1) Ratio of 2,3,6-trimethyl-1,4,5-triacetyl-glucitol to 2,3,4-trimethyl-1,5,6-triacetyl-glucitol is in the range of 1:0.6 to 1:4;

(2) Total content of 2,3,6-trimethyl-1,4,5-triacetyl-glucitol and 2,3,4-trimethyl-1,5,6-triacetyl-glucitol is 60% or higher in the partially methylated glucitol acetates;

(3) Content of 2,4,6-trimethyl-1,3,5-triacetyl-glucitol is 0.5% or higher but less than 10% in the partially methylated glucitol acetates; and (4) Content of 2,4-dimethyl-1,3,5,6-tetraacetyl-glucitol is 0.5% or higher in the partially methylated glucitol acetates; an α-glucosyltransferase which forms the above branched α-glucan by transferring α-glucose residue when allowed to act on maltose and/or α-1,4 glucan having a glucose polymerization degree of 3 or higher; their preparation; a composition comprising the branched α-glucan; and its uses.

BACKGROUND ART

The term, "dietary fiber", inherently means cell components of plants, which is hardly digestible by animals, such as cellulose, lignin, hemicellulose, pectin, etc., however, in the broad sense, it includes low-digestible water-soluble polysaccharides which are not digested by amylases. Such water-soluble polysaccharides are called as "water-soluble dietary fiber" (hereinafter, simply abbreviated as "WSDF", in this specification). Recently, dietary fiber attracts attention to its functions as prebiotics improving bacterial flora in the intestine in addition to its inherent functions of regulating the functions of the intestine, lowering blood-cholesterol level, and controlling blood-sugar level. However, it is generally recognized that dietary fiber and calcium are nutritional elements which are insufficiently taken in Japanese dietary life. It has been pointed out that, in the present-day, the average intake of WSDF in Japanese is only 50 to 80% of the objective intake, 20 to 25 g/day, recommended in "Nutritional Requirement in Japanese", 5th edition (1994) (Ref. "Market Trend of Dietary Fiber", *Shokuhin-To-Kaihatsu* (Food processing and ingredients), Vol. 34, No. 2, pp. 0.24-27 (1999) (in Japanese)). Under these circumstances, various low-digestible polysaccharides, which can be used as materials for various foods and beverages and useful as WSDF, have been proposed.

For example, polysaccharides present in nature or their modified products, such as low-digestible starch (moist heat treated high-amylose corn starch), guar gum hydrolyzate, glucomannnan, and low-molecular weight alginate are commercially available as WSDFs. However, since they have relatively high viscosities and defects of deteriorating relish and texture when they are incorporated into foods and beverages, their uses are restricted to a narrow range. While, "POLYDEXTROSE®" (developed by Pfizer Inc., USA) and low-digestible dextrins are widely utilized in the field of foods and beverages as WSDF with low-viscosity. "POLYDEXTROSE®" is a synthetic polysaccharide obtained by the steps of heating glucose, sorbitol, and citric acid under a high-vacuum condition; and polymerizing them by the chemical reaction. It is known that "POLYDEXTROSE®" has complicated branched structures of binding glucoses via 1,3-, 1,4-, 1,6-, 1,2,6-, and 1,4,6-glucosidic linkages. On the other hand, the low-digestible dextrin is a synthetic polysaccharide whose digestibility is lowered by inducing 1,2-, 1,3-, 1,2,4-, and 1,3,4-glucosidic linkages, not inherently present in starch, formed by transglucosylation and reverse-reaction during the chemical hydrolysis of starch. The low-digestible dextrin is produced by the steps of adding a small amount of hydrochloric acid to starch, heating the mixture in a powdery form to obtain roasted dextrin, dissolving the resulting roasted dextrin into water, hydrolyzing the roasted dextrin by admixing with α-amylase, purifying the resulting solution with a low viscosity, concentrating the solution, and drying the dextrin with a spray-dryer. As a low-digestible dextrin, another product, produced by the steps of allowing glucoamylase to act on the above low-digestible dextrin to hydrolyze the digestible part into glucose, removing the resulting glucose, purifying, and drying the dextrin with spray-dryer to further lowering digestibility, has been commercialized. However, since the low-digestible dextrin can not be obtained in a high yield from material starch and it causes color-deterioration easily, these characteristics are problems on the industrial production of the low-digestible dextrin. It is reported that the newly induced glucosidic linkages in "POLYDEXTROSE®" and the low-digestible dextrin include both α- and β-anomer forms and the reducing end glucose of those are partially converted into 1,6-anhydro-glucose (Ref. "Low-molecular weight water-soluble dietary fiber", part of a series of *Science of Dietary Fibers*, pp. 116-131, published by Asakura Shoten (1997)).

Among the glucosidic linkages (hereinafter, "glucosidic linkage" is simply abbreviated as "linkage" in this specification) which are a mode of binding glucose in glucan, α-1,6 linkage is less hydrolysable by amylase than α-1,4 linkage. Therefore, it is expected that glucan rich in α-1,6 linkages can be used as WSDF. For example, dextran, produced from sucrose as material by the action of dextransucrase (EC 2.4.1.5) from *Leuconostoc mesenteroides* belonging to lactic acid bacteria, is a glucan in which glucoses are polymerized by mainly α-1,6 linkages, and may have branches by α-1, 2 and α-1,3 linkages. In the case of using dextransucrase from *Leuconostoc mesenteroides* B-512F, the resulting dextran has α-1,6 linkages in the ratio of 90% or higher in the linkages of the dextran, and is expected to be a low-digestible glucan. However, dextran can not be obtained in a high yield from sucrose, requires complicated purifying procedure because of its high viscosity, and drives up the cost. Therefore, dextran has not been tried to be used as WSDF.

There has been proposed a method for preparing WSDF by allowing amylase to act on inexpensive starch to hydrolyze α-1,4 linkage for relatively increasing the content of α-1,6 linkages. Japanese Patent Kokai No. 11,101/2001 disclosed a method for preparing a branched dextrin in which the ratio of α-1,6 linkage to α-1,4 linkage is increased to 10 to 20% by the steps of allowing α-amylase and β-amylase to act on liquefied starch and collecting the residual dextrin. However, the yield of the branched dextrin from material starch is relatively low and the lowering of the digestibility can not be expected because the branched dextrin is produced by a method of increasing the ratio of α-1,6 linkage while keeping the inherent branches (α-1,6 linkages) in starch and removing glucose chain in which glucoses are polymerized via α-1,4 linkages. While, dextrin dextranase (EC 2.1.1.2) has been well known as an enzyme which acts on partial starch hydrolyzate (dextrin) and induces α-1,6 linkages in its molecule (Ref. Kazuya Yamamoto et al., *Bioscience, Biotechnology, and Biochemistry*, Vol. 56, pp. 169-173 (1992)). Dextrin dextranase is an enzyme which acts on partial starch hydrolyzate and forms dextran having a structure of polymerizing glucoses via α-1,6 linkages by catalyzing mainly α-1,6 glucosyl-transferring reaction. However, there are problems in the well-known dextrin dextranase from *Acetobacter capsulatum* belonging to acetic acid bacteria that the ratio of α-1,6 linkage inducible in the molecule is relatively low (Ref. Masayuki Suzuki et al. Journal of Applied Glycoscience, Vol. 48, No. 2, pp. 143-151 (2001)), and the enzyme is unstable. Therefore, the enzyme has not been used practically. Under these circumstances, a novel low-digestible glucan and a process for producing the same have been strongly desired for increasing options of WSDF.

DISCLOSURE OF INVENTION

The objects of the present invention are to provide a glucan useful as WSDF, its preparation and uses.

To solve the above objects, the present inventors have extensively screened microorganisms capable of producing an enzyme which forms a branched α-glucan having a relatively large number of branch by using, as substrates, maltose and/or α-1,4 glucan having a glucose polymerization degree of 3 or higher. (in this specification, "branch" means glucosidic linkage other than α-1,4 linkage in the glucan.) As a result, the present inventors isolated microorganisms, PP710 and PP349, from soil samples and found that the microorganisms extracellulary produce a novel α-glucosyltransferase which forms a branched α-glucan having α-1,4, α-1,6, α-1,3, α-1,4,6, and α-1,3,6 linkages in its structure when allowed to act on maltose and/or α-1,4 glucan having a glucose polymerization degree of 3 or higher. Further, the present inventors found that the novel enzyme efficiently produces the branched α-glucan from α-glucan such as partial starch hydrolyzate and the branched α-glucan which is constructed by glucose molecules and characterized by methylation analysis as follows:

(1) Ratio of 2,3,6-trimethyl-1,4,5-triacetyl-glucitol to 2,3,4-trimethyl-1,5,6-triacetyl-glucitol is in the range of 1:0.6 to 1:4;

(2) Total content of 2,3,6-trimethyl-1,4,5-triacetyl-glucitol and 2,3,4-trimethyl-1,5,6-triacetyl-glucitolis 60% or higher in the partially methylated glucitol acetates;

(3) Content of 2,4,6-trimethyl-1,3,5-triacetyl-glucitol is 0.5% or higher but less than 10% in the partially methylated glucitol acetates; and (4) Content of 2,4-dimethyl-1,3,5,6-tetraacetyl-glucitol is 0.5% or higher in the partially methylated glucitol acetates.

Also, the present inventors found that a starch-degrading amylase is present in the crude preparation of the α-glucosyltransferase, obtained by culturing PP710, as a concomitant enzyme. It was found that a branched α-glucan with a relatively higher WSDF content can be produced by using the crude enzyme preparation, or the purified amylase and α-glucosyltransferase in combination, in comparison with the case of using α-glucosyltransferase only. Further, it was found that the weight-average molecular weight and the WSDF content of the branched α-glucan can be controlled by using the α-glucosyltransferase together with well-known amylases and starch-debranching enzymes as a substituent of the amylase. In addition, the present inventors found that the branched α-glucan, obtainable by the above methods, shows a relatively higher ratio of α-1,6 linkage than the material α-1,4 glucan; a significantly low-digestibility which is useful as WSDF; and effects of inhibiting the elevation of blood-sugar level and lowering lipids in living bodies. Based on the above knowledge, the present inventors accomplished the present invention.

The present invention solves the above objects by providing a branched α-glucan which is constructed by glucose molecules and characterized by methylation analysis as follows:

(1) Ratio of 2,3,6-trimethyl-1,4,5-triacetyl-glucitol to 2,3,4-trimethyl-1,5,6-triacetyl-glucitol is in the range of 1:0.6 to 1:4;

(2) Total content of 2,3,6-trimethyl-1,4,5-triacetyl-glucitol and 2,3,4-trimethyl-1,5,6-triacetyl-glucitol is 60% or higher in the partially methylated glucitol acetates;

(3) Content of 2,4,6-trimethyl-1,3,5-triacetyl-glucitol is 0.5% or higher but less than 10% in the partially methylated glucitol acetates; and (4) Content of 2,4-dimethyl-1,3,5,6-tetraacetyl-glucitol is 0.5% or higher in the partially methylated glucitol acetates; a novel α-glucosyltransferase which forms the branched α-glucan; their preparation and uses.

According to the present invention, a branched α-glucan, having white color, low digestibility, and usefulness as WSDF, can be produced in a high yield, large amount, and low cost, and provided to various fields including foods and beverages.

EXPLANATION OF SYMBOLS

Figure 13:
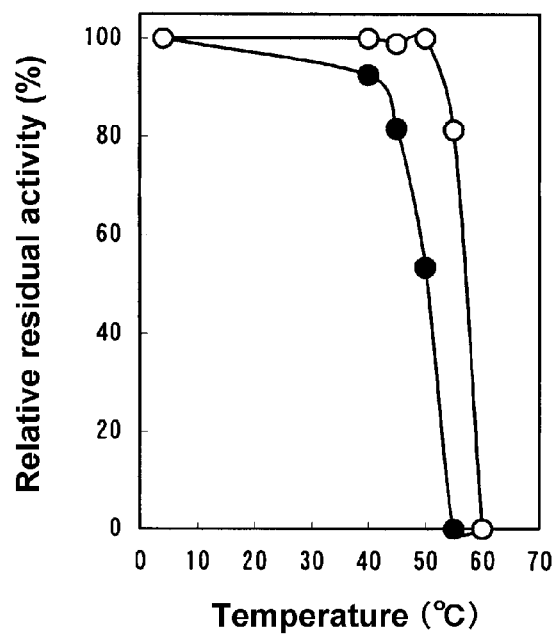
FIG. 13 shows the thermal stability of amylase from *Bacillus circulans* PP710.

In FIG. 1 and FIGS. 15 to 19,
  A: Eluting position corresponding to the molecular weight of 1000,000 daltons
  B: Eluting position corresponding to the molecular weight of 100,000 daltons
  C: Eluting position corresponding to the molecular weight of 10,000 daltons
  D: Eluting position corresponding to the molecular weight of 1,000 daltons
  E: Eluting position corresponding to the molecular weight of 100 daltons
In FIG. 1,
  a: Gel-filtration HPLC chromatogram of partial starch hydrolyzate used as substrate
  b: Gel-filtration HPLC chromatogram of Glucan A
  c: Gel-filtration HPLC chromatogram of Glucan B
  1: Position corresponding to the glucose polymerization degree of 499
  2: Position corresponding to the glucose polymerization degree of 6.3
  3: Position corresponding to the glucose polymerization degree of 384
  4: Position corresponding to the glucose polymerization degree of 22.2
  5: Position corresponding to the glucose polymerization degree of 10.9
  6: Position corresponding to the glucose polymerization degree of 1
  7: Position corresponding to the glucose polymerization degree of 433
  8: Position corresponding to the glucose polymerization degree of 22.8
  9: Position corresponding to the glucose polymerization degree of 10.9
  10: Position corresponding to the glucose polymerization degree of 1
In FIG. 2,
  1: Reference diagram of partial starch hydrolyzate
  2: Reference diagram of the branched α-glucan of the present invention
  a: Non-reducing end glucose residue
  b: Glucose residue involving α-1,3 linkage
  c: Glucose residue involving α-1,4 linkage
  d: Glucose residue involving α-1,6 linkage
  e: Glucose residue involving α-1,3,6 linkage
  f: Glucose residue involving α-1,4,6 linkage
  Diagonal broken line: α-1,3 linkage
  Horizontal solid line: α-1,4 linkage
  Vertical solid line: α-1,6 linkage
In FIG. 13,
  •: In the absence of $Ca^{2+}$ ion
  ○: In the presence of 1 mM $Ca^{2+}$ ion
In FIG. 15,
  a: Gel-filtration HPLC chromatogram of partial starch hydrolyzate used as substrate
  b: Gel-filtration HPLC chromatogram of the branched α-glucan prepared by using 10 units/g-substrate of α-glucosyltransferase and 0.1 unit/g-substrate of amylase
  c: Gel-filtration HPLC chromatogram of the branched α-glucan prepared by using 10 units/g-substrate of α-glucosyltransferase and 0.2 unit/g-substrate of amylase
  d: Gel-filtration HPLC chromatogram of the branched α-glucan prepared by using 10 units/g-substrate of α-glucosyltransferase and 0.5 unit/g-substrate of amylase
  e: Gel-filtration HPLC chromatogram of the branched α-glucan prepared by using 10 units/g-substrate of α-glucosyltransferase and 1 unit/g-substrate of amylase
In FIG. 16,
  a: Gel-filtration HPLC chromatogram of partial starch hydrolyzate used as substrate
  b: Gel-filtration HPLC chromatogram of the branched α-glucan prepared by using 10 units/g-substrate of α-glucosyltransferase and 50 units/g-substrate of isoamylase
  c: Gel-filtration HPLC chromatogram of the branched α-glucan prepared by using 10 units/g-substrate of α-glucosyltransferase and 200 units/g-substrate of isoamylase
  d: Gel-filtration HPLC chromatogram of the branched α-glucan prepared by using 10 units/g-substrate of α-glucosyltransferase and 500 units/g-substrate of isoamylase
  e: Gel-filtration HPLC chromatogram of the branched α-glucan prepared by using 10 units/g-substrate of α-glucosyltransferase and 1,000 units/g-substrate of isoamylase
In FIG. 17,
  a: Gel-filtration HPLC chromatogram of partial starch hydrolyzate used as substrate
  b: Gel-filtration HPLC chromatogram of the branched α-glucan prepared by using 10 units/g-substrate of α-glucosyltransferase and 0.1 unit/g-substrate of α-amylase
  c: Gel-filtration HPLC chromatogram of the branched α-glucan prepared by using 10 units/g-substrate of α-glucosyltransferase and 0.2 unit/g-substrate of α-amylase
  d: Gel-filtration HPLC chromatogram of the branched α-glucan prepared by using 10 units/g-substrate of α-glucosyltransferase and 0.5 unit/g-substrate of α-amylase
  e: Gel-filtration HPLC chromatogram of the branched α-glucan prepared by using 10 units/g-substrate of α-glucosyltransferase and 1.0 unit/g-substrate of α-amylase In FIG. 18,
- a: Gel-filtration HPLC chromatogram of partial starch hydrolyzate used as substrate
- b: Gel-filtration HPLC chromatogram of the branched α-glucan prepared by using 10 units/g-substrate of α-glucosyltransferase and 0.1 unit/g-substrate of CGTase
- c: Gel-filtration HPLC chromatogram of the branched α-glucan prepared by using 10 units/g-substrate of α-glucosyltransferase and 0.2 unit/g-substrate of CGTase
- d: Gel-filtration HPLC chromatogram of the branched α-glucan prepared by using 10 units/g-substrate of α-glucosyltransferase and 0.5 unit/g-substrate of CGTase
- e: Gel-filtration HPLC chromatogram of the branched α-glucan prepared by using 10 units/g-substrate of α-glucosyltransferase and 1.0 unit/g-substrate of CGTase In FIG. 19,
- a: Gel-filtration HPLC chromatogram of partial starch hydrolyzate used as substrate
- b: Gel-filtration HPLC chromatogram of the branched α-glucan prepared by using 10 units/g-substrate of α-glucosyltransferase, 50 units/g-substrate of isoamylase, and 1 unit/g-substrate of CGTase
- c: Gel-filtration HPLC chromatogram of the branched α-glucan prepared by using 10 units/g-substrate of α-glucosyltransferase, 200 units/g-substrate of isoamylase, and 1 unit/g-substrate of CGTase
- d: Gel-filtration HPLC chromatogram of the branched α-glucan prepared by using 10 units/g-substrate of α-glucosyltransferase, 500 units/g-substrate of isoamylase, and 1 unit/g-substrate of CGTase
- e: Gel-filtration HPLC chromatogram of the branched α-glucan prepared by using 10 units/g-substrate of α-glucosyltransferase, 1,000 units/g-substrate of isoamylase, and 1 unit/g-substrate of CGTase

BEST MODE FOR CARRYING OUT THE INVENTION

The term, "glucan", as referred to as in the present invention means an oligosaccharide or polysaccharide, with a glucose polymerization degree of 3 or higher, which is constructed by glucose molecules. The branched α-glucan of the present invention is an α-glucan constructed by glucose molecules and shows the following characteristics by the methylation analysis:

(1) Ratio of 2,3,6-trimethyl-1,4,5-triacetyl-glucitol to 2,3,4-trimethyl-1,5,6-triacetyl-glucitol is in the range of 1:0.6 to 1:4;

(2) Total content of 2,3,6-trimethyl-1,4,5-triacetyl-glucitol and 2,3,4-trimethyl-1,5,6-triacetyl-glucitolis 60% or higher in the partially methylated glucitol acetates;

(3) Content of 2,4,6-trimethyl-1,3,5-triacetyl-glucitol is 0.5% or higher but less than 10% in the partially methylated glucitol acetates; and (4) Content of 2,4-dimethyl-1,3,5,6-tetraacetyl-glucitol is 0.5% or higher in the partially methylated glucitol acetates.

The term, "methylation analysis", as referred to as in the present invention means a generally well-known method for determining the linkages of monosaccharide as the component in poly- or oligo-saccharides. Analysis of glucosidic linkages in a glucan by the methylation analysis is carried out by the following steps of:

methylating all the free hydroxyl groups of glucose residues which constitute the glucan;
hydrolyzing the completely methylated glucan;
reducing the resulting methylated glucoses for eliminating the anomers to make into methylated glucitols;
acetylating the free hydroxyl groups of the methylated glucitols to make into the partially methylated glucitol acetates (hereinafter, "partially methylated glucitol acetate" may be abbreviated as "partially methylated product" by abbreviating acetylated positions and "glucitol acetate" in this specification); and analyzing the resulting partially methylated products by a gas chromatography.

Various partially methylated products, derived from glucose residues respectively different in the glucosidic linkage in the glucan, can be represented by the percentage (%) of peak area per the total peak area of all the partially methylated products in the gas chromatogram. Then, from the peak area (%), the ratio of the glucose residue different in the linkage, i.e., the ratio of each glucosidic linkage can be determined. In this specification, "ratio" of the partially methylated products is defined as the ratio of peak area in the gas chromatogram obtained by the methylation analysis. Also, "%" of the partially methylated products is defined as "peak area %" in the gas chromatogram obtained by the methylation analysis.

2,3,6-Trimethyl-1,4,5-triacetyl-glucitol (hereinafter, abbreviated as "2,3,6-trimethylated product"), in the above (1), means the glucose residues whose C-4 position is involved in 1,4 linkage, and 2,3,4-trimethyl-1,5,6-triacetyl-glucitol (hereinafter, abbreviated as "2,3,4-trimethylated product") means the glucose residues whose C-6 position is involved in 1,6 linkage. Also, "ratio of 2,3,6-trimethylated product to 2,3,4-trimethylated product is in the range of 1:0.6 to 1:4" means that, in the gas chromatogram of the partially methylated glucitol actates in the methylation analysis, the ratio of glucose residues whose C-6 and C-1 positions involve the linkage to the total content of glucose residues whose C-4 and C-1 positions involve the linkage and glucose residues whose C-6 and C-1 positions involve the linkage is in the range of 37.5 to 80.0%.

"Total content of 2,3,6-trimethylated product and 2,3,4-trimethylated product is 60% or higher in the partially methylated products", in the above (2), means that, in the branched α-glucan of the present invention, the total content of glucose residues whose C-4 and C-1 positions involve the linkage and glucose residues whose C-6 and C-1 positions involve the linkage is 60% or higher in all glucose residues constituting the glucan.

In the same manner, "2,4,6-trimethyl-1,3,5-triacetyl-glucitol" (hereinafter, abbreviated as "2,4,6-trimethylated product"), in the above (3), means glucose residues whose C-3 position involves 1,3 linkage. Also, "content of 2,4,6-trimethylated product is 0.5% or higher but less than 10% in the partially methylated products" means that, in the branched α-glucan of the present invention, the content of glucose residues whose C-3 and C-1 positions involve the linkage is 0.5% or higher but less than 10% in all glucose residues constituting the glucan.

Similarly, "2,4-dimethyl-1,3,5,6-tetraacetyl-glucitol" (hereinafter, abbreviated as "2,4-demethylated product"), in the above (4), means glucose residues whose C-3 and C-6 positions respectively involve 1,3 and 1,6 linkages. Also, "content of 2,4-demethylated product is 0.5% or higher in the partially methylated products" means that, in the branched α-glucan of the present invention, the content of glucose residues whose C-3, C-6, and C-1 positions involve the linkage is 0.5% or higher in all glucose residues constituting the glucan.

The branched α-glucan of the present invention, which fulfills the above characteristics (1) to (4), is a novel glucan hitherto unknown. The order of linking glucose residues in the branched α-glucan of the present invention is not specifically restricted as far as it fulfills the above characteristics (1) to (4) by methylation analysis.

Usually, the branched α-glucan of the present invention is in the form of a mixture of branched α-glucans having various glucose polymerization degrees of 10 or higher. The value of dividing the weight-average molecular weight (Mw) with the number average molecular weight (Mn), Mw/Mn, of the branched α-glucan of the present invention is, usually, less than 20.

The branched α-glucan of the present invention is characterized in that isomaltose is formed, usually, in an amount of 25% (w/w) or higher but less than 50% (w/w), on a dry solid basis of the hydrolyzate, when isomaltodextranase (EC 3.2.1.94), which is an enzyme capable of hydrolyzing α-1,2, α-1,3, α-1,4, and α-1,6 linkages as far as the linkage is adjuscent to reducing end side of isomaltose structure in a glucan, is allowed to act on the branched α-glucan of the present invention.

The branched α-glucan of the present invention is characterized in that the WSDF content is, usually, 40% (w/w) or higher when WSDF is quantified according to the method described in Section 8, Dietary fiber, (2) High-performance liquid chromatography (Enzyme-HPLC method), "Methods for analyzing nutritional components (Appendix 1-3 of Nutrition Labeling Standard) in Nutrition Labeling Standard (Notification No. 146 of Ministry of Health, Labour, and Welfare, May, 1986)". The outline of the above high-performance liquid chromatography method (hereinafter, abbreviated as "Enzyme-HPLC method") is as follows: A sample is hydrolyzed by a series of enzyme-treatments using a thermostable α-amylase, protease, and amyloglucosidase (glucoamylase). Then, proteins, organic acids, and inorganic salts are removed from the resulting enzyme-treated mixture using ion-exchange resins to make into a sample solution for high-performance liquid chromatography (HPLC). Successively, the sample solution is subjected to gel-filtration HPLC for measuring peak areas of undigested glucan and glucose in the HPLC chromatogram. Then, the WSDF content of the sample is calculated based on the peak areas and the amount of glucose in the sample solution, separately determined by conventional glucose oxidase-peroxidase method. The Enzyme-HPLC method is also explained in detail in Experiments described later.

As shown in Experiment 9 described later, the branched α-glucan of the present invention is hardly digested by salivary α-amylase, pancreas α-amylase, and small intestinal α-glucosidase when orally ingested. Accordingly, the branched α-glucan of the present invention can be used as a low-calorie WSDF with a low-digestibility, which does not stimulate the rapid elevation of blood-sugar level and the secretion of insulin. In addition, the branched α-glucan has characteristics of not inducing acid fermentation by microorganisms in the mouth and inhibiting the formation of insoluble glucans which is a cause of dental plaque when used together with sucrose. Therefore, the branched α-glucan of the present invention can be advantageously used as a low- or anti-cariogenic saccharide. Further, the branched α-glucan of the present invention shows no toxicity in the acute-toxity test using mice.

As shown in Experiments 20 and 21 described later, since the branched α-glucan of the present invention inhibits the elevation of blood-sugar level and insulin level when it is ingested together with an amylaseous substance, in comparison with the case of ingesting an amylaceous substance only, it can be used as an agent for inhibiting the elevation of blood-sugar level.

As shown in Experiment 22 described later, since the branched α-glucan of the present invention inhibits the excess accumulation of lipids in living bodies, it can be used as an agent for lowering lipids in living bodies.

In the cases of using the branched α-glucan as the above agent for inhibiting the elevation of blood-sugar level or that for lowering lipids in living bodies, the branched α-glucan with a relatively high WSDF content is preferable to exercise the effects. Therefore, the WSDF content of the branched α-glucan is preferable to be, usually, 40% (w/w) or higher, desirably, 50% (w/w) or higher, more desirably, 60% (w/w) or higher.

"α-Glucosyltransferase" as referred to as in the present invention means any enzyme which acts on maltose and/or α-1,4 glucan having a glucose polymerization degree of 3 or higher as substrate and forming the branched α-glucan of the present invention by catalyzing the glucosyl-transfer without substantial hydrolytic action. The α-glucosyltransferase of the present invention is different from well-known α-glucosidase from fungi and dextrin-dextranase from the genus *Acetobacter* in the characteristics of showing weak hydrolytic activity and efficient transferring activity under low to high substrate concentration without depending on the substrate concentration, and of forming α-1,3 and α-1,3,6 linkages.

The enzyme activity of the α-glucosyltransferase of the present invention can be assayed as follows: A substrate solution is prepared by dissolving maltose in 20 mM acetate buffer (pH 6.0) to give a final concentration of 1% (w/v). 0.5 ml of an enzyme solution is added to 5 ml of the substrate solution, and the mixture solution is incubated at 40° C. for 30 min. After the reaction, 0.5 ml of the reaction mixture is admixed with 5 ml of 20 mM phosphate buffer (pH 7.0) and boiled for 10 min to stop the reaction. Successively, the amount of glucose in the solution is measured by the glucose oxidase-peroxidase method according to the conventional method, and the amount of glucose formed in the reaction mixture is calculated. One unit of the α-glucosyltransferase activity is defined as the amount of enzyme which forms one μmole of glucose per minute under the above conditions.

As a concrete example of the α-glucosyltransferase of the present invention, the enzyme having the following physicochemical properties can be listed.

(1) Molecular weight 90,000±10,000 daltons when determined on SDS-polyacrylamide gel electrophoresis;

(2) Optimum temperature 50 to 55° C. when reacted at pH 6.0 for 30 min;

(3) Optimum pH pH 5.0 to 6.3 when reacted at 40° C. for 30 min;

(4) Thermal stability

Stable up to 40° C. when incubated at pH 6.0 for 60 min; and (5) pH Stability

Stable in the pH range of 3.5 to 8.4 when incubated at 4° C. for 24 hours;

As another concrete example of the α-glucosyltransferase of the present invention, the enzyme having the following physicochemical properties can be listed.

(1) Molecular weight 90,000±10,000 daltons when determined on SDS-polyacrylamide gel electrophoresis;

(2) Optimum temperature

About 50° C. when reacted at pH 6.0 for 30 min;

(3) Optimum pH

About pH 6.0 when reacted at 40° C. for 30 min;

(4) Thermal stability

Stable up to 40° C. when incubated at pH 6.0 for 60 min; and (5) pH Stability

Stable in the pH range of 4.0 to 8.0 when incubated at 4° C. for 24 hours;

Although the α-glucosyltransferase of the present invention is not restricted by its source, microorganisms are preferable as the source. Particularly, microorganisms, PP710 and PP349, isolated from soil by the present inventors can be preferably used as the source. The following Tables 1 and 2 are the identification results of the strains PP710 and PP349, capable of producing the α-glucosyltransferase. The identification of the strains was carried out according to the method as described in "*BISEIBUTSU-NO-BUNRUI-TO-DOTEI*" (Classification and Identification of Microorganisms), edited by Takeji Hasegawa, published by Japan Scientific Societies Press, Tokyo, Japan (1985).

TABLE 1

| <A: Morphology> | |
|---|---|
| Characteristic of cells when incubated at 27° C. in nutrient agar | Existing usually in a rod shape of 0.5 × 1.0 to 2.0 × 6.0 μm, Possessing no motility, Forming spores, Gram stain; positive, |
| <B: Cultural property> Characteristics of colony formed when incubated at 27° C. in nutrient agar plate | |
| Shape | Circular colony having a diameter of 1 to 2 mm after 2 days incubation |
| Rim | Entire |
| Projection | Semi-lenticular |
| Gloss | Dull |
| Surface | Smooth |
| Color | Translucence, Gray |
| Characteristics of colony formed when incubated at 27° C. in nutrient agar slant | |
| Growth | Medium |
| Shape | Thread-like |
| Characteristics of colony formed when incubated at 27° C. in nutrient gelatin stab culture | Not liquefied |
| <C: Physiological properties> | |
| VP-test | Negative |
| Indole formation | Negative |
| Dihydroxylacetone formation | Negative |
| Hydrolysis of starch | Positive |
| Pigment formation | Not forming soluble pigments |
| Urease | Negative |
| Oxidase | Negative |
| Catalase | Positive |
| Growing range | pH: 5.5 to 10.0, temperature: 15 to 37° C. |
| Formation of acids from D-glucose | Positive |
| Formation of gases from D-glucose | Negative |
| Utilization of citric acid | Positive |
| Decomposition of tyrosine | Negative |
| Deamination of phenylalanine | Negative |
| Reduction of nitrate | Positive |
| Oxygen requirements | Aerobic |

TABLE 1-continued

| Growth in the presence of lysozyme | Positive |
|---|---|
| Mol % of guanine (G) plus cytosine (C) of DNA | 53.4% |

TABLE 2

| <A: Morphology> | |
|---|---|
| Characteristic of cells when incubated at 27° C. in nutrient agar | Existing usually in a coccus or rod shape of 0.4 × 1.0 to 0.6 × 3.0 μm, Exhibiting polymorphism showing rod-coccus cycle (early phase: rod-shape, late phase: short rod- or coccus-shape), Possessing no motility, Forming spores, Gram stain; positive, |
| <B: Cultural property> Characteristics of colony formed when incubated at 27° C. in nutrient agar plate | |
| Shape | Circular colony having a diameter of 1 to 2 mm after 2 days incubation |
| Rim | Entire |
| Projection | Semi-lenticular |
| Gloss | Moist gloss |
| Surface | Smooth |
| Color | Translucence, Maize |
| Characteristics of colony formed when incubated at 27° C. in nutrient agar slant | |
| Growth | Medium |
| Shape | Homogenous |
| Characteristics of colony formed when incubated at 27° C. in nutrient gelatin stab culture | Not liquefied |
| <C: Physiological properties> | |
| Oxygen requirements | Aerobic |
| Major diamino acid in cell wall | Lysine |
| Peptideglycan | Lysine, Alanine |
| N-Acyl type of cell wall | Acetyl |
| Major sugar components constructing cell wall | D-Galactose, D-Glucose |
| Catalase | Positive |
| Extracellular DNase | Positive |
| Hydrolysis of starch | Positive |
| Vitamin requirement | Negative |
| Homology of 16S rRNA with that of *Arthrobacter globiformis* type culture (DSM20124) | 97% |

The above bacteriological properties of strains PP710 and PP349 were compared with those of known microorganisms with reference to "Bergey's Manual of Systematic Bacteriology, Vol. 2 (1986)" and "Ribosomal Database (URL:http://rdp.cme.msu.edu/index.jsp). As a result, it was revealed that the strains PP710 and PP349 were respectively identified as *Bacillus circulans* and *Arthrobacter globifomis*. Based on these results, the present inventors named the two strains to "*Bacillus circulans* PP710" and "*Arthrobacter globiformis* PP349", and deposited them on Feb. 1, 2006, in International Patent Organism, National Institute of Advanced Industrial Science and Technology, AIST Tsukuba Central 6, 1-1, Higashi 1-Chome Tsukuba-shi, Ibaraki-ken Japan, and accepted under the accession numbers of FERM BP-10771 and FERM BP-10770, respectively. The microorganisms capable of producing the α-glucosyltransferase of the present invention include the above strains and their mutants capable of producing the enzyme in large amount, which are obtainable by inducing mutation to the above strains and screening the enzyme-hyper-producing mutants.

Any nutrient culture medium can be used for cultivating any microorganism capable of producing the α-glucosyltransferase of the present invention as long as it can grow therein and produce the α-glucosyltransferase: For example, synthetic- and natural-culture media can be used as nutrient culture media. Any carbon source can be used as long as it is utilized by the microorganisms: Examples of such carbon source are saccharides such as starch and phytoglycogen, obtainable from plants; glycogen and pullulan, obtainable from animals and microorganisms; hydrolyzates thereof, glucose, fructose, lactose, sucrose, mannitol, sorbitol, and saccharide syrups; and organic acids such as citric acid and succinic acid. The concentrations of these carbon sources in nutrient culture media are appropriately chosen. The nitrogen sources usable in the present invention are, for example, inorganic nitrogen compounds such as ammonium salts and nitrates; organic nitrogen compounds such as urea, corn steep liquor, casein, peptone, yeast extract and beef extract. The inorganic ingredients usable in the invention are, for example, calcium salts, magnesium salts, potassium salts, sodium salts, phosphates, manganese salts, zinc salts, iron salts, copper salts, molybdenium salts, and cobalt salts. If necessary, amino acids and vitamins can be suitably used.

The microorganisms capable of producing the α-glucosyltransferase of the present invention are cultured under aerobic conditions, usually, at a temperature in the range of 15 to 37° C. and at a pH in the range of 5.5 to 10, preferably, at a temperature in the range of 20 to 34° C. and at a pH in the range of 5.5 to 8.5. The cultivation time is set to a time longer than that required for the growth of the microorganisms, preferably, 10 to 150 hours. The concentration of dissolved oxygen is not specifically restricted, but usually, 0.5 to 20 ppm. The concentration of dissolved oxygen can be kept within the above range by controlling aeration and agitation. The cultivation can be carried out batch-wise or in a continuous manner.

After culturing the microorganisms capable of producing the α-glucosyltransferase according to the method described above, the culture containing the enzyme of the present invention is recovered. The major activity of the α-glucosyltransferase is found in the cell-free supernatant in both cases of *Bacillus circulans* PP710, FERM BP-10771, and *Arthrobacter globiformis* PP349, FERM BP-10770. Both the cell-free supernatant and the culture broth can be used as a crude enzyme preparation. Conventional liquid-solid separation methods can be employed to remove cells from the culture. For example, methods to directly centrifuge the resultant culture, as well as those to filtrate the culture with pre-coated filters or to separate cells by membrane filtration using plane filters or follow fibers, can be suitably used. While cell-free supernatants thus obtained can be used intact as a crude enzyme solution, they can be concentrated prior to use. The concentration methods usable in the invention are, for example, salting out using ammonium sulfate, sedimentation using acetone or alcohol, and concentration using membranes such as plane filters and follow fibers.

The α-glucosyltransferase can be subjected to the conventional immobilization using cell-free supernatants and their concentrates. Examples of such conventional methods are conjugation methods using ion exchangers, covalent bindings and adsorptions using resins and membranes, and inclusion methods using high molecular weight substances.

As described above, a crude enzyme solution can be used intact after concentrating it as the α-glucosyltransferase of the present invention. If necessary, the enzyme can be advantageously used after separating or purifying the crude enzyme solution by suitable conventional methods used in the art, for example, salting out, ion-exchange chromatography, hydrophobic chromatography, gel-filtration chromatography, affinity chromatography, preparative electrophoresis, etc.

α-1,4 Glucan having a glucose polymerization degree of 3 or higher, which can be used as a substrate for the α-glucosyltransferase of the present invention, includes starch, amylose, amylopectin, glycogen, and their partial hydrolyzates such as amylodextrins, maltodextrins, maltooligosaccharides, obtainable by partially hydrolyzing them with amylases and acids. The partial hydrolyzates obtainable by hydrolyzing starch, amylose, amylopectin, and glycogen by using amylase such as α-amylase (EC 3.2.1.1), β-amylase (EC 3.2.1.2), maltotetraose-forming amylase (EC 3.2.1.60), maltopentaose-forming amylase, maltohexaose-forming amylase (EC 3.2.1.98), cyclomaltodextrin glucanotransferase (EC 2.4.1.19, hereinafter abbreviated as "CGTase" in this specification), etc., described in "*Handbook of Amylases and Related Enzymes*" published by Pergamon Press Inc., (Tokyo), 1988; can be used as the partial hydrolyzates. Further, starch-debranching enzymes such as pullulanase (EC 3.2.1 41) and isoamylase (EC 3.2.1.68) can be arbitrarily used for preparing the partial hydrolyzates. Both subcelestal starches such as those from corn, wheat, rice, etc., and subterranean starches such as those from potato, sweet potato, tapioca, etc., can be used as amylaceous substrates. The substrate can be preferably used in the form of a solution prepared by gelatinizing and/or liquefying the above starch. Further, chemically modified starch, obtained by chemically modifying a part of starch, such as etherified starch (hydroxypropyl-starch, carboxymethyl-starch, acetyl-starch, etc.), esterified starch (phosphorylated starch, octernylsuccinate ester of starch, etc.), cross-linked starch (starch cross-linked by acetyladipate, starch cross-linked by phosphate, starch cross-linked by hydroxypropylphosphate, etc.), etc, can be used as a substrate of the α-glucosyltransferase of the present invention.

When the α-glucosyltransferase of the present invention is allowed to act on a substrate, the substrate concentration is not specifically restricted. For example, the reaction by the α-glucosyltransferase of the present invention proceeds to form the branched α-glucan even in the case of using a substrate solution with a relatively low concentration such as 0.5% (w/v). For industrial production, the substrate concentration is preferable to be, usually, 1% (w/v) or higher, preferably, 5 to 60% (w/v), more preferably, 10 to 50% (w/v); and the branched α-glucan of the present invention can be advantageously produced under the condition. The reaction temperature used in the present enzymatic reaction can be set to a temperature at which the reaction proceeds, i.e., a temperature up to about 60° C., preferably, a temperature in the range of 30 to 50° C. The reaction pH is controlled in the range of, usually, 4 to 8, preferably, 5 to 7. Since the amount of enzyme and the reaction time are closely related, the conditions are adequately chosen with respect to the progress of the objective enzymatic reaction.

The mechanism of forming the branched α-glucan, when the α-glucosyltransferase of the present invention is allowed to act on an aqueous solution of starch, partial starch hydrolyzate, or amylose, is estimated as follows:

(1) The enzyme acts on maltose and/or α-1,4 glucan having a glucose polymerization degree of 3 or higher as the substrate and forms the α-1,4 glucan in which a glucose residue is bound via α-linkage to hydroxyl group at C-4 or C-6 position of the non-reducing end glucose residue (α-glucan whose glucose polymerization degree is increased by one) and the α-1,4 glucan whose glucose polymerization degree is decreased by one, by mainly transferring the non-reducing end glucose residue to the non-reducing end glucose residue of the other α-1,4 glucan by α-1,4 or α-1,6 transglucosylation.

(2) The enzyme further acts on the α-1,4 glucan whose glucose polymerization degree is decreased by one, formed in the above step (1); and transfers a glucose residue to the C-4 or C-6 hydroxyl group of the non-reducing end glucose residue of the α-glucan whose glucose polymerization degree is increased by one, also formed in the above step (1), by the intermolecular α-1,4 or α-1,6 transglucosylation to elongate the glucose chain.

(3) By repeating the reactions in the above steps (1) and (2), the enzyme forms a glucan having both α-1,4 and α-1,6 linkages from maltose and/or α-glucan having a glucose polymerization degree of 3 or higher.

(4) Although the frequency is low, the enzyme forms a glucan having α-1,3, α-1,4,6, and α-1,3,6 linkages in addition to α-1,4 and α-1,6 linkages by catalyzing the α-1,3 transglucosylation and α-1,4 or α-1,3 transglucosylation to the internal glucose residues involving α-1,6 linkages, in the glucan.

(5) As results of repeating the reactions in the above steps (1) to (4), the branched α-glucan of the present invention, in which glucose is mainly bound via α-1,4 and α-1,6 linkages and which has α-1,3, α-1,4,6, and α-1,3,6 linkages in a low frequency, is formed by the enzyme.

It was revealed that *Bacillus circulans* PP710, FERM. BP-10771, capable of producing the α-glucosyltransferase of the present invention, also produces an amylase together with the α-glucosyltransferase of the present invention simultaneously. It was also revealed that the branched α-glucan with a high WSDF content can be unexpectedly produced when the α-glucosyltransferase and the amylase were allowed to act on maltose and/or α-1,4 glucan having a glucose polymerization degree of 3 or higher in combination, in comparison with the case of using the α-glucosyltransferase only.

As an example of such amylase produced by *Bacillus criculans* PP710, FERM BP-10771, the enzyme having the following physicochemical properties can be used:

(1) Action
Catalyzing the hydrolysis of starch and the transfer of glycosyl group, forming cyclodextrins, and hydrolyzing pullulan to form panose;
(2) Molecular weight
58,000±10,000 daltons when determined on SDS-polyacrylamide gel electrophoresis;
(3) Optimum temperature
55° C. when reacted at pH 6.0 for 30 min;
(4) Optimum pH
pH 6 to 7 when reacted at 35° C. for 30 min;
(5) Thermal stability
Stable up to 40° C. when incubated at pH 6.0 for 60 min;
Stable up to 50° C. when incubated at pH 6.0 in the presence of 1 mM $Ca^{2+}$ ion; and
(6) pH Stability
Stable in the pH range of 6.0 to 8.0 when incubated at 4° C. for 24 hours;

The reason why the WSDF content of the branched α-glucan, obtained from partial starch hydrolyzate by using the α-glucosyltransferase and the amylase in combination, is higher than that of the branched α-glucan, obtained by using the α-glucosyltransferase only, is suggested that the amylase further transfers glycosyl groups to the branched α-glucan formed by the α-glucosyltransferase and the degree of the branch in the glucan is increased.

When the branched α-glucan is prepared by the enzyme reaction, the molecular weight distribution of the branched α-glucan can be advantageously controlled by using a well-known amylase in combination with the α-glucosyltransferase. Also, the digestibility or the reducing powder of the branched α-glucan can be advantageously decreased by the combinational use of the enzymes. For example, the branched α-glucan with a narrow molecular weight distribution, low viscosity, and high content of α-1,3, α-1,6, and α-1,3,6 linkages, which involve the low digestibility, can be advantageously prepared by allowing an enzyme, which hydrolyzes internal α-1,4 linkages of starch to newly form non-reducing end glucose residues, such as α-amylase and CGTase to act on liquefied starch in combination with the α-glucosyltransferase of the present invention. Also, a starch-debranching enzyme such as isomalyase can be used together with the α-glucosyltransferase for narrowing the range of molecular weight distribution and lowering the viscosity. A non-reducing saccharide-forming enzyme (alias "maltooligosyltrehalose synthase", (EC 5.4.99.15), disclosed in Japanese Patent Kokai No. 143,876/95, can be used together with the α-glucosyltransferase for lowering the reducing power of the branched α-glucan by partially converting reducing end parts into trehalose structure.

In addition, the branched α-glucan of the present invention can be produced by the steps of culturing a microorganism capable of producing the α-glucosyltransferase of the present invention in a culture medium comprising maltose and/or α-1,4 glucan having a glucose polymerization degree of 3 or higher and collecting the formed branched α-glucan from the culture broth.

The reaction mixture, thus obtained by the above reaction, can be used intact as a branched α-glucan product. Optionally, the branched α-glucan having low digestibility can be prepared by the steps of hydrolyzing the digestive parts in the glucan by allowing one or more enzymes selected from the group consisting of α-amylase, β-amylase, glucoamylase, and α-glucosidase to act on the reaction mixture, collecting the resulting non-digestive fraction by separating methods, and eliminating the resulting hydrolyzates such as glucose by a fermenting treatment using yeast. Usually, the reaction mixture comprising the branched α-glucan is used after purification. Conventional methods used for purifying saccharides can be arbitrarily selected as the purification method. For example, one or more purification methods selected from the group consisting of decoloring with an activated charcoal; desalting with ion exchange resins in H- and OH-form; separation using organic solvents such as alcohol and acetone; and separation using a membrane having a suitable separability; can be arbitrarily used.

The α-glucosyltransferase of the present invention hardly produces low molecular weight oligosaccharides such as glucose and maltose when allowed to act on gelatinized starch or partial starch hydrolyzate with a relatively low DE (Dextrose Equivalent), preferably, DE less than 20. Therefore, it is not necessary to purify the reaction product by column chromatography. However, the reaction product can be arbitrary purified for any purpose. When ion-exchange chromatography is used for purifying the branched α-glucan, column chromatography using a strongly acidic cation exchange resin, described in Japanese Patent Kokai Nos. 23,799/83 and 72, 598/83, can be advantageously used. In this case, any one of fixed bed, moving bed, and semi-moving bed methods can be employed.

The solution containing the branched α-glucan of the present invention thus obtained can be used intact. However, it is preferable to make the branched α-glucan into powdery form by drying for preservation and handling. Usually, various methods such as freeze-drying, spray-drying, and drum drying can be used for drying. Optionally, the dried branched α-glucan can be arbitrary made into powder with a specific particle size by pulverizing, sieving, and granulating.

The branched α-glucan of the present invention exhibits various properties such as osmotic pressure-controlling property, excipient property, gloss-imparting property, moisture-retaining property, viscosity-imparting property, adhesion property, crystallization-inhibiting property for other saccharides, low fermentative property, etc. Thus, the branched α-glucan of the present invention and the saccharide compositions comprising the same can be advantageously used as WSDF, quality-improving agent, stabilizer, excipient, etc., for various compositions such as foods and beverages, favorite products, feeds, baits, cosmetics, and pharmaceuticals.

The branched α-glucan of the present invention can be used in combination with other sweeteners, for example, powdery syrup, glucose, fructose, isomerized sugar, sucrose, maltose, trehalose, honey, maple sugar, sorbitol, maltitol, dihydrochalcone, stevioside, α-glycosyl stevioside, sweetener of Momordica grosvenori, glycyrrhizin, thaumatin, sucralose, L-aspartyl L-phenylalanine methyl ester, saccharine, glycine and alanine; and fillers such as dextrin, starch, dextran, and lactose.

Further, powdery products of the branched α-glucan of the present invention can be arbitrarily used intact or, if necessary, after mixing with fillers, excipients, binders, etc., and then shaped into various shapes such as granules, spheres, sticks, plates, cubes, etc.

Since the branched α-glucan of the present invention is hardly digestible when it is ingested orally, it can be advantageously used as WSDF for general food products. For example, it can be advantageously used as a quality-improving agent for various seasonings such as a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, the branched α-glucan can be advantageously used to as WSDF, which can be incorporate into various "wagashi" (Japanese cakes) such as "senbei" (a rice cracker), "arare" (a rice cake cube), "okoshi" (a millet and rice cake), "gyuhi" (a starch paste), "mochi" (a rise paste) and the like, "manju" (a bun with a bean-jam), "uiro" (a sweet rice jelly), "an" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, and fruit paste; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of urchin), "ika-no-shiokara" (salted guts of squid), "su-konbu" (processed tangle), "saki-surume" (dried squid strips), "fugu-no-mirin-boshi" (a dried mirin-seasoned swellfish), seasoned fish flour such as of Pacific cod, sea bream, shrimp, etc.; "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, sake, fruit liquor, low-malt beer and beer; soft drinks such as a coffee, cocoa, juice, carbonated beverage, sour milk beverage, and beverage containing a lactic acid bacterium; instant food products such as instant pudding mix, instant hot cake mix, instant juice, instant coffee, "sokuseki-shiruko" (an instant mix of azuki-bean soup with rice cake), and instant soup mix; and other foods and beverages such as solid foods for babies, foods for therapy, drinks, peptide foods, and frozen foods.

The branched α-glucan can be arbitrarily used as feeds and pet foods for improving the functions of the intestine, improving constipation, inhibiting obesity of animals and pets such as domestic animals, poultry, honeybees, silk warms, and fishes. Also, the branched α-glucan can be advantageously used as a quality-improving agent and stabilizer for various compositions including favorite products, cosmetics, and pharmaceuticals in a paste or liquid form such as tobacco, cigarette, tooth paste, lipstick, rouge, lip cream, internal liquid medicine, tablet, troche, cod-liver oil in the form of drop, oral refrigerant, cachou, and gargle.

When used as a quality-improving agent or stabilizer, the branched α-glucan can be advantageously used in biologically active substances susceptible to lose their effective ingredients and activities, as well as in health foods, functional foods, and pharmaceuticals containing the biologically active substances. Example of such biologically active substances are liquid preparations containing lymphokines such as α-, β-, and γ-interferons, tumor necrosis factor-α (TNF-α), tumor necrosis factor-β (TNF-β), macropharge migration inhibitory factor, colony-stimulating factor, transfer factor, and interleukin 2; liquid preparations containing hormones such as insulin, growth hormone, prolactin, erythropoietin, and follicle-stimulating hormone; liquid biological preparations such as BCG vaccine, Japanese encephalitis vaccine, measles vaccine, live polio vaccine, small pox vaccine, tetanus toxoid, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamin, riboflavin, L-ascorbic acid, cod liver oil, carotenoid, ergosterol, tocopherol; highly unsaturated fatty acids and their derivatives such as EPA, DHA and arachidonic acid; solution of enzymes such as lipase, esterase, urokinase, protease, β-amylase, isoamylase, glucanase, and lactase; extracts such as ginseng extract, turtle extract, chlorella extract, aloe extract and propolis extract; biologically active substances such as living microorganisms paste of virus, lactic acid bacteria, and yeast, and royal jelly. By using the branched α-glucan of the present invention as a quality-improving agent or stablizer, the above biologically active substances can be arbitrary prepared in health foods, functional foods, and pharmaceuticals in a liquid, paste, or solid form, which have a satisfactorily-high stability and quality with less fear of losing or inactivating their effective ingredients and activities.

The methods for incorporating the branched α-glucan of the present invention into the aforesaid compositions are those which can incorporate it before completion of their processing, and which can be appropriately selected from the following conventional methods; mixing, kneading, dissolving, melting, soaking, penetrating, dispersing, applying, coating, spraying, injecting, crystallizing, and solidifying. The amount of the branched α-glucan to be preferably incorporated into the final compositions is usually in an amount of 0.1% or higher, desirably, 1% or higher.

Further, since the α-glucosyltransferase of the present invention converts α-1,4 glucan into the branched α-glucan of the present invention when the enzyme is allowed to act on a composition comprising maltose and/or α-1,4 glucan having a glucose polymerization degree of 3 or higher, the enzyme can be used as a quality-improving agent for the composition comprising maltose and/or α-1,4 glucan having a glucose polymerization degree of 3 or higher.

Furthermore, the α-glucosyltransferase of the present invention converts maltose and/or α-1,4 glucan having a glucose polymerization degree of 3 or higher into the branched α-glucan of the present invention, and while 25% (w/w) or higher but 50% (w/w) or lower, on a dry substrate basis, of isomaltose is formed by hydrolyzing the branched α-glucan of the present invention by using isomaltodextranase (EC 3.2.1.94). Accordingly, isomaltose or a saccharide composition comprising the same can be produced from maltose and/or α-1,4 glucan having a glucose polymerization degree of 3 or higher as material by the two-step enzyme reactions using the α-glucosyltransferase of the present invention and isomaltodextranase.

The following experiments explain the present invention in detail.

Experiment 1

Preparation of a glucan using α-glucosyltransferase from *Bacillus circulans* PP710 (FERM BP-10771)

Experiment 1-1

Preparation of α-glucosyltransferase from *Bacillus circulans* PP710 (FERM BP-10771)

A liquid culture medium consisting of 1.5% (w/v) of "PINEDEX® #4", a partial starch hydrolyzate commercialized by Matsutani Chemical Industries Co., Ltd., Hyogo, Japan, 0.5% (w/v) of "POLYPEPTONE®", a yeast extract commercialized by Nihon Pharmaceutical Co., Ltd., Tokyo, Japan, 0.1% (w/v) of "YEAST EXTRACT S", a yeast extract commercialized by Nihon Pharmaceutical Co., Ltd., Tokyo, Japan, 0.1% (w/v) of dipotassium phosphate, 0.06% (w/v) of sodium phosphate dihydrate, 0.05% (w/v) of magnesium sulfate hepta-hydrate, 0.001% (w/v) of manganese sulfate penta-hydrate, 0.001%(w/v) of ferrous sulfate hepta-hydrate, and water was placed in a 500 ml-Erlenmeyer flask in an amount of 100 ml, sterilized by autoclaving at 121° C. for 20 min, and cooled. Successively, the culture medium was inoculated with *Bacillus circulans* PP710, FERM BP-10771, and followed by cultivation under rotary-shaking conditions at 27° C. and 230 rpm for 48 hours to obtain a seed culture.

A fresh preparation of the same culture medium was placed in twelve 500 ml-Erlenmeyer flasks in respective amounts of 100 ml, sterilized by heating and cooled to 27° C. Successively, one milliliter each of the above seed culture was inoculated to the medium and followed by cultivation under rotary-shaking conditions at 27° C. for 24 hours. After completion of the culture, the culture broth was withdrawn from each of the Erlenmeyer flasks and centrifuged at 8,000 rpm for 20 minutes to remove cells. The α-glucosyltransferase activity of the resulting culture supernatant was assayed and determined to be 2.8 units/ml. About one liter of the culture supernatant was salted out by adding ammonium sulfate to give finally 80% saturation and allowing it to stand at 4° C. for 24 hours. The resultant precipitates were collected by centrifuging at 11,000 rpm for 30 min, dissolved in 20 mM acetate buffer (pH 4.5), and dialyzed against a fresh preparation of the same buffer to obtain about 20 ml of a crude enzyme solution. The crude enzyme solution was subjected to cation-exchange column chromatography using 20 ml of "CM-TOYOPEARL™ 650S" gel, a cation-exchange gel commercialized by Tosoh Corporation, Tokyo, Japan, pre-equilibrated with 20 mM acetate buffer (pH 4.5). After eluting non-absorbed proteins, the active fractions were eluted by a linear gradient of 0 to 0.5 M sodium chloride. The active fractions, eluted at about 0.18 to 0.45 M sodium chloride, were collected and dialyzed against 20 mM acetate buffer (pH 6.0). The resulting dialyzate was used as a preparation of α-glucosyltransferase.

Experiment 1-2

Preparation of a branched α-glucan using α-glucosyltransferase

One hundred milliliter of the preparation of α-glucosyltransferase, obtained in Experiment 1-1, was used as an enzyme solution. "PINEDEX® #100", a partial starch hydrolyzate commercialized by Matsutani Chemical Industries Co., Ltd., Hyogo, Japan, was admixed with the enzyme solution to give a final concentration of 30% (w/v), followed by the enzyme reaction at 40° C. for 72 hours, and then heated at about 100° C. for 10 minutes to stop the reaction. After removing the resultant insoluble substances by filtration, the filtrate was decolored and desalted using "DIAION™ SK-1B" and "DIAION™ WA30", ion exchange resins commercialized by Mitsubishi Chemical Corporation, Tokyo, Japan, and "IRA 411", an anion exchange resin commercialized by Organo Corporation, Tokyo, Japan. The resulting solution was filtrated and concentrated using an evaporator, and a 30% (w/w) glucan solution was obtained in a yield of 85.8%, on a dry solid basis, from the partial starch hydrolyzate used as substrate.

Experiment 2

Preparation of a Glucan Using α-Glucosyltransferase from *Arthrobacter Globiformis* PP349 (FERM BP-10770)

Experiment 2-1

Preparation of α-Glucosyltransferase from *Arthrobacter globiformis* PP349 (FERM BP-10770)

Except for inoculating *Arthrobacter globiformis* PP349, FERM BP-10770, instead of *Bacillus circulans* PP710, FERM BP-10771, a seed culture was prepared according to the method in Experiment 1-1.

A fresh preparation of the same culture medium used for the seed culture was placed in twelve 500 ml-Erlenmeyer flasks in respective amounts of 100 ml, sterilized by heating and cooled to 27° C. Successively, one milliliter each of the above seed culture was inoculated and followed by cultivation under rotary-shaking conditions at 27° C. for 24 hours. After completion of the culture, the culture broth was withdrawn from each of Erlenmeyer flasks and centrifuged at 8,000 rpm for 20 minutes to remove cells. The α-glucosyltransferase activity of the resulting culture supernatant was assayed and determined to be 0.53 unit/ml. About one liter of the culture supernatant was salted out by adding ammonium sulfate to give finally 80% saturation and allowing it to stand at 4° C. for 24 hours. The resultant precipitates were collected by centrifuging at 11,000 rpm for 30 min, dissolved in 20 mM acetate buffer (pH 6.0), and dialyzed against the same buffer to obtain about 20 ml of a crude enzyme solution. The crude enzyme solution was subjected to anion-exchange column chromatography using 20 ml of "DEAF-TOYOPEARL™ 650S" gel, an anion-exchange gel commercialized by Tosoh Corporation, Tokyo, Japan, pre-equilibrated with 20 mM acetate buffer (pH 6.0). After eluting non-absorbed proteins, the active fractions were eluted by a linear gradient of zero to 0.5 M sodium chloride. The active fractions, eluted at about 0.05 to 0.2 M sodium chloride, were collected and dialyzed against 20 mM acetate buffer (pH 6.0). The resulting dialyzate was used as a preparation of α-glucosyltransferase.

Experiment 2-2

Preparation of a Branched α-Glucan Using α-Glucosyltransferase

One hundred milliliter of the preparation of α-glucosyltransferase, obtained in Experiment 2-1, was used as an enzyme solution. "PINEDEX® #100", a partial starch hydrolyzate commercialized by Matsutani Chemical Industries Co., Ltd., Hyogo, Japan, was admixed with the enzyme solution to give a final concentration of 30% (w/v), followed by the enzyme reaction at 40° C. for 72 hours, and then heated at about 100° C. for 10 minutes to stop the reaction. After removing the resultant insoluble substances by filtration, the filtrate was decolored and desalted using "DIAION™ SK-1B" and "DIAION™ WA30", ion exchange resins commercialized by Mitsubishi Chemical Corporation, Tokyo, Japan, and "IRA 411", an anion exchange resin commercialized by Organo Corporation, Tokyo, Japan. The resulting solution was filtrated and concentrated using a evaporator, and a 30% (w/w) glucan solution was obtained in a yield of 83.6%, on a dry solid basis, from the partial starch hydrolyzate used as substrate.

In the following Experiments 3 and 4, the glucans, obtained in Experiments 1-2 and 2-2, were called to "Glucan A" and "Glucan B", respectively, for the distinction.

Experiment 3

Evaluation of Glucan A and B as WSDF

According to the method described in Section 8, Dietary fiber, (2) High-performance liquid chromatography (Enzyme-HPLC method), "Methods for analyzing nutritional components (Appendix 1-3 of Nutrition Labeling Standard) in Nutrition Labeling Standard (Notification No. 146 of Ministry of Health, Labour, and Welfare, May, 1986)", the WSDF contents of Glucans A and B were determined as follows: "DIETARY FIBER, TOTAL ASSAY, CONTROL KIT", a kit for determining total amount of dietary fiber, commercialized by Sigma-Aldrich Japan, was used as a kit for enzymatic treatments. "PINEDEX® #100", a partial starch hydrolyzate commercialized by Matsutani Chemical Industries Co., Ltd., Hyogo, Japan, used for preparing Glucans A and B as substrate, was used as Control 1. "PINEFIBER®", a commercially available low-digestible glucan commercialized by Matsutani Chemical Industries Co., Ltd., Hyogo, Japan, was used as Control 2.

<Preparation of Sample Solution for Analyses>

To a test tube, 0.1 g-dry solid of each glucan was sampled and then admixed with 5 ml of 0.08 M sodium phosphate buffer to adjust the pH to 6.0. Successively, 0.01 ml of a thermostable α-amylase (which is derived from *Bacillus licheniformis* and commercialized by Sigma-Aldrich Japan) solution, attached to the kit, was admixed with the above solution and then the tube containing the mixture was wrapped with aluminum foil, and followed by the enzyme reaction in a boiling water bath with stirring at 5 min-interval for 30 min. After the reaction, the reaction mixture was cooled and adjusted the pH to 7.5 by adding 1 ml of 0.275 M sodium hydroxide solution. The resulting solution was admixed with 0.01 ml of a protease (which is derived from *Bacillus licheniformis* and commercialized by Sigma-Aldrich Japan) solution, attached to the kit, and then the tube containing the mixture was wrapped with aluminum foil, and followed by the enzyme reaction in a water bath with shaking at 60° C. for 30 min, and then cooled. After adjusting the pH of the resulting solution after the protease treatment to 4.3 by adding about 1 ml of 0.325 M hydrochloric acid solution, the resulting solution was further admixed with 0.01 ml of the amyloglucosidase (which is derived from *Aspergillus niger* and commercialized by Sigma-Aldrich Japan) solution, attached to the kit, and then the tube containing the mixture was wrapped with aluminum foil, and followed by the enzyme reaction in a water bath with shaking at 60° C. for 30 min, and then cooled. Successively, about 7 ml of the resulting reaction mixture was subjected to an ion-exchange column, which is prepared by mixing "AMBERLITE™ IRA-67" (OH-form) and "AMBERLITE™ 200CT" (H-form), both commercialized by Organo Corporation, Tokyo, Japan, in a ratio of 1:1, eluted at SV 1.0 for desalting, and further eluted with about 3-folds volume of deionized water, and then filled up to the total volume of about 28 ml. The elute was concentrated using an evaporator, filtrated using a membrane filter with a pore size of 0.45 μm, and then filled up to 25 ml to make into a sample solution for the analysis.

<Conditions for High-Performance Liquid Chromatography>

The test sample solution, obtained by the method described above, was subjected to a high performance liquid chromatography under the following conditions:

Column: "TSK Gel™ G2500PWXL" (ID 7.8 mm×length 300 mm), produced by Tosoh Corporation, Tokyo, Japan; two columns were connected in series
Eluent: Deionized water
Saccharide concentration of test sample: 0.8% (w/w)
Column temperature: 80° C.
Flow rate: 0.5 ml/min
Detector: Refractive index detector
Injection: 20 μl Time for analysis: 50 min <Calculation of the Dietary Fiber Content in the Test Samples>

In the chromatogram obtained by the above HPLC, undigested glucan which remained after the enzyme treatments was assumed to WSDF. The peak areas of the WSDF and glucose formed by the digestion were measured, respectively. Separately, the amount of glucose in the test sample was determined by conventional glucose oxidase-peroxidase method. Using the values of the above peak areas and the amount of glucose, the amount of the WSDF was calculated by the following Formula 1. Then, the WSDF content in the test sample was calculated by the following Formula 2.

The amount of WSDF*(mg)={(The peak area of WSDF)/(The peak area of glucose)}×(The amount of glucose in the test sample solution)** (mg)   Formula 1

*: Water-soluble dietary fiber
**: Concentration of glucose in the test sample solution (mg/ml)×25 ml The WSDF content(%,w/w)={(The amount of WSDF in the test sample)(mg)/(The amount of the test sample)(mg)}×100   Formula 2

The WSDF contents of Glucans A and B, calculated by the above Enzyme-HPLC method, were 42.1% (w/w) and 41.8% (w/w), respectively. While, in the case of the partial starch hydrolyzate, Control 1, it was completely hydrolyzed into glucose by the enzyme treatments, and the WSDF content of the partial starch hydrolyzate was estimated to be zero % (w/w). That of "PINEFIBER®", a low-digestible dextrin commercialized by Matsutani Chemical Industries Co., Ltd., Hyogo, Japan, Control 2, was estimated to be 48.7% (w/w). These results indicate that a glucan which shows the almost equal WSDF content with a commercial low-digestible dextrin can be easily prepared by allowing the α-glucosyltransferase of the present invention to act on a partial starch hydrolyzate, not comprising WSDF, as a substrate.

Experiment 4

Structural Analyses of Glucans A and B

Experiment 4-1

Methylation Analysis

According to conventional method, Glucans A and B, respectively obtained in Experiments 1-2 and 2-2, were subjected to the methylation analyses, and the resulting partially methylated products were subjected to the gas chromatography under the following conditions, and the results are in Table 3:

<Conditions for Gas Chromatography>
Column: "DB-15" (ID 0.25 mm×length 30 m, film thickness 1 μm), a capillary column produced by J&W Scientific, Tokyo, Japan;
Carrier gas: Helium
Column temperature: kept at 130° C. for 2 min, heated to 250° C. in a rate of 5° C./min, and then kept at 250° C. for 20 min
Flow rate: 1.0 ml/min
Detector: FID
Injection: 3 μl (split: 1/30)
Time for analysis: 46 min

TABLE 3

| | | Composition (Peak area %) | | |
| --- | --- | --- | --- | --- |
| Partially methylated product | Corresponding Glc** | Partial starch hydrolyzate* (Material) | Glucan A | Glucan B |
| 2,3,4,6-Tetramethylated product | Non-reducing end Glc | 5.8 | 10.1 | 9.8 |
| 3,4,6-Trimethylated product | Glc involving 1,2-linkage | 0.0 | 0.0 | 0.0 |
| 2,4,6-Trimethylated product | Glc involving 1,3-linkage | 0.0 | 1.1 | 0.9 |
| 2,3,6-Trimethylated product | Glc involving 1,4-linkage | 89.8 | 51.5 | 49.1 |
| 2,3,4-Trimethylated product | Glc involving 1,6-linkage | 0.0 | 32.2 | 33.9 |
| 2,4-Dimethylated product | Glc involving 1,3,6-linkage | 0.0 | 0.8 | 1.1 |
| 2,3-Dimethylated product | Glc involving 1,4,6-linkage | 4.4 | 4.5 | 5.2 |

*PINEDEX ® #100, a partial starch hydrolyzate commercialized by Matsutani Chemical Industries Co., Ltd.
**Glucose residue
Glucan A: Glucan prepared by using α-glucosyltransferase from strain PP710
Glucan B: Glucan prepared by using α-glucosyltransferase from strain PP349

As is evident from the results in Table 3, in both cases of Glucans A and B, 2,3,6-trimethylated product was significantly decreased and 2,3,4-trimethylated product was significantly increased to 30% or higher in comparison with the results of methylation analysis of Glucans A and B, which were respectively prepared using α-glucosyltransferase derived from *Bacillus cruculans* PP710 and *Arthrobacter globiformis* PP349; and that of the partial starch hydrolyzate used as substrate. These results indicate that the partial starch hydrolyzate having a structure of polymerizing glucoses mainly via α-1,4 linkages is converted into the branched α-glucan having 30% or higher of α-1,6 linkages by the reaction of α-glucosyltrasferase from *Bacillus circulans* PP710 and *Arthrobacter globiformis* PP349. It was also revealed that non-reducing ends, α-1,3 linkages and α-1,3,6 linkages were newly formed because 2,3,4,6-tetramethylated product, 2,4,6-trimethylated product, and 2,4-dimethylated product were also increased. The contents of 2,4,6-trimethylated product and 2,4-dimethylated product in the partially-methylatedproducts of Glucan A were 1.1% and 0.8%, respectively. The contents of 2,4,6-trimethylated product and 2,4-dimethylated product in the partially methylated products of Glucan B were 0.9% and 1.1%, respectively. Further, it was considered that the content of α-1,4,6 linkage, which is inherently present in the substrate as a branched point, was not so changed because the contents of 2,3-dimethylated product in the partially methylated products from Glucans A and B were not so different from that from the substrate. From these results, it was revealed that Glucans A and B were a branched glucan (branched α-glucan) having α-1,4 linkage and α-1,6 linkage as major glucosidic linkage and α-1,3 linkage and α-1,3,6 linkage as minor glucosidic linkage different from the partial starch hydrolyzate used as substrate. It was also revealed from their $^1$H-NMR spectra obtained by NMR analyses that all amomeric form of C-1 position of glucose, constituting Glucans A and B, were α-form.

Experiment 4-2

Isomaltodextranase Digestion of Branched α-Glucan A and B

In order to characterize the structures of Branched α-glucans A and B, isomaltodextranse digestion of them was carried out. An aqueous solution of Branched α-glucan A or B with a final concentration of 1% (w/v) was admixed with 100 units/g-solid substrate of isomaltodextranase, derived from *Arthrobacter globiformis* and prepared in Hayashibara Biochemical Laboratories Inc., Okayama, Japan; and followed the enzyme reaction at pH 5.0 and 50° C. for 16 hours. After stopping the reaction by keeping at 100° C. for 10 min, the saccharide composition in the resulting reaction mixture was determined using high-performance liquid chromatography (hereinafter, abbreviated as "HPLC") and gas chromatography (hereinafter, abbreviated as "GC"). HPLC was carried out under the following conditions:
<Conditions for HPLC>
    Column: "MCI GEL CKO4SS", produced by Mitsubishi Chemical Corporation, Tokyo, Japan; two columns were connected in series
    Eluent: Water
    Column temperature: 80° C.
    Flow rate: 0.4 ml/min
    Detector: "RID-10A", a refractive index detector produced by Shimadzu Corporation, Kyoto, Japan.
GC was carried out after converting saccharides into trimethylsiliyl-derivatives (TMS-derivatives) and under the following conditions:
<Conditions for GC>
    Column: "2% Silicon OV-17 Chromosorb W/AW-DMS", produced by GL Science, Tokyo, Japan;
    Column temperature: raised 160° C. to 320° C. in a rate of 7.5° C./min
    Carrier gas: Nitrogen
    Detector: FID.
By the isomaltodextranase digestion, no isomaltose was formed from the partial starch hydrolyzate, the substrate used for preparing the branched α-glucan. On the contrary, isomaltose in amounts of 28.4% (w/w) and 27.2% (w/w) were formed from Branched α-glucan A and B, respectively, by the digestion. These results indicate that Branched α-glucan A and B have isomaltose structure in amounts of about 28.4% (w/w) and 27.2% (w/w). Also, they support the results of the methylation analyses in Experiment 4-1, showing that the ratio of α-1,6 linkage is increased in the branched α-glucan. Since isomaltodextranase has a specificity of hydrolyzing α-glucosidic linkage adjacent to the reducing end of isomaltose structure in glucan with no distinction of α-1,3, α-1,4, and α-1,6 linkages, it is not clear in detail how the resulting isomaltose are bound via any one of the above linkages.

Experiment 4-2

α-Glucosidase/Glucoamylase Double Digestion of Branched α-Glucan A and B

α-Glucosidase/glucoamylase double digestion test of Branched α-glucan A or B was carried out by allowing "TRANSGLUCOSIDASE AMANO L", α-glucosidase from *Aspergillus niger* and glucoamylase from *Rhizopus* sp. to act simultaneously on Branched α-glucan A or B. The aqueous solution containing Branched α-glucan A or B was admixed with 5,000 units/g-solid-substrate of α-glucosidase and 100 units/g-solid-substrate of glucoamylase and followed by the enzyme reaction at pH 5.5 and 50° C. for 16 hours. After stopping the reaction by keeping the reaction mixture at 100° C. for 10 min, the saccharide composition of the reaction mixture was analyzed by HPLC under the same condition in Experiment 4-2. As a result, both Branched α-glucan A and B were substantially hydrolyzed into glucose as in the case of the partial starch hydrolyzate used as substrate for preparing the branched α-glucans. These results indicate that both Branched α-glucan A and B are α-glucan constructed by glucose molecules as component sugar.

Experiment 4-4

Analysis of the Molecular Weight Distribution

Figure 1:
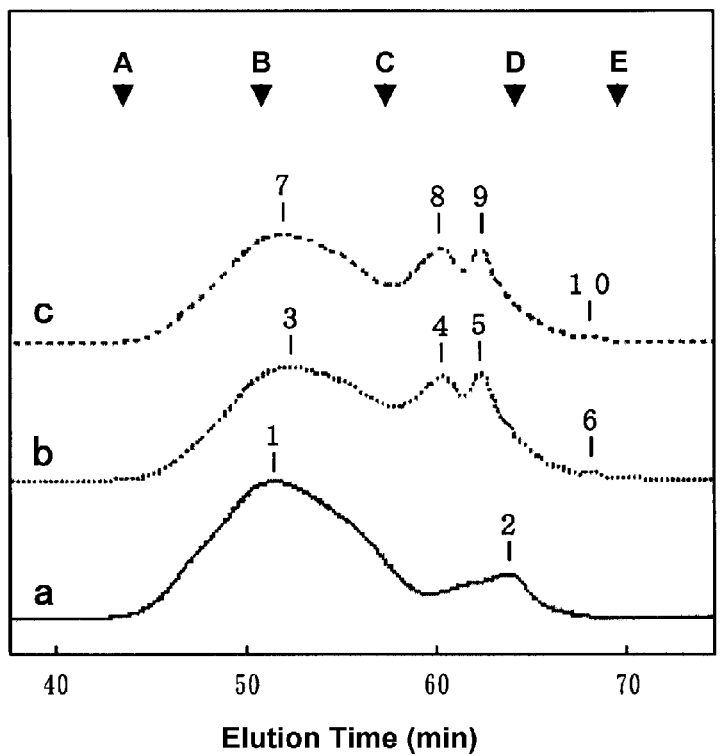
FIG. 1 shows a comparison of gel-filtration HPLC chromatograms of Glucans A and B, respectively prepared from partial starch hydrolyzate by using α-glucosyltransferase from *Bacillus circulans* PP710 and from *Arthrobacter globiformis* PP349, and that of partial starch hydrolyzate used as substrate for the enzymes.

The molecular weight distributions of Branched α-glucans A and B were analyzed by the conventional gel-filtration HPLC. The gel-filtration HPLC was carried out by the following conditions:
<Conditions for Gel-Filtrating HPLC>
    Column: "TSK GEL α-M", produced by Tosoh Corporation, Tokyo, Japan; two columns were connected in series
    Eluent: 10 mM sodium phosphate buffer (pH 7.0)
    Column temperature: 40° C.
    Flow rate: 0.3 ml/min
    Detector: "RID-10A", a refractive index detector produced by Shimadzu Corporation, Kyoto, Japan.
The molecular weight of glucans in the samples was calculated based on the molecular weight-calibration curve prepared by subjecting "Standard pullulan for measuring molecular weight", commercialized by Hayashibara Biochemical Laboratories Inc., Okayama, Japan, to the same gel filtration HPLC analysis. FIG. 1 shows a comparative gel-filtration HPLC chromatograms of Branched α-glucans A and B (Symbols "b" and "c" in FIG. 1), and "PINEDEX® #100", the partial starch hydrolyzate (Symbol "a" in FIG. 1) used as substrate for preparing Branched α-glucan A and B. In FIG. 1, symbols "A", "B", "C", "D", and "E" mean the positions of eluting glucan having a molecular weight of 1,000,000, 100,000, 10,000, 1,000, and 100 daltons, respectively. (Also in the cases of FIGS. 15 and 19 mentioned after) The results of the molecular weight distribution analyses of samples based on the gel-filtration HPLC chromatograms are in Table 4.

TABLE 4

| Analytical data | Partial starch hydrolyzate* (Material) | Glucan A | Glucan B |
|---|---|---|---|
| Number average molecular weight (Mn) (Dalton) | 6,680 | 3,840 | 4,050 |
| Weight-average molecular weight (Mw) (Dalton) | 98,890 | 59,000 | 65,700 |
| Mw/Mn | 14.8 | 15.4 | 16.2 |
| Average glucose polymerization degree of peaks | 449 and 6.3 | 384, 22.2, 10.9, and 1 | 433, 22.8, 10.9, and 1 |

*PINEDEX® #100, a partial starch hydrolyzate commercialized by Matsutani Chemical Industries Co., Ltd., Hyogo, Japan
Glucan A: Glucan prepared by using α-glucosyltransferase from strain PP710
Glucan B: Glucan prepared by using α-glucosyltransferase from strain PP349

In the molecular weight distribution analysis, the partial starch hydrolyzate used as substrate was characterized as a saccharide mixture showing two peaks (Symbols "1" and "2" in the chromatogram "a" in FIG. 1) corresponding to the glucose polymerization degree of 499 and 6.3. While, Branched α-glucan A was characterized as a saccharide mixture showing four peaks (Symbols "3", "4", "5", and "6" in the chromatogram "b" in FIG. 1) corresponding to the glucose polymerization degree of 384, 22.2, 10.9, and 1. Branched α-glucan B was characterized as a saccharide mixture showing four peaks (Symbols "7", "8", "9", and "10" in the chromatogram "c" in FIG. 1) corresponding to the glucose polymerization degree of 433, 22.8, 10.9, and 1. The peaks of symbol "6" and "10" correspond to glucose and the facts that the amounts of glucose are low indicate that the enzyme from *Bacillus criculans* PP710 and *Arthrobacter globiformis* PP349 has a relatively weak hydrolytic activity. As is evident from Table 4, both the number average molecular weight and the weight-average molecular weight of Glucan A and B were decreased to about 60% of those of the partial starch hydrolyzate used as substrate, and Glucan A and B were converted into molecules with a low-molecular weight as a whole. The value of dividing the weight-average molecular weight with the number average molecular weight (Mw/Mn), which is an index of molecula weigh distribution, was not so changed among the partial starch hydrolyzate, Glucan A and Glucan B. From the results, it was considered that the both α-glucosyltransferases from *Bacillus circulans* PP710 and *Arthrobacter globiformis* PP349 specifically act on non-reducing ends of the partial starch hydrolyzate.

From the results in Table 3, it was revealed that, in the partial starch hydrolyzate used as substrate, about 90% of glucosidic linkages are α-1,4 linkages and α-1,4,6 linkages are slightly present in the molecule. On the contrary, it was revealed that, in Glucans A and B, the ratio of α-1,6 linkage to α-1,4 linkage is significantly high, and Glucan A and B also have α-1,3 linkages and α-1,3, 6 linkages in addition to α-1,4,6 linkages. The branched α-glucan having a structure as such has been hitherto unknown.

Figure 2:
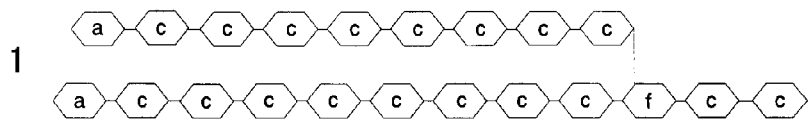
FIG. 2 shows the reference diagrams of the structures of partial starch hydrolyzate and the branched α-glucan of the present invention.
Figure 2:
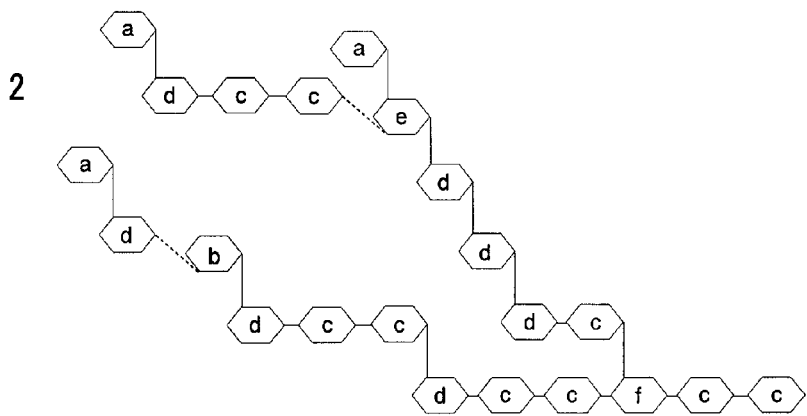

The structure of the branched α-glucan of the present invention was deduced based on the results obtained by the methylation analysis. The reference diagram of the branched α-glucan is shown in FIG. 2 together with that of the partial starch hydrolyzate used as substrate. In FIG. 2, symbols "1" and "2" respectively represent reference diagrams of the partial starch hydrolyzate used as substrate and the branched α-glucan. Also, in FIG. 2, symbols "a", "b", "c", "d", "e", and "f" represent non-reducing end glucose residue, glucose residue involving α-1,3 linkage, that involving α-1,4 linkage, that involving α-1,6 linkage, that involving α-1,3,6 linkage, and that involving α-1,4,6 linkage, respectively, in the partial starch hydrolyzate and the branched α-glucan of the present invention. Further, in the reference diagrams, diagonal broken line, horizontal solid line, and vertical solid line, between glucose residues represent α-1,3 linkage, α-1,4 linkage, and α-1,6 linkage, respectively.

Experiment 5

Preparation of the α-Glucosyltransferase from *Bacillus circulans* PP710

A liquid culture medium consisting of 1.5% (w/v) of "PINEDEX® #4", a partial starch hydrolyzate commercialized by Matsutani Chemical Industries Co., Ltd., Hyogo, Japan, 0.5% (w/v) of "POLYPEPTONE", a yeast extract commercialized by Nihon Pharmaceutical Co., Ltd., Tokyo, Japan, 0.1% (w/v) of "YEAST EXTRACT S", a yeast extract commercialized by Nihon Pharmaceutical Co., Ltd., Tokyo, Japan, 0.1% (w/v) of dipotassium phosphate, 0.06% (w/v) of sodium phosphate dihydrate, 0.05% (w/v) of magnesium sulfate hepta-hydrate, 0.001% (w/v) of manganese sulfate penta-hydrate, 0.001% (w/v) of ferrous sulfate hepta-hydrate, and water was placed in a 500 ml-Erlenmeyer flask in a amount of 100 ml, sterilized by autoclaving at 121° C. for 20 min, and cooled. Successively, the culture medium was inoculated with *Bacillus circulans* PP710, FERM BP-10771, and followed by cultivation under rotary-shaking conditions at 27° C. and 230 rpm for 48 hours to obtain a seed culture.

About 20 L of a fresh preparation of the same liquid culture medium as used in the above seed culture were placed in a 30-L fermenter, sterilized by heating, and then cooled to 27° C. and inoculated with about 200 ml of the seed culture, followed by the cultivation at 27° C. and pH 5.5 to 8.0 for 24 hours under aeration-agitation conditions. After completion of the cultivation, the resulting culture broth was distilled from the fermenter and removed cells by centrifuging at 8,000 rpm for 20 min, and about 18 L of culture supernatant was obtained. The α-glucosyltransferase activities in the culture broth and culture supernatant were assayed. About 2.7 units/ml and about 2.6 units/ml of the enzyme activities were detected in the culture broth and the culture supernatant, respectively. It was revealed that major part of the α-glucosyltransferase of the present invention, produced by *Bacillus circulans* PP710, was secreted extracellularly.

Experiment 6

Purification of the α-Glucosyltransferase from *Bacillus circulans* PP710

About four liters (Total activity: about 10,400 units) of the culture supernatant obtained in Experiment 5 was salted out by adding ammonium sulfate to give finally 80% saturation and allowing it to stand at 4° C. for 24 hours. The resultant precipitates were collected by centrifuging at 11,000 rpm for 30 min, dissolved in 20 mM acetate buffer (pH 4.5), and dialyzed against the same buffer to obtain about 65 ml of a crude enzyme solution. The crude enzyme solution had about 74 units/ml (Total activity: about 4,780 units) of the α-glucosyltransferase. The crude enzyme solution was subjected to cation-exchange column chromatography using 70 ml of "CM-TOYOPEARL™ 650S" gel, a cation-exchange gel commercialized by Tosoh Corporation, Tokyo, Japan. The α-glucosyltransferase activity was adsorbed on "CM-TOYOPEARL™ 650S" gel pre-equilibrated with 20 mM acetate buffer (pH 4.5) and eluted at about 0.4 M sodium chloride when the elution was carried out with a liner gradient of zero to 0.5 M of sodium chloride. The active fractions were collected and admixed with ammonium sulfate to give a final concentration of 1 M, and then allowed to stand at 4° C. for 24 hours. The enzyme solution was centrifuged to remove precipitates, and subjected to hydrophobic column chromatography using 9 ml of "BUTYL-TOYOPEARL™ 650M" gel, a gel commercialized by Tosoh Corporation, Tokyo, Japan. The α-glucosyltransferase activity was adsorbed on "BUTYL-TOYOPEARL™ 650M" gel pre-equilibrated with 20 mM acetate buffer (pH 6.0) containing 1 M of ammonium sulfate and when eluted with a linear gradient decreasing from 1 M to zero M of ammonium sulfate, the enzyme activity was eluted at about 0.2 M of ammonium sulfate. The active fractions were collected, dialyzed against 20 mM acetate buffer (pH 4.5), and subjected to cation-exchange column chromatography using 3.3 ml of "CM-5PW™" gel, a gel commercialized by Tosoh Corporation, Tokyo, Japan. The α-glucosyltransferase activity was adsorbed on "CM-5PW™" gel pre-equilibrated with 20 mM acetate buffer (pH 4.5) and when eluted with a linear gradient of zero to 1 M of sodium chloride, the enzyme activity was eluted at about 0.4 M of sodium chloride. The active fractions were collected and dialyzed against 20 mM acetate buffer (pH 6.0). The amount of enzyme activity, specific activity, and yield of the α-glucosyltransferase at each purification step are in Table 5.

TABLE 5

| Purification step | α-Glucosyl-transferase activity (units) | Specific activity of α-glucosyl-transferase (units/mg-protein) | Yield (%) |
|---|---|---|---|
| Culture supernatant | 10,400 | 10 | 100 |
| Dialyzed solution after salting out with ammonium sulfate | 4,780 | 22.8 | 46.0 |
| Eluate from ion-exchange column chromatography | 3,960 | 265 | 38.1 |
| Eluate from hydrophobic column chromatography | 3,800 | 307 | 36.5 |
| Eluate from ion-exchange column chromatography | 3,300 | 327 | 31.7 |

The finally purified enzyme preparation of the α-glucosyltransferase was assayed for purity on gel electrophoresis using a 5-20% (w/v) gradient polyacrylamide gel and detected on the gel as a single protein band, i.e., a high purity preparation.

Experiment 7

Properties of the α-Glucosyltransferase from *Bacillus circulans* PP710

Experiment 7-1

Molecular Weight

The purified enzyme preparation of the α-glucosyltransferase, obtained by the method in Experiment 6, was subjected to SDS-PAGE (a 5 to 20% (w/v) gradient gel) and the molecular weight of the enzyme was measured comparing with molecular weight markers, commercialized by Bio-Rad Japan, Tokyo, Japan. It was revealed that the α-glucosyltransferase has a molecular weight of 90,000±10,000 daltons.

Experiment 7-2

Optimum Temperature and Optimum pH for the Enzyme Reaction

Figure 3:
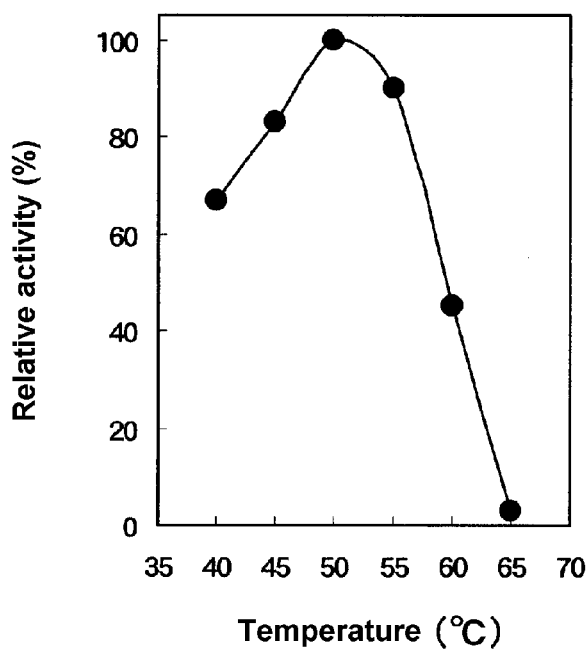
FIG. 3 shows the optimum temperature of α-glucosyltransferase from *Bacillus circulans* PP710.
Figure 4:
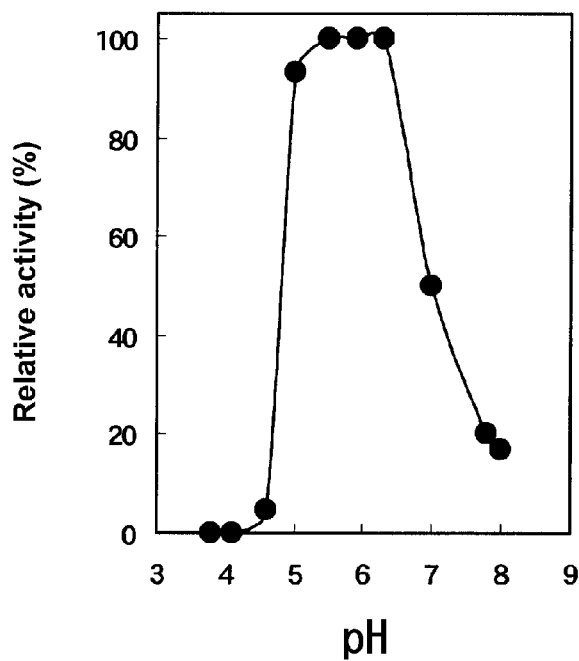
FIG. 4 shows the optimum pH of α-glucosyltransferase from *Bacillus circulans* PP710.

Effects of temperature and pH on the enzyme activity were investigated using the purified enzyme preparation of the α-glucosyltransferase, obtained by the method in Experiment 6, by varying temperature and pH at the assay of the enzyme. The results are in FIG. 3 (Optimum temperature) and FIG. 4 (Optimum pH), respectively. It was revealed that the optimum temperature of the α-glucosyltransferase was 50 to 55° C. when reacted at pH 6.0 for 30 min and the optimum pH was 5.0 to 6.3 when reacted at 40° C. for 30 min.

Experiment 7-3

Thermal and pH Stabilities of the Enzyme

Figure 5:
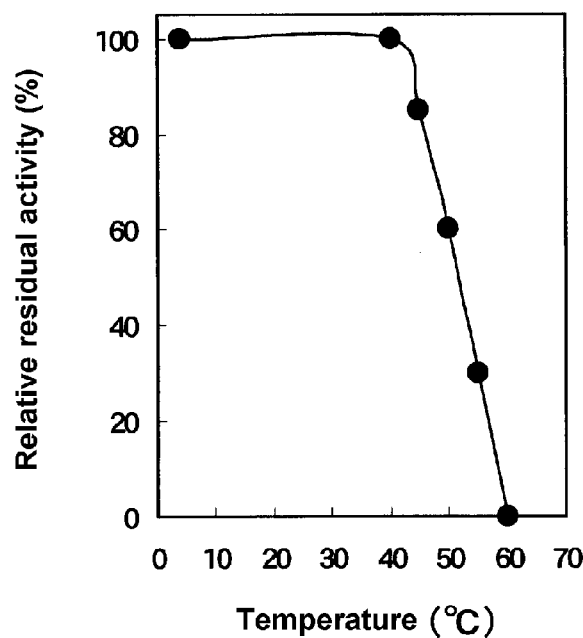
FIG. 5 shows the thermal stability of α-glucosyltransferase from *Bacillus circulans* PP710.
Figure 6:
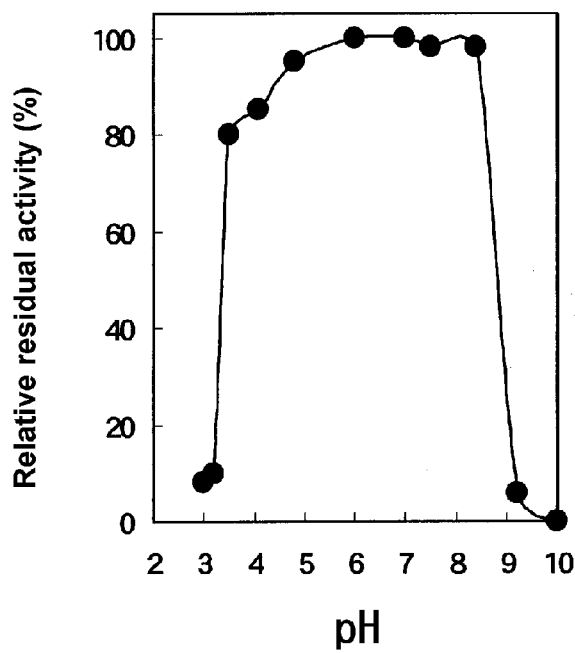
FIG. 6 shows the pH stability of α-glucosyltransferase from *Bacillus circulans* PP710.

Thermal stability and pH stability of the enzyme were investigated using the purified enzyme preparation of the α-glucosyltransferase, obtained by the method in Experiment 6. Thermal stability of the enzyme was determined by the steps of incubating an enzyme solution (20 mM acetate buffer, pH 6.0) under various temperatures for 60 min, cooling in water, and measuring the residual enzyme activity. pH Stability of the enzyme was determined by the steps of incubating enzyme solution in 20 mM buffer at various pHs, and at 4° C. for 24 hours, adjusting the pH to 6.0, and measuring the residual enzyme activity. The results are in FIG. 5 (Thermal stability) and in FIG. 6 (pH Stability), respectively. As is evident from the results in FIGS. 5 and 6, the α-glucosyltransferase is stable up to 40° C. and in the range of pH 3.5 to 8.4.

Experiment 7-4

Effects of Metal Ions on the Enzyme Activity

Effects of metal ions on the enzyme activity were investigated using the purified enzyme preparation of the α-glucosyltransferase, obtained by the method in Experiment 6, in the presence of 1 mM of respective metal ions according to the assay method. The results are in Table 6.

TABLE 6

| Metal salt | Relative activity (%) | Metal salt | Relative activity (%) |
|---|---|---|---|
| None | 100 | $MgCl_2$ | 102 |
| $CaCl_2$ | 101 | $MnCl_2$ | 99 |
| $CoCl_2$ | 100 | $NiCl_2$ | 102 |
| $CuCl_2$ | 52 | $ZnCl_2$ | 101 |
| $FeCl_2$ | 91 | $PbCl_2$ | 97 |
| $FeCl_3$ | 94 | EDTA | 99 |
| $HgCl_2$ | 3 | | |

As is evident from the results in Table 6, it was revealed that the α-glucosyltransferase activity was remarkably inhibited by $Hg^{2+}$ ion and moderately by $Cu^{2+}$ ion, respectively.

Experiment 8

Preparation of the α-glucosyltransferase from *Arthrobacter globiformis* PP394 (FERM BP-10700)

Except for inoculating *Arthrobacter globiformis* PP349, FERM BP-10770, instead of *Bacillus circulans* PP710, FERM BP-10771, a seed culture was prepared according to the method in Experiment 1-1.

About 20 L of a fresh preparation of the same liquid culture medium as used in the above seed culture were placed in a 30-L fermenter, sterilized by heating, and then cooled to 27° C. and inoculated with about 200 ml of the seed culture, followed by the cultivation at 27° C. and pH 5.5 to 7.0 for 24 hours under aeration-agitation conditions. After completion of the cultivation, the resulting culture broth was distilled from the fermenter and removed cells by centrifuging at 8,000 rpm for 20 min, and about 18 L of culture supernatant was obtained. The α-glucosyltransferase activities in the culture broth and culture supernatant were assayed. About 0.36 unit/ml and about 0.42 unit/ml of the enzyme activities were detected in the culture broth and the culture supernatant, respectively. It was revealed that major part of the α-glucosyltransferase, produced by *Arthrobacter globiformis* PP349, was secreted extracellularly.

Experiment 9

Purification of the α-Glucosyltransferase from *Arthrobacter globiformis* PP394

About 18 liters (Total activity: about 7,560 units) of the culture supernatant obtained in Experiment 8 was salted out by adding ammonium sulfate to give finally 80% saturation and allowing it to stand at 4° C. for 24 hours. The resultant precipitates were collected by centrifuging at 11,000 rpm for 30 min, dissolved in 20 mM acetate buffer (pH 6.0), and dialyzed against the same buffer to obtain about 500 ml of a crude enzyme solution. The crude enzyme solution had about 14 units/ml (Total activity: about 7,000 units) of the α-glucosyltransferase. The crude enzyme solution was admixed with ammonium sulfate to give a final concentration of 2 M, centrifuged to remove precipitates, and then subjected to hydrophobic column chromatography using 300 ml of "PHENYL-TOYOPEARL™ 650M" gel, a gel commercialized by Tosoh Corporation, Tokyo, Japan. The α-glucosyltransferase activity was adsorbed on "PHENYL-TOYOPEARL™ 650M" gel pre-equilibrated with 20 mM acetate buffer (pH 6.0) containing 2 M of ammonium sulfate and when eluted with a linear gradient decreasing from 2 M to zero M of ammonium sulfate, the enzyme activity was eluted at about 0.6 M of ammonium sulfate. The active fractions were collected, dialyzed against 20 mM acetate buffer (pH 6.0), and subjected to anion-exchange column chromatography using 100 ml of "DEAF-TOYOPEARL™ 650S" gel, a gel commercialized by Tosoh Corporation, Tokyo, Japan. The α-glucosyltransferase activity was adsorbed on "DEAF-TOYOPEARL™ 650S" gel pre-equilibrated with 20 mM acetate buffer (pH 6.0) and when eluted with a linear gradient of zero to 0.5 M of sodium chloride, the enzyme activity was eluted at about 0.1 M of sodium chloride. The amount of enzyme activity, specific activity, and yield of the α-glucosyltransferase at each purification step are in Table 7.

TABLE 7

| Purification step | α-Glucosyl-transferase activity (units) | Specific activity of α-glucosyl-transferase (units/mg-protein) | Yield (%) |
| --- | --- | --- | --- |
| Culture supernatant | 7,560 | 1.6 | 100 |
| Dialyzed solution after salting out with ammonium sulfate | 7,000 | 5.4 | 92.6 |
| Eluate from hydrophobic column chromatography | 3,870 | 130 | 54.2 |
| Eluate from ion-exchange column chromatography | 2,710 | 415 | 35.8 |

The finally purified enzyme preparation of the α-glucosyltransferase was assayed for purity on gel electrophoresis using a 5-20% (w/v) gradient polyacrylamide gel and detected on the gel as a single protein band, i.e., a high purity preparation.

Experiment 10

Properties of α-Glucosyltransferase from *Arthrobacter globiformis* PP394

Experiment 10-1

Molecular Weight

The purified enzyme preparation of the α-glucosyltransferase from *Arthrobacter globiformis* PP349, obtained by the method in Experiment 9, was subjected to SDS-PAGE (a 5 to 20% (w/v) gradient gel) and the molecular weight of the enzyme was measured comparing with molecular weight markers, commercialized by Bio-Rad Japan, Tokyo, Japan. It was revealed that the α-glucosyltransferase has a molecular weight of 90,000±10,000 daltons.

Experiment 10-2

Optimum Temperature and Optimum pH for the Enzyme Reaction

Figure 7:
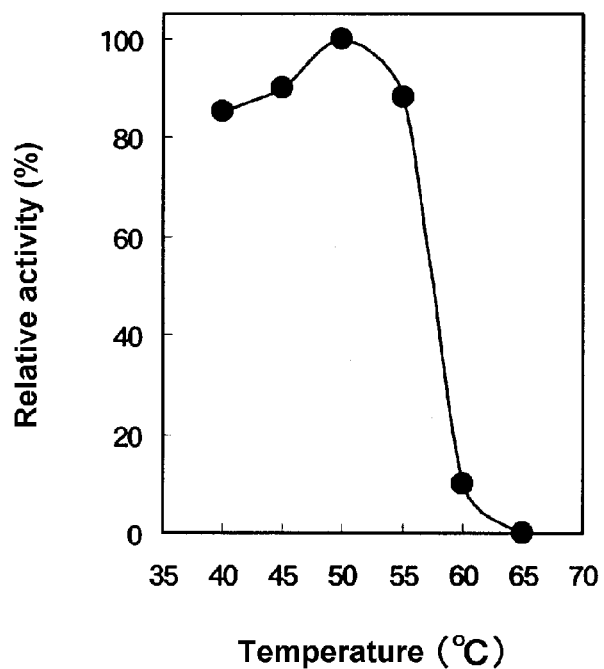
FIG. 7 shows the optimum temperature of α-glucosyltransferase from *Arthrobacter globiformis* PP349.
Figure 8:
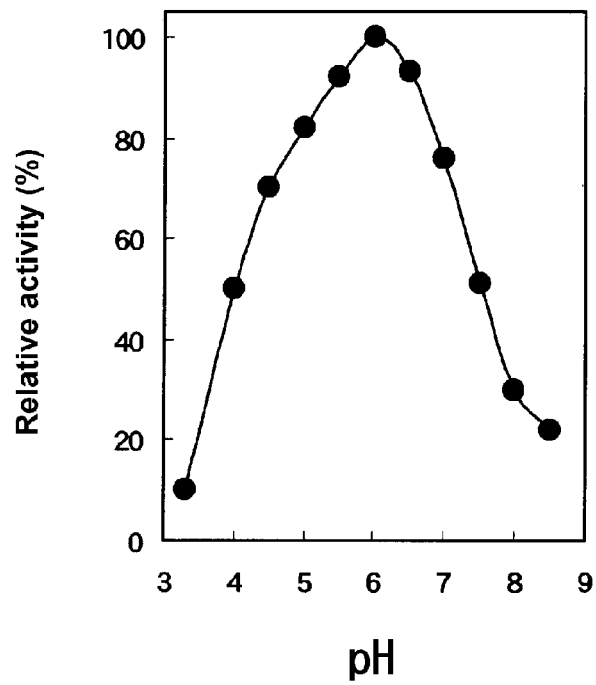
FIG. 8 shows the optimum pH of α-glucosyltransferase from *Arthrobacter globiformis* PP349.

Effects of temperature and pH on the enzyme activity were investigated using the purified enzyme preparation of the α-glucosyltransferase from *Arthrobacter globiformis* PP349, obtained by the method in Experiment 9, by varying temperature and pH at the assay of the enzyme. The results are in FIG. 7 (Optimum temperature) and FIG. 8 (Optimum pH), respectively. It was revealed that the optimum temperature of the α-glucosyltransferase was about 50° C. when reacted at pH 6.0 for 30 min and the optimum pH was about 6.0 when reacted at 40° C. for 30 min.

Experiment 7-3

Thermal and pH Stabilities of the Enzyme

Figure 9:
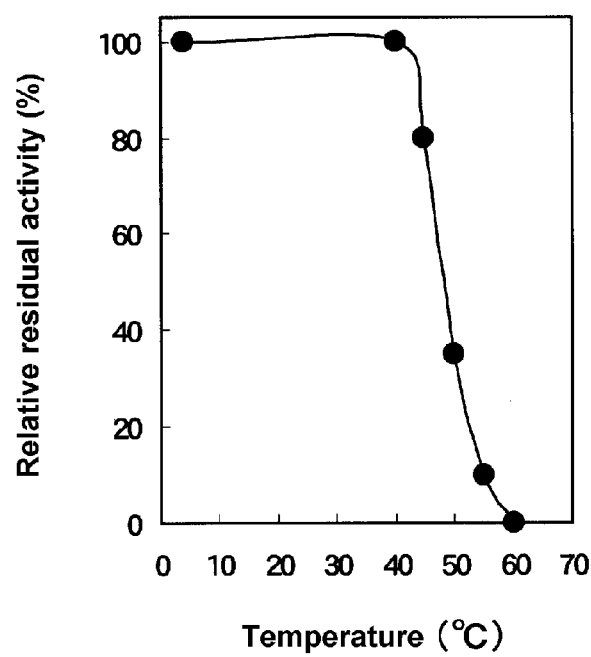
FIG. 9 shows the thermal stability of α-glucosyltransferase from *Arthrobacter globiformis* PP349.
Figure 10:
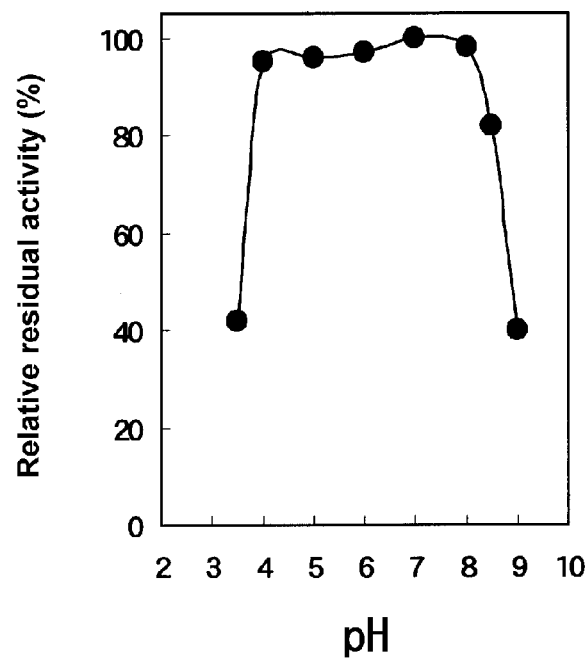
FIG. 10 shows the pH stability of α-glucosyltransferase from *Arthrobacter globiformis* PP349.

Thermal stability and pH stability of the enzyme were investigated using the purified enzyme preparation of the α-glucosyltransferase, obtained by the method in Experiment 9. Thermal stability of the enzyme was determined by the steps of incubating an enzyme solution (20 mM acetate buffer, pH 6.0) under various temperatures for 60 min, cooling in water, and measuring the residual enzyme activity. pH Stability of the enzyme was determined by the steps of incubating enzyme solution in 20 mM buffer at various pHs, and at 4° C. for 24 hours, adjusting the pH to 6.0, and measuring the residual enzyme activity. The results are in FIG. 9 (Thermal stability) and in FIG. 10 (pH Stability), respectively. As is evident from the results in FIGS. 9 and 10, the α-glucosyltransferase from *Arthrobacter globiformis* of the present invention is stable up to 40° C. and in the range of pH 4.0 to 8.0.

Experiment 7-4

Effects of Metal Ions on the Enzyme Activity

Effects of metal ions on the enzyme activity were investigated using the purified enzyme preparation of the α-glucosyltransferase, obtained by the method in Experiment 9, in the presence of 1 mM of respective metal ions according to the assay method. The results are in Table 8.

TABLE 8

| Metal salt | Relative activity (%) | Metal salt | Relative activity (%) |
|---|---|---|---|
| None | 100 | $MgCl_2$ | 104 |
| $CaCl_2$ | 104 | $MnCl_2$ | 103 |
| $CoCl_2$ | 98 | $NiCl_2$ | 100 |
| $CuCl_2$ | 45 | $ZnCl_2$ | 100 |
| $FeCl_2$ | 91 | $PbCl_2$ | 96 |
| $FeCl_3$ | 95 | EDTA | 99 |
| $HgCl_2$ | 2 | | |

As is evident from the results in Table 6, it was revealed that the α-glucosyltransferase activity was remarkably inhibited by $Hg^{2+}$ ion and moderately by $Cu^{2+}$ ion, respectively.

Experiment 11

Action on Various Saccharides

Substrate specificity of the α-glucosyltransferase of the present invention was investigated using various saccharides as substrates. Substrate solutions were prepared by dissolving methyl-α-glucoside, methyl-β-glucoside, p-nitrophenyl-α-glucoside, p-nitrophenyl-β-glucoside, glucose, sucrose, maltose, isomaltose, trehalose, kojibiose, nigerose, neotrehalose, cellobiose, lactose, maltotriose, maltotetraose, maltopentaose, maltohexaose, maltoheptaose, isomaltotriose, or isopanose, in water. Each substrate solution was admixed with acetate buffer (pH 6.0) to give a final concentration of 20 mM, and then each of the resulting substrate solution was further admixed with 10 units/g-solid-substrate of the purified preparation of α-glucosyltransferase from *Bacillus circulans* PP710, obtained by the method in Experiment 6. Successively, substrate concentration was set to 1% (w/v) and followed by the enzyme reaction at 40° C. and pH 6.0 for 24 hours. To examine the saccharides in each mixture before and after the reaction, saccharides were separated by silica gel thin-layer chromatography (hereinafter, simply abbreviated as "TLC") using "KIESELGEL™ 60", a TLC aluminum plate (10×20 cm) and a solvent (n-butanol/pyridine/water, volume ratio of 6:4:1) and two-times ascending method. The formed saccharides except for the substrate on the plate were detected by visualizing the spots by spraying 10% sulfate-methanol solution and heating. By the above TLC analyses, the enzymatic action and the degree of the reaction of the enzyme on each substrate were confirmed. The results are in Table 9. While, the substrate specificity of the α-glucosyltransferase from *Arthrobacter globiformis* PP349 was also investigated by the same method described above, and it was confirmed that the substrate specificity of the enzyme was similar with that of the enzyme from *Bacillus circulans* PP710.

TABLE 9

| Substrate | Action* | Substrate | Action* |
|---|---|---|---|
| Methyl-α-glucoside | − | Cellobiose | − |
| Methyl-β-glucoside | − | Sucrose | − |
| PNP*-α-glucoside | − | Lactose | − |
| PNP*-β-glucoside | − | Maltotriose | ++ |
| Glucose | − | Maltotetraose | ++ |
| Trehalose | − | Maltopentaose | ++ |
| Neotrehalose | + | Maltohexaose | ++ |
| Kojibiose | ± | Maltoheptaose | ++ |
| Nigerose | + | Isomaltotriose | + |
| Maltose | ++ | Isopanose | + |
| Isomaltose | + | | |

Note:
The symbol, "−" means "Not acted".
The symbol, "±" means "Slightly acted".
The symbol, "+" means "Acted".
The symbol, "++" means "Well acted".
*p-nitrophenyl As is evident from the results in Table 9, the α-glucosyltransferase of the present invention acted on maltose, maltotriose, maltotetraose, maltopentaose, maltohexaose, and maltoheptaose, and also acted on nigerose, isomaltose, neotrehalose, isomaltotriose, and isopanose among the saccharides tested. Further, the enzyme slightly acted on kojibiose. From these saccharides, the formation of glucosyltransfer products was detected together with hydrolyzates. While, the α-glucosyltransferase of the present invention did not act on methyl-α-glucoside, methyl-β-glucoside, p-nitrophenyl-α-glucoside, p-nitrophenyl-β-glucoside, trehalose, cellobiose, sucrose, lactose, etc. From these results and the fact that the α-glucosyltransferase forms the branched α-glucan from partial starch hydrolyzate, it was revealed that the enzyme widely acts on maltose and α-1,4 glucan having a glucose polymerization degree of 3 or higher, and α-glucooligosaccharides constructed by glucose molecules.

Experiment 12

Action Mechanism

For investigating the action mechanism of the α-glucosyltransferase of the present invention, the structure of the saccharide which is formed by allowing the enzyme to act on a minimum substrate, maltose, was investigated. Since the result obtained by using the α-glucosyltransferase from *Arthrobacter globiformis* PP349 was almost same with the case of using the enzyme from *Bacillus circulans* PP710, this experiment shows the results of the case of using the enzyme from *Bacillus circulans* PP710.

Experiment 12-1

Product from Maltose by the Enzyme Reaction

Aqueous maltose solution and acetate buffer (pH 6.0) were mixed to give final concentrations of 1% (w/v) and 10 mM, respectively, to make into a substrate solution. The substrate solution was admixed with 10 units/g-solid substrate of α-glucosyltransferase, obtained by the method in Experiment 6, and followed by the enzyme reaction at 40° C. and pH 6.0. Aliquots were sampled from the reaction mixture with time and the reaction was stopped by keeping at 100° C. for 10 min. The saccharide compositions of the samples were measured by HPLC and GC. HPLC and GC were carried out under the conditions described in Experiment 4-2. The results are in Table 10.

TABLE 10

| Reaction Time (hr) | Saccharide Composition (%, w/w) | | | | | | | | | |
|---|---|---|---|---|---|---|---|---|---|---|
| | DP1 | DP2 | | | DP3 | | | | | | |
| | Glucose | Maltose | Isomaltose | Neotrehalose | Maltotriose | Panose | Isopanose | Isomaltotriose | DP4 | DP5 | DP6≤ |
| 0 | 0.0 | 99.2 | 0.0 | 0.0 | 0.8 | 0.0 | 0.0 | 0.0 | 0.0 | 0.0 | 0.0 |
| 1 | 12.1 | 55.0 | 0.7 | 0.0 | 13.2 | 16.1 | 0.0 | 0.0 | 2.9 | 0.0 | 0.0 |
| 2 | 18.4 | 33.5 | 1.0 | 0.0 | 14.4 | 24.1 | 0.0 | 0.0 | 7.6 | 1.0 | 0.0 |
| 4 | 23.7 | 17.3 | 2.5 | 0.0 | 10.0 | 29.3 | 0.0 | 0.0 | 13.0 | 4.2 | 0.0 |
| 8 | 27.0 | 10.4 | 4.7 | 0.0 | 4.9 | 27.8 | 0.0 | 0.0 | 15.9 | 5.3 | 4.0 |
| 24 | 30.4 | 6.0 | 10.0 | 2.6 | 1.4 | 11.0 | 1.0 | 3.6 | 15.3 | 10.2 | 8.5 |
| 48 | 31.5 | 6.2 | 13.8 | 3.9 | 0.7 | 4.1 | 1.5 | 4.2 | 12.4 | 10.3 | 11.4 |

DP: Glucose polymerization degree

As is evident from the results in Table 10, at initial stage (after one hour) of the reaction, glucose, maltotriose, and panose were formed as major reaction products from the substrate, maltose, by the action of the α-glucosyltransferase of the present invention. Also, oligosacchardes with a glucose polymerization degree of 4 and 5 were formed when the reaction time was elapsed 2 to 4 hours. Accompanying with the progress of the reaction, the content of maltotriose reached a maximum, 14.4%, at 2 hours and then decreased; and the content of panose reached a maximum, 29.3% at 4 hours and then decreased; and the content of isomaltose was increased with the decrease of the contents of maltotriose and panose. Further, the contents of isomaltose and oligosaccharides with a glucose polymerization degree of 4 or higher were increased until 48 hours.

From these results, it was revealed that the α-glucosyltransferase of the present invention acts on maltose and forms glucose, maltotriose, and panose by catalyzing both α-1,4 and α-1,6 glucosyl transfer at initial stage of the reaction; and forms isomaltose, which is formed by α-1,6 glucosyl transfer to glucose, and isopanose and isomaltotriose, which are formed by α-1,4 and α-1,6 glucosyl transfer to isomaltose accompanied with the progress of the reaction. Since the identification of many kinds of oligosaccharide with glucose polymerization degree of 4 or higher is difficult in this experiment, the reaction mechanism of the enzyme was investigated in the following Experiment 12-2 using maltopentaose, whose glucose polymerization degree is higher than maltose, as substrate.

Experiment 12-2

Product from Maltopentaose by the Enzyme Reaction

A substrate solution was prepared by mixing an aqueous maltopentaose solution and acetate buffer (pH 6.0) to give final concentrations of 1% (w/v) and 10 mM, respectively. Successively, the resulting substrate solution was admixed with 10 units/g-solid substrate of the α-glucosyltransferase, obtained by the method in Experiment 6, and followed the enzyme reaction at pH 6.0 and 40° C. Time course of the reaction was investigated as follows: Samples of the reaction mixture were withdrawn at various time and kept at 100° C. for 10 min to stop the reaction. Saccharide compositions of the reaction mixtures were determined by HPLC. HPLC analysis was carried out under the conditions described in Experiment 4-2. In addition, the saccharides in the reaction mixture were subjected to the conventional methylation analysis and the partially methylated products were analyzed by gas-chromatography, and the ratio of various glucosidic linkages in the saccharide was determined based on the composition of the partially methylated products. Further, the saccharides in the reaction mixture were subjected to the isomaltodextranase digestion similarly in Experiment 4-2. Time course of the saccharide composition in the reaction mixture is in Table 11. The results of the methylation analysis and the isomaltodextranase digestion are in Table 12.

TABLE 11

| Reaction time (hr) | Saccharide Composition (%, w/w) | | | | | | | | |
|---|---|---|---|---|---|---|---|---|---|
| | DP1 | DP2 | DP3 | DP4 | DP5 | DP6 | DP7 | DP8 | DP9≤ |
| 0 | 0.0 | 0.0 | 0.3 | 1.2 | 97.4 | 0.1 | 0.0 | 0.0 | 0.0 |
| 1 | 0.4 | 1.0 | 3.4 | 15.0 | 53.4 | 21.9 | 3.3 | 0.8 | 0.1 |
| 4 | 1.2 | 2.0 | 7.5 | 15.2 | 27.1 | 25.5 | 12.3 | 5.7 | 3.0 |
| 8 | 2.9 | 3.4 | 8.9 | 12.6 | 18.2 | 20.0 | 14.2 | 8.9 | 9.7 |
| 24 | 6.9 | 3.7 | 8.1 | 8.2 | 12.5 | 14.2 | 13.9 | 11.2 | 21.1 |

DP: Glucose polymerization degree

TABLE 12

| | Composition of partially methylated product (Peak area %) | | | | | | | |
|---|---|---|---|---|---|---|---|---|
| Reaction Time (hr) | 2,3,4,6-Tetra-methylated product Non-reducing end Glc** | 3,4,6-Tri-methylated product Glc involving 1,2-linkage | 2,4,6-Tri-methylated product Glc involving 1,3-linkage | 2,3,6-Tri-methylated product Glc involving 1,4-linkage | 2,3,4-Tri-methylated product Glc involving 1,6-linkage | 2,4-Di-methylated product Glc involving 1,3,6-linkage | 2,3-Di-methylated product Glc involving 1,4,6-linkage | Isomaltose content* (%, w/w) |
| 0 | 20.0 | 0.0 | 0.0 | 80.0 | 0.0 | 0.0 | 0.0 | 0.0 |
| 1 | 20.9 | 0.0 | 0.1 | 76.9 | 1.7 | 0.0 | 0.4 | 2.7 |
| 4 | 24.2 | 0.0 | 0.8 | 67.5 | 7.2 | 0.0 | 0.3 | 11.9 |

TABLE 12-continued

| | Composition of partially methylated product (Peak area %) | | | | | | | |
|---|---|---|---|---|---|---|---|---|
| Reaction Time (hr) | 2,3,4,6-Tetra-methylated product Non-reducing end Glc** | 3,4,6-Tri-methylated product Glc involving 1,2-linkage | 2,4,6-Tri-methylated product Glc involving 1,3-linkage | 2,3,6-Tri-methylated product Glc involving 1,4-linkage | 2,3,4-Tri-methylated product Glc involving 1,6-linkage | 2,4-Di-methylated product Glc involving 1,3,6-linkage | 2,3-Di-methylated product Glc involving 1,4,6-linkage | Isomaltose content* (%, w/w) |
| 8 | 26.1 | 0.0 | 1.0 | 55.4 | 16.1 | 0.7 | 0.8 | 23.3 |
| 24 | 28.6 | 0.0 | 0.8 | 37.0 | 30.8 | 1.6 | 1.2 | 40.9 |

*After isomaltodextranase digestion
**Glucose residue

As is evident from the results in Tables 11 and 12, at initial stage (after one hour) of the reaction, an oligosaccharide whose glucose polymerization degree is larger by one than that of the substrate and that whose glucose polymerization degree is smaller by one than the substrate were formed preferentially. Based on the fact, it was confirmed that the enzyme catalyzes the transglucosylation. Accompanying with the progress of the reaction, reaction products with various glucose polymerization degrees were formed, and the content of glucans with a glucose polymerization degree of 9 or higher reached to 21.1% at 24 hours. From the results of the methylation analysis, it was reveled that accompanying with the progress of the reaction, the content of glucose residue involving 1,4 linkage was decreased with the significant increase of the content of glucose residue involving 1,6 linkage; and the contents of glucose residue involving 1,3 linkage, that involving 1,4,6 linkage, and that involving 1,3,6 linkage were gradually increased in the reaction products. It was also revealed that the isomaltose content after the isomaltodextranase digestion of the reaction product was significantly increased accompanying with the progress of the reaction. Almost the same results were obtained in the case of using the α-glucosyltransferase from *Arthrobacter globiformis* PP349 for the same tests.

From the results in Experiments 12-1 and 12-2, the reaction mechanism of the α-glucosyltransferase of the present invention was estimated as follows:

(1) The enzyme acts on maltose and/or α-1,4 glucan having a glucose polymerization degree of 3 or higher as the substrate and forms the α-1,4 glucan in which a glucose residue is bound via α-linkage to hydroxyl group at C-4 or C-6 position of the non-reducing end glucose residue (α-glucan whose glucose polymerization degree is increased by one) and the α-1,4 glucan whose glucose polymerization degree is decreased by one, by mainly transferring the non-reducing end glucose residue to the non-reducing end glucose residue of the other α-1,4 glucan by α-1,4 or α-1,6 transglucosylation.

(2) The enzyme further acts on the α-1,4 glucan whose glucose polymerization degree is decreased by one, formed in the above step (1); and transfers a glucose residue to the C-4 or C-6 hydroxyl group of the non-reducing end glucose residue of the α-glucan whose glucose polymerization degree is increased by one, also formed in the above step (1), by the intermolecular α-1,4 or α-1,6 transglucosylation to elongate the glucose chain.

(3) By repeating the reactions in the above steps (1) and (2), the enzyme forms a glucan having both α-1,4 and α-1,6 linkages from maltose and/or α-glucan having a glucose polymerization degree of 3 or higher.

(4) Although the frequency is low, the enzyme forms a glucan having α-1,3, α-1,4,6, and α-1,3,6 linkages in addition to α-1,4 and α-1,6 linkages by catalyzing the α-1,3 transglucosylation and α-1,4 or α-1,3 transglucosylation to the internal glucose residues involving α-1,6 linkages, in the glucan.

(5) As results of repeating the reactions in the above steps (1) to (4), the branched α-glucan of the present invention, in which glucose is mainly bound via α-1,4 and α-1,6 linkages and which has α-1,3, α-1,4,6, and α-1,3,6 linkages in a low frequency, is formed by the enzyme.

Experiment 13

α-Glucosyl-Transferring Reaction and the Change of Reducing Power of the Reaction Mixture Substrate solutions were prepared by mixing an aqueous maltose solution and acetate buffer (pH 6.0) to give final concentrations of 1% or 30% (w/v) and 20 mM, respectively. Successively, the resulting substrate solution was admixed with 4 units/g-solid substrate of the purified preparation of the α-glucosyltransferase from *Bacillus circulans* PP710, obtained by the method in Experiment 6, and followed the enzyme reaction at pH 6.0 and 40° C. Time course of the reaction was investigated as follows: Samples of the reaction mixture were withdrawn at various time and kept at 100° C. for 10 min to stop the reaction. The amount of residual maltose in the reaction mixtures were determined by HPLC and GC described in Experiment 4-2. The amounts of reducing saccharide and total saccharide were determined by Somogyi-Nelson method and Anthrone-sulfuric acid method, respectively; and then the reducing power of the reaction mixture was calculated using the following formula:

Reducing power={(The amount of reducing saccharide/The amount of total saccharide)}×100

The results are in Table 13.

TABLE 13

| | Concentration of maltose | | | |
|---|---|---|---|---|
| | 1% (w/w) | | 30% (w/w) | |
| Reaction time (hr) | Amount of residual maltose (%) | Reducing power (Relative %) | Amount of residual maltose (%) | Reducing power (Relative %) |
| 0 | 99.7 | 43.6 (100%) | 99.7 | 43.6 (100%) |
| 4 | 64.2 | 45.0 (103%) | 68.8 | 43.6 (100%) |
| 8 | 43.0 | 46.0 (106%) | 51.8 | 43.6 (100%) |
| 16 | 20.9 | 46.7 (107%) | 28.8 | 43.7 (100%) |

TABLE 13-continued

| | Concentration of maltose | | | |
|---|---|---|---|---|
| | 1% (w/w) | | 30% (w/w) | |
| Reaction time (hr) | Amount of residual maltose (%) | Reducing power (Relative %) | Amount of residual maltose (%) | Reducing power (Relative %) |
| 24 | 8.1 | 47.9 (109%) | 13.3 | 43.8 (101%) |

As is evident from the results in Table 13, when the α-glucosyltransferase of the present invention was allowed to act on maltose, reducing power of the reaction mixture was slightly increased in the case of using the substrate with a relatively low concentration, 1% (w/v), and substantially not increased in the case of using the substrate with a relatively high concentration, 30% (w/v). The fact that the reducing power of the reaction mixture was only slightly increased in the case of the relatively low substrate concentration and the amount of residual maltose was less than 10%, means that the α-glucosyltransferase of the present invention is an enzyme inherently catalyzing the transferring reaction and hardly hydrolyzes the substrate during the reaction. Almost the same results were obtained in the case of using the α-glucosyltransferase from *Arthrobacter globiformis* PP349 for the same tests.

Experiment 14

Comparison of the Purified α-Glucosyltransferase and Crude Enzyme in the Formation of the Branched α-Glucan From the viewpoint of industrial production of the branched α-glucan, the crude enzyme of the α-glucosyltransferase is preferable as far as it can be used for the production because it is not necessary to purify the enzyme. Accordingly, it was investigated whether the branched α-glucan having almost equal characteristics with Glucan A, prepared in Experiment 1-2, can be obtained or not by using the crude enzyme of the α-glucosyltransferase from *Bacillus circulans*. The crude α-glucosyltransferase solution was prepared by the steps of culturing *Bacillus circulans* PP710 by the method in Experiment 1-1, salting out the resulting culture supernatant using ammonium sulfate, and dialyzing the resulting precipitates against 20 mM acetate buffer (pH 4.5). The crude enzyme solution was allowed to act on "PINEDEX #100®", a partial starch hydrolyzate commercialized by Matsutani Chemical Industries Co., Ltd., Hyogo, Japan, and a glucan solution with a concentration of 30% (w/w) was obtained from the partial starch hydrolyzate as substrate in a yield of 88.2%, on a dry solid basis. The resulting branched α-glucan was called as "Glucan C" and subjected to the methylation analysis. The result is in Table 14. The molecular weight distribution and the WSDF content of Glucan C, measured by the methods described in Experiments 3 and 4, are in Table 15. In Tables 14 and 15, the data of the partial starch hydrolyzate used as material and Glucan A prepared by using partially purified α-glucosyltransferase were copied from Tables 3 and 4 as comparative data.

TABLE 14

| | | Composition (Peak area %) | | |
|---|---|---|---|---|
| Partially methylated product | Corresponding Glc** | Partial starch hydrolyzate* (Material) | Glucan A | Glucan C |
| 2,3,4,6-Tetramethylated product | Non-reducing end Glc | 5.8 | 10.1 | 16.0 |
| 3,4,6-Trimethylated product | Glc involving 1,2-linkage | 0.0 | 0.0 | 0.0 |
| 2,4,6-Trimethylated product | Glc involving 1,3-linkage | 0.0 | 1.1 | 3.0 |
| 2,3,6-Trimethylated product | Glc involving 1,4-linkage | 89.8 | 51.5 | 30.0 |
| 2,3,4-Trimethylated product | Glc involving 1,6-linkage | 0.0 | 32.2 | 40.3 |
| 2,4-Dimethylated product | Glc involving 1,3,6-linkage | 0.0 | 0.8 | 4.8 |
| 2,3-Dimethylated product | Glc involving 1,4,6-linkage | 4.4 | 4.5 | 5.8 |

*"PINEDEX ® #100", a partial starch hydrolyzate commercialized by Matsutani Chemical Industries Co., Ltd., Hyogo, Japan.
**Glucose residue
Glucan A: Glucan prepared by using α-glucosyltransferase (partially purified enzyme) from strain PP710
Glucan C: Glucan prepared by using α-glucosyltransferase (crude enzyme) from strain PP7

TABLE 15

| Analytical data | Partial starch hydrolyzate* (Material) | Glucan A | Glucan C |
|---|---|---|---|
| Number average molecular weight (Mn) (Dalton) | 6,680 | 3,840 | 2,840 |
| Weight-average molecular weight (Mw) (Dalton) | 98,890 | 59,000 | 6,220 |
| Mw/Mn | 14.8 | 15.4 | 2.2 |
| Average glucose polymerization degree of peaks | 449 and 6.3 | 384, 22.2, 10.9, and 1 | 26.7 and 1 |
| WSDF content (%) | 0.0 | 42.1 | 75.8 |

*"PINEDEX ® #100", a partial starch hydrolyzate commercialized by Matsutani Chemical Industries Co., Ltd., Hyogo, Japan.
Glucan A: Glucan prepared by using α-glucosyltransferase (partially purified enzyme) from strain PP710
Glucan C: Glucan prepared by using α-glucosyltransferase (crude enzyme) from strain PP710

As shown in Table 14, in the case of Glucan C, prepared by using the crude enzyme preparation of the α-glucosyltransferase from *Bacillus circulans* PP710, the contents of 2,3,4,6-tetramethylated product, corresponding to non-reducing end glucose residue, and 2,3,4-trimethylated product, corresponding to glucose residue involving to α-1,6 linkage, were unexpectedly increased in the methylation analysis in comparison with the case of Glucan A. The results indicate that Glucan C has many non-reducing ends and contains much more α-1,6 linkages than Glucan A. Further, in Glucan C, the content of 2,4-dimethylated product was 4.8%, which is larger than that of Glucan A, 0.8%. The result indicates that glucose residue involving both 1,3 linkage and 1,6 linkage is increased in Glucan C.

As is evident from Table 15, Glucan C showed lower values of number average molecular weight and weight-average molecular weight (lower glucose polymerization degree), and significantly larger WSDF content than Glucan A. These results suggest that another enzyme different from the α-glucosyltransferase is concomitant in the crude enzyme preparation of the α-glucosyltransferase from *Bacillus circulans* PP710, and the concomitant enzyme involves the increase of α-1,6 linkage and glucose residue involving both 1,3 linkage and 1,6 linkage; the lowering the molecular weight; and the increase of the WSDF content.

Experiment 15

Characterization and Purification of the Concomitant Enzyme in the Crude Enzyme Preparation of α-Glucosyltransferase from *Bacillus circulans* PP710

The enzyme, which co-exists in the crude enzyme preparation of α-glucosyltransferase from *Bacillus circulans* PP710 and involves the increase of α-1,6 linkages and glucose residue involving both 1,3 and 1,6 linkages, the lowering of the molecular weight, and the increase of the content of WSDF; was characterized and purified in the following experiments.

Experiment 15-1

Characterization of the Concomitant Enzyme and Assay of the Enzyme Activity

*Bacillus circulans* PP710, FERM BP-10771, was cultivated by the method in Experiment 1-1, and about 3 L of the resulting culture supernatant was salted out using ammonium sulfate. Then, the resulting precipitated was dissolved in water, dialyzed against 20 mM Tris-HCl buffer containing 1 mM $CaCl_2$, and about 40 ml of the resulting dialyzate was collected as a crude enzyme solution. The crude enzyme solution was admixed with 2% (w/v) of soluble starch solution or 2% (w/v) of pullulan solution, and followed by the enzyme reaction at pH 6.0 and 40° C. for 16 hours. After stopping the reaction by heating at 100° C. for 10 min, the reaction mixture was subjected to TLC using "SILICA-GEL™ 60F$_{254}$", a TLC plate (10×20 cm) commercialized by Merck. TLC was carried out using a solvent (n-butanol/pyridine/water, volume ratio of 6:4:1) and two-times ascending method. The products on the plate were detected by visualizing the spots by spraying 20% sulfate-methanol solution and heating at 100° C. for 5 min. By the TLC analyses, it was revealed that maltose and α-1,4 glucan having a glucose polymerization degree of 3 or higher were formed from soluble starch, and slight amounts of isomaltose and panose were formed from pullulan. It was revealed that an amylase which hydrolyzes starch and pullulan was present in the crude enzyme from *Bacillus circulans* PP710, FERM BP-10771, as a concomitant enzyme.

The activity of the concomitant amylase was assayed as follows: A substrate solution is prepared by dissolving "AMYLOSE EX-I", a short chain amylose with average glucose polymerization degree of 17, commercialized by Hayashibara Biochemical Laboratories Inc., Okayama, Japan, into 50 mM acetate buffer (pH 6.0) containing 1 mM $CaCl_2$ to give a final concentration of 1% (w/v). To 2 ml of the substrate solution, 0.2 ml of the enzyme solution is admixed and followed by the enzyme reaction at 35° C. for 30 min. After the reaction, 0.2 ml of the reaction mixture is withdrawn and mixed with 8 ml of 0.02 N sulfuric acid aqueous solution to stop the reaction. After adding 0.2 ml of 0.1 N iodine solution to the resulting solution, the resulting mixture is kept at 25° C. for 15 min and the absorbance at 660 nm of the mixture is measured. Separately, a reaction mixture at zero time-reaction is treated by the same manner and the absorbance at 660 nm of the mixture is measured. By using the both values, the decrease of iodine-stain per minute is calculated. One unit of the amylase activity is defined as the 10-fold amount of enzyme which decreases 10% of the absorbance at 660 nm (iodine-stain), corresponding to 20 mg of short chain amylose, under the above conditions.

Experiment 15-2

Purification of the Concomitant Amylase

The crude enzyme solution, prepared in Experiment 15-1, was subjected to anion-exchange column chromatography using 70 ml of "DEAF-TOYOPEARL™ 650S" gel, a gel commercialized by Tosoh Corporation, Tokyo, Japan. The amylase activity was not adsorbed on "DEAF-TOYOPEARL™ 650S" gel pre-equilibrated with 20 mM Tris-HCl buffer (pH 7.5) containing 1 mM $CaCl_2$ and eluted as non-absorbing fractions. The active fractions were collected, added ammonium sulfate to give a final concentration of 1.5M, and stand at 4° C. for 24 hours. Successively, the enzyme solution was centrifuged to remove insoluble substances and subjected to hydrophobic column chromatography using 1 ml of "RESOURCE™ PHE" gel, a gel commercialized by Pharmacia Biotech. The amylase activity was adsorbed on "RESOURCE™ PHE" gel pre-equilibrated with 20 mM Tris-HCl buffer (pH 7.5) containing 1.5 M ammonium sulfate and 1 mM $CaCl_2$ and when eluted with a linear gradient decreasing from 1.5 M to zero M of ammonium sulfate, the enzyme activity was eluted at about 0.3 M of ammonium sulfate. The active fractions were collected, concentrated, and subjected to gel-filtration column chromatography using 118 ml of "SUPERDEX™ 200pg" gel, a gel commercialized by Pharmacia Biotech. The amylase activity was eluted using 20 mM Tris-HCl buffer (pH 7.5) containing 0.2 M sodium chloride and 1 mM $CaCl_2$. The active fractions were collected and subjected to anion-exchange column chromatography using 1 ml of "RESOURCE™ Q" gel, a gel commercialized by Pharmacia Biotech. The amylase activity was not adsorbed on "RESOURCE™ Q" gel pre-equilibrated with 20 mM Tris-HCl buffer (pH 7.5) containing 1 mM $CaCl_2$ and eluted as non-absorbing fractions. The active fractions were collected as the purified amylase preparation. The amount of enzyme activity, specific activity, and yield of the amylase at each purification step are in Table 16.

TABLE 16

| Purification step | Amylase activity (units) | Specific activity of amylase (units/mg-protein) | Yield (%) |
| --- | --- | --- | --- |
| Dialyzed solution after salting out with ammonium sulfate | 358 | 3.4 | 100 |
| Eluate from ion-exchange column chromatography | 174 | 30.9 | 48.6 |
| Eluate from hydrophobic column chromatography | 56.8 | 42.5 | 15.9 |

TABLE 16-continued

| Purification step | Amylase activity (units) | Specific activity of amylase (units/mg-protein) | Yield (%) |
|---|---|---|---|
| Eluate from gel-filtration column chromatography | 34.4 | 51.8 | 9.6 |
| Eluate from ion-exchange column chromatography | 32.8 | 52.6 | 9.2 |

The finally purified enzyme preparation of the amylase was assayed for purity on gel electrophoresis using a 5-20% (w/v) gradient polyacrylamide gel and detected on the gel as a single protein band, i.e., a high purity preparation.

Experiment 16

Properties of the Amylase from *Bacillus circulans* PP710

Experiment 16-1

Molecular Weight

The purified enzyme preparation of the amylase, obtained by the method in Experiment 15-2, was subjected to SDS-PAGE (a 5 to 20% (w/v) gradient gel) and the molecular weight of the enzyme was measured comparing with molecular weight markers, commercialized by Bio-Rad Japan, Tokyo, Japan. It was revealed that the amylase has a molecular weight of 58,000±10,000 daltons.

Experiment 16-2

Optimum Temperature and pH of the Amylase

Figure 11:
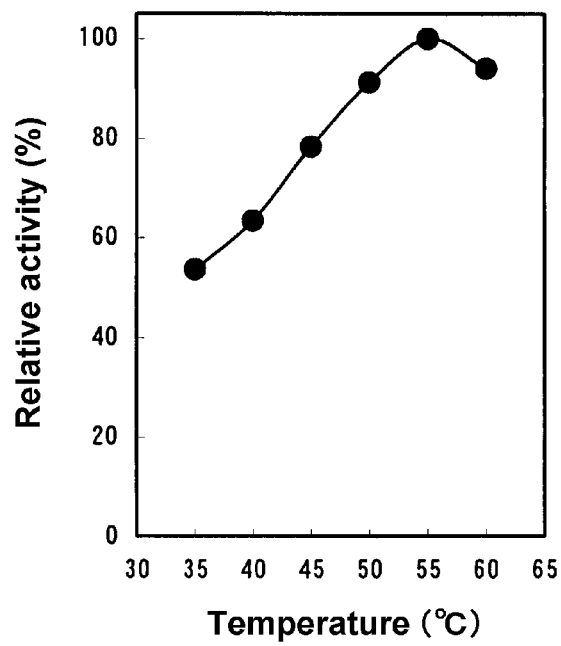
FIG. 11 shows the optimum temperature of amylase from *Bacillus circulans* PP710.
Figure 12:
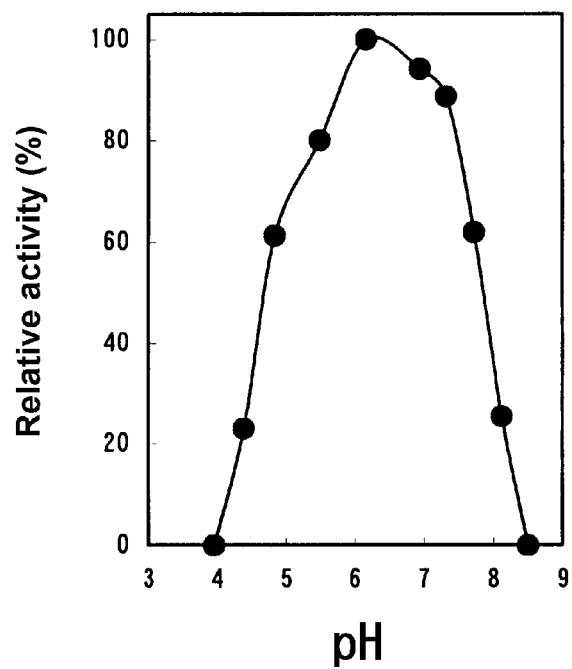
FIG. 12 shows the optimum pH of amylase from *Bacillus circulans* PP710.

Effects of temperature and pH on the enzyme activity were investigated using the purified enzyme preparation of the amylase from *Bacillus circulans* PP710, obtained by the method in Experiment 15-2, by varying temperature and pH at the assay of the enzyme. The results are in FIG. 11 (Optimum temperature) and FIG. 12 (Optimum pH), respectively. It was revealed that the optimum temperature of the amylase was about 55° C. when reacted at pH 6.0 for 30 min and the optimum pH was 6.0 to 7.0 when reacted at 35° C. for 30 min.

Experiment 16-3

Thermal and pH Stabilities of the Amylase

Figure 14:
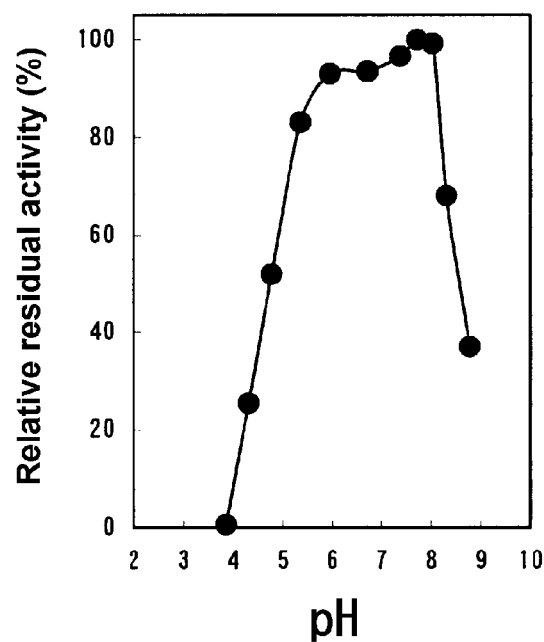
FIG. 14 shows the pH stability of amylase from *Bacillus circulans* PP710.

Thermal stability and pH stability of the enzyme were investigated using the purified enzyme preparation of the amylase, obtained by the method in Experiment 15-2. Thermal stability of the enzyme was determined by the steps of incubating an enzyme solution (20 mM acetate buffer, pH 6.0, or the same buffer containing 1 mM $CaCl_2$) under various temperatures for 60 min, cooling in water, and measuring the residual enzyme activity. pH Stability of the enzyme was determined by the steps of incubating enzyme solution in 20 mM buffer at various pHs, and at 4° C. for 24 hours, adjusting the pH to 6.0, and measuring the residual enzyme activity. The results are in FIG. 13 (Thermal stability) and in FIG. 14 (pH Stability), respectively. As is evident from the results in FIGS. 13 and 14, the amylase is stable up to 40° C. in the absence of calcium ion and up to 50° C. in the presence of 1 mM calcium ion, and stable in the range of pH 6.0 to 8.0.

Experiment 16-5

Substrate Specificity of the Amylase

The action of the amylase to various substrates was investigated using the purified preparation of the amylase, obtained by the method in Experiment 15-2. As a result, it was revealed that the amylase hydrolyze starch, maltose, and α-1,4 glucan having a glucose polymerization degree of 3 or higher, and also catalyzes the transglycosylation. It was also revealed that the amylase forms cyclodextrins from starch and forms panose by hydrolyzing pullulan.

Experiment 17

Figure 15:
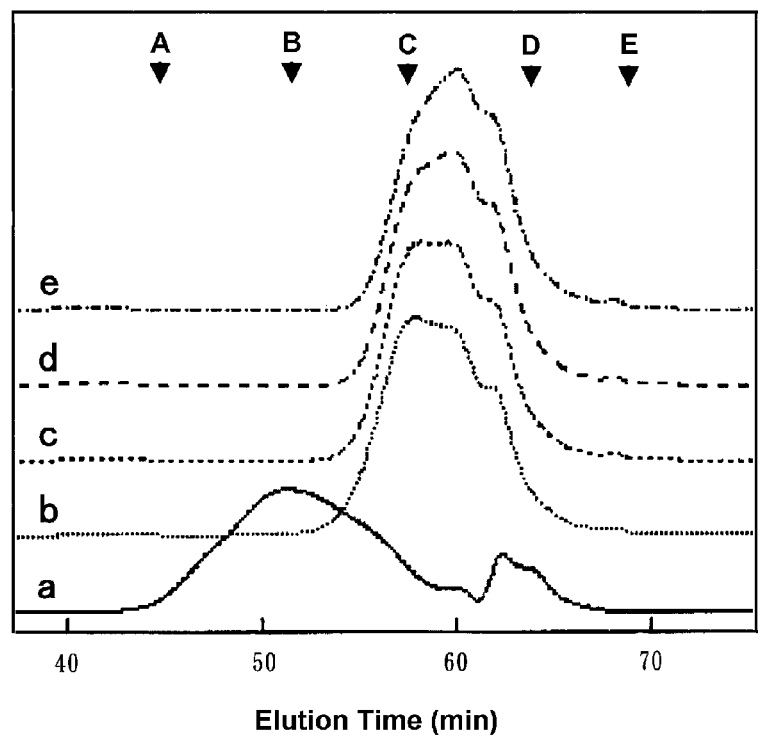
FIG. 15 shows the comparison of gel-filtration HPLC chromatograms of the branched α-glucan, prepared by using purified preparations of α-glucosyltransferase and amylase from *Bacillus circulans* PP710 in combination, and that of partial starch hydrolyzate used as substrate for the enzymes.

Preparation of the Branched α-Glucan by Using α-Glucosyltransferase and the Amylase in Combination Using the purified preparation of the α-glucosyltransferase from *Bacillus circulans* PP710, obtained by the method in Experiment 6, and the purified preparation of the amylase, obtained by the method in Experiment 15-2, it was investigated whether Glucan C in Experiment 14, which was produced by using the crude enzyme preparation of α-glucosyltransferase from *Bacillus circulans* PP710, can be re-produced or not. "PINEDEX® #100", a partial starch hydrolyzate commercialized by Matsutani Chemical Industries Co., Ltd., Hyogo, Japan, was dissolved in water to give a concentration of 30% (w/w) and the pH of the solution was adjusted to 6.0. To the substrate solution, 10 units/g-solid of the purified preparation of the α-glucosyltransferase from *Bacillus criculans* PP710, obtained by the method in Experiment 6; and zero, 0.1, 0.2, 0.5 or 1.0 unit/g-solid of the amylase obtained by the method in 15-2 were added, and followed by the enzyme reaction at pH 6.0 and 40° C. for 72 hours. After completion of the reaction, the reaction mixture was boiled for 10 min to stop the reaction. The reaction mixtures containing the branched α-glucan, obtained by respective reaction condition, were subjected to gel-filtration HPLC described in Experiment 4-4, and the chromatograms are shown in FIG. 15 together with that of the partial starch hydrolyzate used as a substrate. In FIG. 15, symbol "a" is the gel-filtration HPLC chromatogram of partial starch hydrolyzate used as a substrate, and symbols "b", "c", "d", and "e" are those of the branched α-glucans obtained by using 10 units/g-solid of the α-glucosyltransferase and 0.1, 0.2, 0.5, or 1.0 unit/g-solid of the amylase, respectively. (Since the gel-filtration HPLC chromatogram of the branched α-glucan, obtained by using 10 units/g-solid of the α-glucosyltransferase only, is almost same with that of Glucan A in FIG. 1, it is omitted in FIG. 15, and also in the following FIGS. 16 to 19.) The results of the molecular weight distribution analyses based on those gel-filtration HPLC chromatograms and the WSDF content measured by the Enzyme-HPLC method in Experiment 3 of the branched α-glucans are in Table 17. Those of the partial starch hydrolyzate used as a substrate (zero unit/g-solid of α-glucosyltransferase, and zero unit of amylase) are also in Table 17.

TABLE 17

| Amount of enzyme (unit/g-substrate) | | Molecular weight distribution of glucan | | | |
|---|---|---|---|---|---|
| α-Glucosyl tansferase | Amylase | Number average molecular weight (Mn) (Dalton) | Weight-average molecular weight (Mw) (Dalton) | Mw/Mn | WSDF content (%, w/w) |
| 0 | 0.0 | 6,670 | 100,340 | 15.0 | 0.0 |
| 10 | 0.0 | 5,530 | 97,450 | 17.6 | 41.1 |
| 10 | 0.1 | 3,235 | 7,799 | 2.4 | 71.5 |
| 10 | 0.2 | 3,013 | 6,627 | 2.2 | 73.7 |
| 10 | 0.5 | 2,789 | 5,894 | 2.1 | 76.7 |
| 10 | 1.0 | 2,544 | 5,304 | 2.1 | 76.8 |

As is evident from the results in Table 17, in the case of using the α-glucosyltransferase and the amylase in combination, the molecular weight of the formed branched α-glucan was decreased and the WSDF content was significantly increased. The number average molecular weight, the weight-average molecular weight, and the value of dividing the weight-average molecular weight with the number average molecular weight, Mw/Mn, of the branched α-glucan were decreased with increase of the amount of the amylase. From the results, it was revealed that the range of the molecular weight distribution of the branched α-glucan became narrower with increase of the amount of the amylase. In the case of using 0.5 unit/g-solid of the amylase, the value of Mw/Mn was decreased to 2.1. Further, in the cases of using 0.5 unit/g-solid or higher of the amylase, the WSDF contents of the branched α-glucan were reached to about 76% (w/w).

From the results, it was confirmed that the decrease of the molecular weight and the increase of the WSDF content in Glucan C, obtained in Experiment 14 by using the crude enzyme preparation of the α-glucosyltransferase from *Bacillus circulans* PP710, were caused by the concomitant amylase in the crude enzyme preparation. It is considered that the concomitant amylase partially hydrolyzed the partial starch hydrolyzate as a substrate and the branched α-glucan as a product by the α-glucosyltransferase to decrease the molecular weight; and acts for increasing the WSDF content by transferring glycosyl group to the branched α-glucan. Further, the results indicate that the branched α-glucan, having a low molecular weight and a high WSDF content, can be produced by using the amylase and the α-glucosyltransferase of the present invention in combination.

Experiment 18

Preparations of the Branched α-Glucan by Using the α-Glucosyltransferase and Other Well-Known Amylases in Combination Various branched α-glucans were prepared by allowing the α-glucosyltransferase of the present invention and other well-known amylases to act in combination on the partial starch hydrolyzate, and the characteristics and the WSDF contents of the resulting branched α-glucan were investigated. Almost equal results were obtained in the cases of using the α-glucosyltransferase from *Bacillus circulans* PP710 and from *Arthrobacter globiformis* PP349. Therefore, in this experiment, the results obtained by using the α-glucosyltransferase from *Bacillus circulans* PP710 were described.

Experiment 18-1

Figure 16:
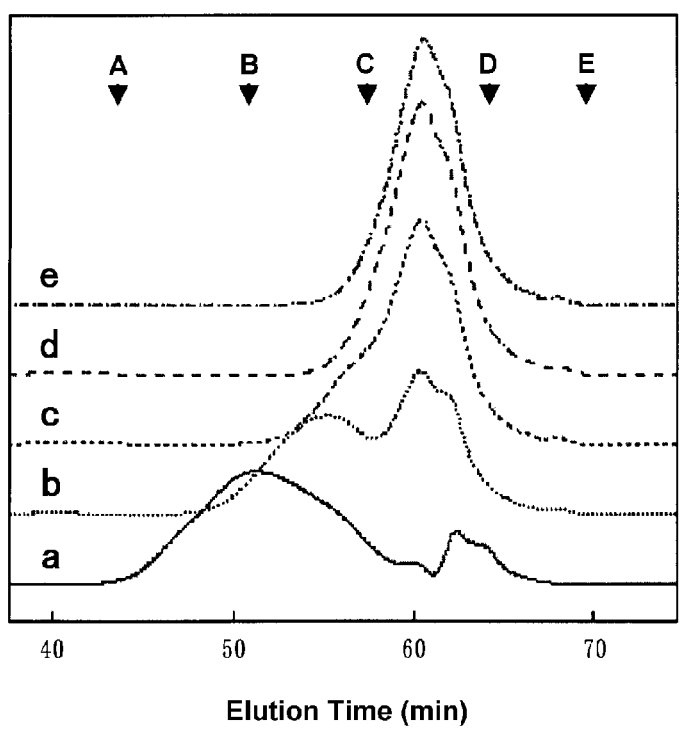
FIG. 16 shows the comparison of gel-filtration HPLC chromatograms of the branched α-glucan, prepared by using purified preparations of α-glucosyltransferase from *Bacillus circulans* PP710 and isoamylase in combination, and that of partial starch hydrolyzate used as substrate for the enzymes.

Preparation of the Branched α-Glucan by Using α-Glucosyltransferase and Isoamylase in Combination; and Molecular Weight Distribution and the WSDF Content of the Resulting Branched α-Glucan Except for using zero, 50,200, 500, or 1,000 units/g-solid of isoamylase from *Pseudomonas amyloderamosa*, prepared by Hayashibara Biochemical Laboratories Inc., Okayama, Japan, as a substitute of the amylase from *Bacillus circulans* PP710, the branched α-glucan was prepared according to the method in Experiment 17. Each branched α-glucan, prepared by each reaction condition, was subjected to the gel-filtration HPLC in Experiment 4-4, and the chromatogram was shown in FIG. 16 together with that of the partial starch hydrolyzate used as substrate. In FIG. 16, symbol "a" is a gel-filtration HPLC chromatogram of the partial starch hydrolyzate used as substrate, and symbols "b", "c", "d", and "e" are gel-filtration HPLC chromatograms of the branched α-glucans obtained by using 10 units/g-solid of the α-glucosyltransferase, and 50, 200, 500, and 1,000 units/g-solid of isoamylase in combination, respectively. The results of the molecular weight distribution analyses based on the gel-filtration HPLC chromatograms and the WSDF contents determined by Enzyme-HPLC method in Experiment 3 are in Table 18.

TABLE 18

| Amount of enzyme (unit/g-substrate) | | Molecular weight distribution of glucan | | | |
|---|---|---|---|---|---|
| α-Glucosyl tansferase | Isoamylase | Number average molecular weight (Mn) (Dalton) | Weight-average molecular weight (Mw) (Dalton) | Mw/Mn | WSDF content (%, w/w) |
| 0 | 0 | 6,670 | 100,340 | 15.0 | 0.0 |
| 10 | 0 | 5,530 | 97,450 | 17.6 | 41.1 |
| 10 | 50 | 3,490 | 19,980 | 5.7 | 40.6 |
| 10 | 200 | 2,560 | 6,580 | 2.6 | 42.7 |
| 10 | 500 | 2,230 | 4,340 | 1.9 | 43.7 |
| 10 | 1,000 | 2,140 | 4,020 | 1.9 | 41.6 |

As is evident from the result in the case of allowing the α-glucosyltransferase only to act on the partial starch hydrolyzate in Table 18, the α-glucosyltransferase did not exercise an influence on the molecular weight distribution of the branched α-glucan. However, as is evident from the results in Table 18 and FIG. 16, both the number average molecular weight and the weight-average molecular weight, and Mw/Mn, the value of dividing the weight-average molecular weight with the number average molecular weight were decreased with increase of the amount of isoamylase. From the results, it was revealed that the range of the molecular weight distribution of the branched α-glucan became narrower by the action of isoamylase. In the case of using 1,000 units/g-solid of isoamylase, Mw/Mn of the branched α-glucan was decreased to 1.9 and the branched α-glucan showed a molecular weight distribution with a peak at glucose polymerization degree of 20.2. While, the WSDF contents of the branched α-glucans, obtained by the reaction conditions, were not influenced by the amount of isoamylase and were about 40 to 44% (w/w).

From these results, it was revealed that the branched α-glucan with a low molecular weight can be produced without altering the WSDF content by allowing the α-glucosyltransferase of the present invention and isoamylase to act in combination on the partial starch hydrolyzate.

Experiment 18-2

Figure 17:
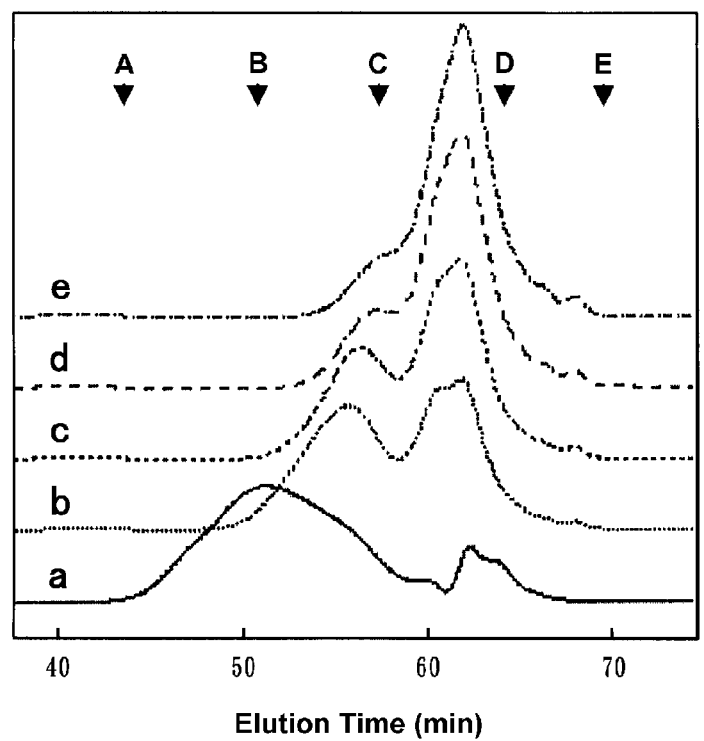
FIG. 17 shows the comparison of gel-filtration HPLC chromatograms of the branched α-glucan, prepared by using purified preparations of α-glucosyltransferase from *Bacillus circulans* PP710 and α-amylase in combination, and that of partial starch hydrolyzate used as substrate for the enzymes.

Preparation of the Branched α-Glucan by Using α-Glucosyltransferase and α-Amylase in Combination; and Molecular Weight Distribution and the WSDF Content of the Resulting Branched α-Glucan Except for using zero, 0.1, 0.2, 0.5, or 1.0 unit/g-solid of "NEOSPITASE PK2", an α-amylase commercialized by Nagase ChemteX Corporation, Osaka, Japan, as a substitute of isoamylase from *Pseudomonas amyloderamosa*, the branched α-glucan was prepared according to the method in Experiment 18-1. Each branched α-glucan, prepared by each reaction condition, was subjected to the gel-filtration HPLC in Experiment 4-4, and the chromatogram was shown in FIG. 17 together with that of the partial starch hydrolyzate used as substrate. In FIG. 17, symbol "a" is a gel-filtration HPLC chromatogram of the partial starch hydrolyzate used as substrate, and symbols "b", "c", "d", and "e" are gel-filtration HPLC chromatograms of the branched α-glucans obtained by using 10 units/g-solid of the α-glucosyltransferase, and 0.1, 0.2, 0.5, and 1.0 unit/g-solid of α-amylase in combination, respectively. The results of the molecular weight distribution analyses based on the gel-filtration HPLC chromatograms and the WSDF contents determined by Enzyme-HPLC method in Experiment 3 are in Table 19.

TABLE 19

| Amount of enzyme (unit/g-substrate) | | Molecular weight distribution of glucan | | | |
|---|---|---|---|---|---|
| α-Glucosyl tansferase | α-Amylase | Number average molecular weight (Mn) (Dalton) | Weight-average molecular weight (Mw) (Dalton) | Mw/Mn | WSDF content (%, w/w) |
| 0 | 0.0 | 6,670 | 100,340 | 15.0 | 0.0 |
| 10 | 0.0 | 5,530 | 97,450 | 17.6 | 41.1 |
| 10 | 0.1 | 2,835 | 15,698 | 5.5 | 48.4 |
| 10 | 0.2 | 2,189 | 8,656 | 4.0 | 51.7 |
| 10 | 0.5 | 1,694 | 4,755 | 2.8 | 53.5 |
| 10 | 1.0 | 1,475 | 3,552 | 2.4 | 54.0 |

As is evident from the results in FIG. 17 and Table 19, both the number average molecular weight and the weight-average molecular weight, and Mw/Mn, the value of dividing the weight-average molecular weight with the number average molecular weight were decreased with increase of the amount of α-amylase. From the results, it was revealed that the range of the molecular weight distribution of the branched α-glucan became narrower by the action of α-amylase. In the case of using 1.0 unit/g-solid of α-amylase (Symbol "e" in FIG. 17), Mw/Mn of the branched α-glucan was decreased to 2.4 and the branched α-glucan showed a molecular weight distribution with a peak at glucose polymerization degree of 11.8. While, the WSDF contents of the branched α-glucans, obtained by the reaction conditions, showed a tendency of increasing with increase of the amount of α-amylase.

From these results, it was revealed that the branched α-glucan with a low molecular weight and increased WSDF content can be produced by allowing the α-glucosyltransferase of the present invention and α-amylase to act in combination on the partial starch hydrolyzate.

Experiment 18-3

Figure 18:
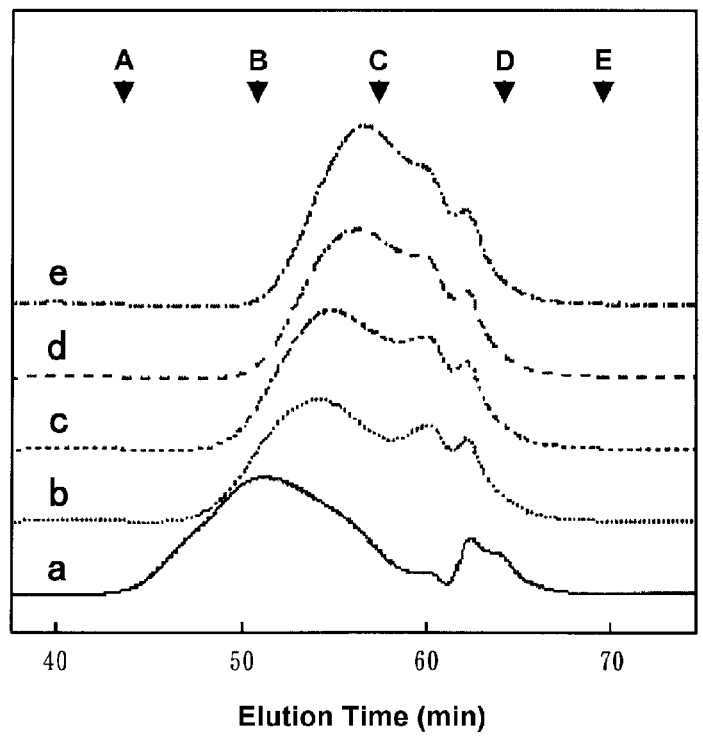
FIG. 18 shows the comparison of gel-filtration HPLC chromatograms of the branched α-glucan, prepared by using purified preparations of α-glucosyltransferase and from *Bacillus circulans* PP710 and CGTase in combination, and that of partial starch hydrolyzate used as substrate for the enzymes.

Preparation of the Branched α-Glucan by Using α-Glucosyltransferase and CGTase in Combination; and Molecular Weight Distribution and the WSDF Content of the Resulting Branched α-Glucan Except for using zero, 0.1, 0.2, 0.5, or 1.0 unit/g-solid of CGTase from *Bacillus stearothermophilus*, produced by Hayashibara Biochemical Laboratories Inc., Okayama, Japan, as a substitute of isoamylase from *Pseudomonas amyloderamosa*, the branched α-glucan was prepared according to the method in Experiment 18-1. Each branched α-glucan, prepared by each reaction condition, was subjected to the gel-filtration HPLC in Experiment 4-4, and the chromatogram was shown in FIG. 18 together with that of the partial starch hydrolyzate used as substrate. In FIG. 18, symbol "a" is a gel-filtration HPLC chromatogram of the partial starch hydrolyzate used as substrate, and symbols "b", "c", "d", and "e" are gel-filtration HPLC chromatograms of the branched α-glucans obtained by using 10 units/g-solid of the α-glucosyltransferase, and 0.1, 0.2, 0.5, and 1.0 unit/g-solid of CGTase in combination, respectively. The results of the molecular weight distribution analyses based on the gel-filtration HPLC chromatograms and the WSDF contents determined by Enzyme-HPLC method in Experiment 3 are in Table 20.

TABLE 20

| Amount of enzyme (unit/g-substrate) | | Molecular weight distribution of glucan | | | |
|---|---|---|---|---|---|
| α-Glucosyl tansferase | CGTase | Number average molecular weight (Mn) (Dalton) | Weight-average molecular weight (Mw) (Dalton) | Mw/Mn | WSDF content (%, w/w) |
| 0 | 0.0 | 6,670 | 100,340 | 15.0 | 0.0 |
| 10 | 0.0 | 5,530 | 97,450 | 17.6 | 39.1 |
| 10 | 0.1 | 4,733 | 32,833 | 6.9 | 57.5 |
| 10 | 0.2 | 4,733 | 23,418 | 4.9 | 62.8 |
| 10 | 0.5 | 4,501 | 16,357 | 3.6 | 68.2 |
| 10 | 1.0 | 4,401 | 14,107 | 3.2 | 70.5 |

CGTase: Cyclomaltodextrin glucanotransferase

As is evident from the results in FIG. 18 and Table 20, both the number average molecular weight and the weight-average molecular weight, and Mw/Mn, the value of dividing the weight-average molecular weight with the number average molecular weight were decreased with increase of the amount of CGTase. From the results, it was revealed that the range of the molecular weight distribution of the branched α-glucan became narrower by the action of CGTase. In the case of using 1.0 unit/g-solid of CGTase (Symbol "e" in FIG. 18), Mw/Mn of the branched α-glucan was decreased to 3.2 and the branched α-glucan showed a molecular weight distribution with a peak at glucose polymerization degree of 79.1. While, the WSDF contents of the branched α-glucans, obtained by the reaction conditions, showed a tendency of increasing with increase of the amount of CGTase. The WSDF content of the branched α-glucan, obtained by using CGTase in combination, was significantly increased in comparison with the case of using α-amylase in Experiment 18-2. In the case of using 1.0 unit/g-solid of CGTase, the WSDF content of the branched α-glucan was reached to 70.5% (w/w).

From these results, it was revealed that the branched α-glucan with a low molecular weight and significantly increased WSDF content can be produced by allowing the α-glucosyltransferase of the present invention and CGTase to act in combination on the partial starch hydrolyzate. Since CGTase is an enzyme catalyzing the hydrolysis of α-1,4 linkage and also the glycosyl-transfer, it forms many non-reducing end glucose residues in the branched α-glucan without significantly lowering the molecular weight in comparison with the case of using α-amylase. Therefore, it is suggested that the α-glucosyltransferase is able to act more frequently on the branched α-glucan formed by using CGTase than that formed by using α-amylase, and as a result, the branched α-glucan with increased WSDF content can be obtained.

Experiment 18-4

Figure 19:
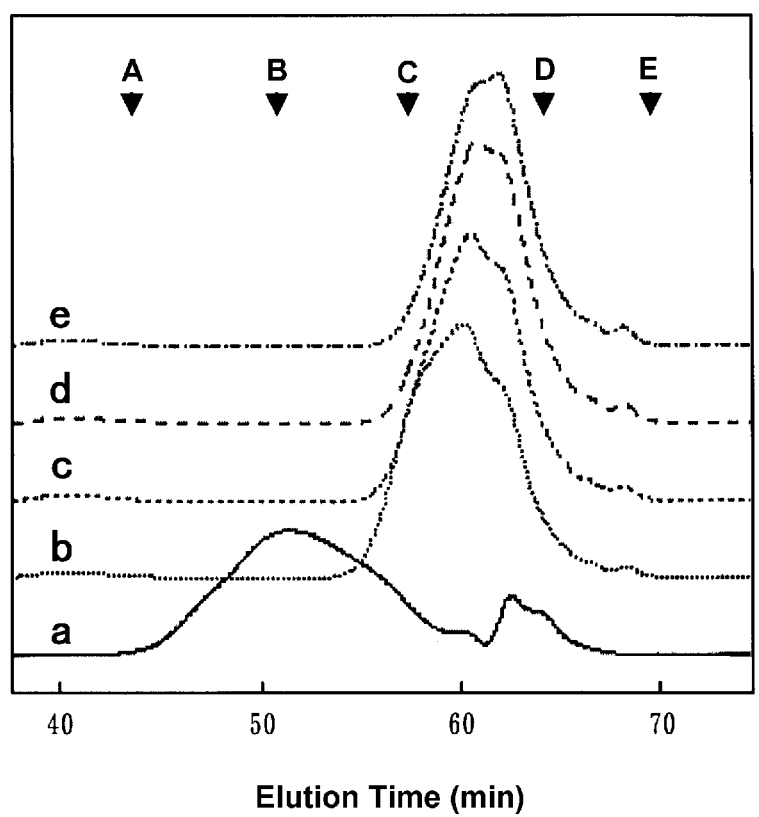
FIG. 19 shows the comparison of gel-filtration HPLC chromatograms of the branched α-glucan, prepared by using purified preparations of α-glucosyltransferase from *Bacillus circulans* PP710, isoamylase, and CGTase in combination, and that of partial starch hydrolyzate used as substrate for the enzymes.

Preparation of the Branched α-Glucan by Using α-Glucosyltransferase, Isomalyase, and CGTase in Combination; and Molecular Weight Distribution and the WSDF Content of the Resulting Branched α-Glucan Except for further adding zero or 1.0 unit/g-solid of CGTase from *Bacillus stearothermophilus* to the reaction system in Experiment 18-1, the branched α-glucan was prepared according to the method in Experiment 18-1. Each branched α-glucan, prepared by each reaction condition, was subjected to the gel-filtration HPLC in Experiment 4-4, and the chromatogram was shown in FIG. 19 together with that of the partial starch hydrolyzate used as substrate. In FIG. 19, symbol "a" is a gel-filtration HPLC chromatogram of the partial starch hydrolyzate used as substrate, and symbols "b", "c", "d", and "e" are gel-filtration HPLC chromatograms of the branched α-glucans obtained by using 10 units/g-solid and 1.0 unit/g-solid of the α-glucosyltransferase and CGTase, respectively, and 50, 200, 500, and 1,000 units/g-solid of isoamylase in combination, respectively. The results of the molecular weight distribution analyses based on the gel-filtration HPLC chromatograms and the WSDF contents determined by Enzyme-HPLC method in Experiment 3 are in Table 21.

ferase of the present invention and 1.0 unit/g-solid of CGTase in combination, was decreased to 3.2. In the case of adding 1,000 units/g-solid of isoamylase to the reaction system (Symbol "e" in FIG. 19), Mw/Mn was further decreased to 1.9. The WSDF content in the branched α-glucan, prepared by using the α-glucosyltransferase of the present invention and CGTase in combination, was increased to about 70% (w/w), and the contents were kept the relatively high values by adding isoamylase to the reaction systems.

From these results, it was revealed that the branched α-glucan with a significantly lowered molecular weight and significantly increased WSDF content can be produced by allowing the α-glucosyltransferase of the present invention, isoamylase, and CGTase to act in combination on the partial starch hydrolyzate.

Experiment 19

Functions of the Branched α-Glucan

The branched α-glucan, prepared in Experiment 18-4 by using 10 units/g-solid of the α-glucosyltransferase, 50 units/g-solid of isoamylase, and 1.0 unit/g-solid of CGTase in combination, was selected as the branched α-glucan with the highest WSDF content and a relatively low molecular weight; and the digestibility, structural characteristics, and functions of the branched α-glucan was investigated.

Experiment 19-1

Purification of the Branched α-Glucan Prepared by Using α-Glucosyltransferase, Isomalyase, and CGTase in Combination A reaction mixture containing the branched α-glucan was prepared by the same reaction in Experiment 18-4 using 10 units/g-solid of the α-glucosyltransferase, 50 units/g-solid of isoamylase, and 1.0 unit/g-solid of CGTase in combination. After removing insoluble substances from the reaction mixture by filtration, the resulting filtrate was decolored and deionized using "DIAION™ SK-1B" and "DIAION™ WA30", both ion-exchange resins commercialized by Mitsubishi Chemical Corporation, Tokyo, Japan, and "IRA 411", an anion exchange resin commercialized by Organo Corporation, Tokyo, Japan; and then filtrated using a membrane and concentrated using an evaporator. By the above procedure, an

TABLE 21

| Amount of enzyme (unit/g-substrate) | | | Molecular weight distribution of glucan | | | WSDF |
|---|---|---|---|---|---|---|
| α-Glucosyl tansferase | Isoamylase | CGTase | Number average molecular weight (Mn) (Dalton) | Weight-average molecular weight (Mw) (Dalton) | Mw/Mn | content (%, w/w) |
| 0 | 0 | 0.0 | 6,670 | 100,340 | 15.0 | 0.0 |
| 10 | 0 | 0.0 | 5,530 | 97,450 | 17.6 | 41.1 |
| 10 | 0 | 1.0 | 4,401 | 14,107 | 3.2 | 70.5 |
| 10 | 50 | 1.0 | 2,423 | 5,445 | 2.2 | 74.0 |
| 10 | 200 | 1.0 | 1,956 | 4,021 | 2.1 | 73.8 |
| 10 | 500 | 1.0 | 1,705 | 3,367 | 2.0 | 72.3 |
| 10 | 1000 | 1.0 | 1,601 | 3,086 | 1.9 | 70.6 |

CGTase: Cyclomaltodextrin glucanotransferase

As is evident from the results in FIG. 19 and Table 21, Mw/Mn, the value of dividing the weight-average molecular weight with the number average molecular weight of the branched α-glucan, prepared by using the α-glucosyltransaqueous solution, containing the branched α-glucan, with a concentration of 30% was obtained in a yield of 85.8%, on a dry solid basis, from the material starch. According to the method in Experiment 4-2, the methylation analysis of the resulting branched α-glucan was carried out and the result is shown in Table 22. In addition, the result of the molecular weight distribution analysis, obtained by the gel-filtration HPLC described in Experiment 4-1, the WSDF contents, measured by the Enzyme-HPLC method described in Experiment 3, and the result of isomaltodextranase digestion, obtained by the method described in Experiment 4-2, of the branched α-glucan are summarized in Table 23.

TABLE 22

| Partially methylated product | Corresponding Glc** | Composition (Peak area %) |
|---|---|---|
| 2,3,4,6-Tetramethylated product | Non-reducing end Glc | 13.7 |
| 3,4,6-Trimethylated product | Glc involving 1,2-linkage | 0 |
| 2,4,6-Trimethylated product | Glc involving 1,3-linkage | 1.6 |
| 2,3,6-Trimethylated product | Glc involving 1,4-linkage | 22.8 |
| 2,3,4-Trimethylated product | Glc involving 1,6-linkage | 54.7 |
| 2,4-Dimethylated product | Glc involving 1,3,6-linkage | 2.4 |
| 2,3-Dimethylated product | Glc involving 1,4,6-linkage | 4.8 |

*Glucose residue

TABLE 23

| Molecular weight distribution | | | | Isomaltose |
|---|---|---|---|---|
| Number average molecular weight (Mn) (Dalton) | Weight-average molecular weight (Mw) (Dalton) | Mw/Mn | WSDF content (%, w/w) | content after isomalto-dextranase digestion (%, w/w) |
| 2,400 | 5,480 | 2.3 | 68.6 | 36.4 |

As is evident from the results in Table 22 and 23, in the methylation analysis of the branched α-glucan, the partially methylated products comprised 2,3,6-trimethylated product and 2,3,4-trimethylated product in a ratio of 1:2.4, and the total content of 2,3,6-trimethylated product and 2,3,4-trimethylated product was 77.5%. The contents of 2,4,6-trimethylated product and 2,4-dimethylated product were 1.6% and 2.4%, respectively, in the partially methylated products. The branched α-glucan showed the weight-average molecular weight of 5,480 daltons and Mw/Mn of 2.3. The WSDF content of the branched α-glucan, measured by the Enzyme-HPLC method, was 68.6%. From the branched α-glucan, 36.4% (w/w) of isomaltose was formed by the isomaltodextranase digestion.

In order to evaluate the usefulness of the branched α-glucan of the present invention, cariogenicity, digestibility, effects on blood-sugar level and insulin level, and acute toxicity of the branched α-glucan were investigated in the following Experiment 19-2 to 19-7 using the branched α-glucan prepared in Experiment 19-1.

Experiment 19-2

Acid-Fermentation Test of the Branched α-Glucan Using Cariogenic Bacteria

According to the method of Ohshima et al. described in Infection and Immunity, vol. 39, pp. 43-49 (1983), an acid-fermentation test of the branched α-glucan, obtained in Experiment 19-1, was carried out using cariogenic bacteria. Two bacterial strains, *Streptococcus sobrinus* 6715 and *Streptococcus mutans* OMZ-176, were used as cariogenic bacteria. Sucrose was used as a control saccharide, and tested by the same method. The results are in Table 24.

TABLE 24

| | pH | | | |
|---|---|---|---|---|
| | S. sobrinus | | S. mutans | |
| Time (min) | Sucrose (Control) | Branched α-glucan (Present invention) | Sucrose (Control) | Branched α-glucan (Present invention) |
| 0 | 6.7 | 6.7 | 6.8 | 6.8 |
| 5 | 4.3 | 5.9 | 6.0 | 6.1 |
| 15 | 4.0 | 6.1 | 4.6 | 6.2 |
| 30 | 3.9 | 6.1 | 4.4 | 6.2 |
| 60 | 3.9 | 6.1 | 4.3 | 6.1 |
| 90 | 4.0 | 6.1 | 4.2 | 6.1 |

As is evident from the results in Table 24, in the case of sucrose, the pHs of the culture broth inoculated with the cariogenic bacteria were lowered by the acid-formation. While, in the case of the branched α-glucan of the present invention, the saccharide was not fermented to form acids by *Streptococcus sobrinus* and *Streptococcus mutans*, and the pHs of the culture broth were kept to about 6. The pH is higher than 5.5 which is critical pH of decalcifying enamel of tooth. From the results, it was confirmed that the branched α-glucan of the present invention shows a significantly low cariogenicity.

Experiment 19-3

Digestibility of the Branched α-Glucan

According to the method of Okada et al., described in Journal of Japanese Society of Nutrition and Food Sciences, vol. 43, pp. 23-29 (1990), the digestibility of the branched α-glucan by salivary α-amylase, artificial gastric juice, pancreas amylase, and small intestinal enzymes were investigated in vitro using the branched α-glucan, obtained in Experiment 19-1. "PINEFIBER®", a low-digestible dextrin commercialized by Matsutani Chemical Industries Co., Ltd., Hyogo, Japan, was used as a control. The results are in Table 25.

TABLE 25

| | Digestion (%) | |
|---|---|---|
| Digestive enzyme | Branched α-glucan (Present invention) | Low-digestible dextrin (Control) |
| Salivary amylase | 0.0 | 0.3 |
| Artificial gastric juice | 0.0 | 0.0 |
| Pancreas amylase | 0.2 | 2.4 |
| Small intestinal enzymes | 16.4 | 41.1 |

As is evident from the results in Table 25, the branched α-glucan of the present invention was not digested by either of salivary amylase, and artificial gastric juice, and slightly digested by pancreas amylase. The digestion (%) of the branched α-glucan by small intestinal enzymes was 16.4% and much lower than 41.4%, that of the low-digestible dextrin used as a control. It was revealed that the digestibility of the branched α-glucan of the present invention is much lower than the commercially available low-digestible dextrin.

Experiment 19-4

Effects of the Ingestion of the Branched α-Glucan on Blood-Sugar Level and Insulin Level Effects of the branched α-glucan on the elevation of blood-sugar level and insulin level were investigated using the branched α-glucan obtained by the method in Experiment 19-1. Five male Wister rats (seven weeks old)/group were preliminary fasted for one day, and then an aqueous solution containing the branched α-glucan was orally administrated to the rats using a gastric sonde. The dose was set to 1.5 g-solid/kg-rat weight. Blood samples were withdrawn from the caudal vein of rats at just before administration, 15 min-after, 30 min-after, 60 min-after, and 120 min-after from the administration. Each blood sample was collected in a heparin-treated tube and then centrifuged at 2,000 rpm for 10 min to obtain blood plasma. Blood-sugar level in the blood plasma was measured by the glucose oxidase-peroxidase method, and insulin level was measured using a kit for measuring rat insulin, commercialized by Morinaga Institute of Biological Science, Inc., Kanagawa, Japan. Glucose and "PINEFIBER®", a low-digestible dextrin commercialized by Matsutani Chemical Industries Co, Ltd., Hyogo, Japan, were used as Control 1 and 2, respectively. Blood-sugar level and insulin level of each test group are in Tables 26 and 27, respectively.

TABLE 26

| | Blood-sugar level (mg/dl) | | |
|---|---|---|---|
| Time (min) | Branched α-glucan (Present invention) | Glucose (Control 1) | Low-digestible dextrin (Control 2) |
| Just before ingestion | 68 ± 17 | 76 ± 17 | 66 ± 15 |
| 15 | 121 ± 18 | 115 ± 24 | 109 ± 20 |
| 30 | 156 ± 29 | 210 ± 29 | 151 ± 18 |
| 60 | 150 ± 11 | 191 ± 8 | 150 ± 4 |
| 120 | 114 ± 9 | 144 ± 29 | 112 ± 15 |
| 180 | 80 ± 10 | 105 ± 17 | 90 ± 10 |

TABLE 27

| | Insulin level (ng/ml) | | |
|---|---|---|---|
| Time (min) | Branched α-glucan (Present invention) | Glucose (Control 1) | Low-digestible dextrin (Control 2) |
| Just before ingestion | 0.14 ± 0.07 | 0.33 ± 0.06 | 0.24 ± 0.21 |
| 15 | 0.73 ± 0.29 | 1.06 ± 0.44 | 0.46 ± 0.12 |
| 30 | 0.89 ± 0.26 | 1.46 ± 0.29 | 0.95 ± 0.40 |
| 60 | 0.60 ± 0.09 | 1.00 ± 0.26 | 0.48 ± 0.25 |
| 120 | 0.63 ± 0.20 | 0.67 ± 0.21 | 0.31 ± 0.22 |
| 180 | 0.43 ± 0.12 | 0.47 ± 0.04 | 0.27 ± 0.1 |

As is evident from the results in Tables 26 and 27, it was revealed that in the case of the branched α-glucan of the present invention, the elevation of blood-sugar level and insulin level was inhibited as in the case of the commercially available low-digestible dextrin in comparison with the case of glucose.

Experiment 19-5

Acute Toxicity Test

By using mice, the branched α-glucan obtained by the method in Experiment 19-1 was orally administrated to the mice for its acute toxicity test. As a result, it was revealed that the branched α-glucan of the present invention is a safe substance with a relatively low toxicity, and that no mouse died even when administrated with it at the highest possible dose. The $LD_{50}$ value of the branched α-glucan was 5 g/kg-mouse weight or higher.

Experiment 20

Inhibitory Effect of the Branched α-Glucan on the Elevation of Blood-Sugar Level In Experiment 19-4, it was revealed that the elevation of blood-sugar level and insulin value is inhibited by ingesting the branched α-glucan in comparison with the case of ingesting glucose. Based on the results, effect of the ingestion of the branched α-glucan on the elevation of blood-sugar level was further investigated in detail.

Experiment 20-1

Effects of the Ingestion of the Branched α-Glucan on Blood-Sugar Level and Insulin Level when the Branched α-Glucan is Ingested Together with Partial Starch Hydrolyzate The effect of the branched α-glucan on the elevation of blood-sugar level after ingesting "PINEDEX® #1", a partial starch hydrolyzate commercialized by Matsutani chemical Industries Co., Ltd., Hyogo, Japan, was investigated. Three groups of five Wister male rats (seven-weeks old)/group, purchased from Charles river Laboratories Japan Inc., Kanagawa, Japan, are preliminary reared for one week using "AIN-93G", a feed for rats prepared in Hayashibara Biochemical Laboratories Inc., Okayam, Japan, (Ref. Journal of Nutrition, vol. 123, pp. 1939-1951 (1993); hereinafter, called as "purified diet") and then fasted for one day. Successively, an aqueous solution prepared by dissolving the partial starch hydrolyzate and the branched α-glucan was orally administrated to the rats using a gastric sonde. The dose of the partial starch hydrolyzate was set to 1.5 g-solid/kg-body weight. The doses of the branched α-glucan were set to 0.15, 0.30, or 0.75 g-solid/kg-body weight for each group. Blood samples were withdrawn from the caudal vein of rats at just before administration, 15 min-after, 30 min-after, 60 min-after, 120 min-after, 180 min-after, and 240 min-after from the administration. Each blood sample was collected in a heparin-treated tube and then centrifuged at 2,000 rpm for 10 min to obtain blood plasma. The blood-sugar level and the insulin level in the blood plasma were measured by the method described in Experiment 19-4. As Control 1, five rats (one group) were administrated with 1.5 g/kg-body weight of the partial starch hydrolyzate. As Control 2, "FIBERSOL®-2", a low-digestible dextrin commercialized by Matsutani Chemical Industries Co., Ltd., Hyogo, Japan, was used as a substitute of the branched α-glucan and the low-digestible dextrin was administrated to two groups of rats (five rats/group) together with the partial starch hydrolyzate. The doses of the low-digestible dextrin were set to 0.15 and 0.75 g-solid/kg-body weight for the two groups of rats, respectively. The blood-sugar level, AUC value (area under the blood concentration-time curve) of blood-sugar level, insulin level, and AUC value of insulin level of each groups are in Tables 28, 29, 30, and 31, respectively.

TABLE 28

| | | Blood-sugar level (mg/dl) | | | | |
|---|---|---|---|---|---|---|
| | Partial starch hydrolyzate only | Branched α-glucan (Present invention) (g/kg-body weight) | | | Low-digestible dextrin (Control 2) (g/kg-body weight) | |
| Time (min) | (Control 1) | 0.15 | 0.30 | 0.75 | 0.15 | 0.75 |
| Just before ingestion | 50 ± 3 | 55 ± 10 | 60 ± 13 | 63 ± 4 | 56 ± 6 | 59 ± 3 |
| 15 | 124 ± 18 | 109 ± 14 | 105 ± 4 | 96 ± 4* | 107 ± 14 | 120 ± 5 |
| 30 | 220 ± 37 | 171 ± 21 | 151 ± 11 | 130 ± 5* | 164 ± 2 | 162 ± 12 |
| 60 | 175 ± 25 | 170 ± 23 | 162 ± 9 | 145 ± 6* | 168 ± 24 | 187 ± 10 |
| 120 | 110 ± 9 | 122 ± 16 | 135 ± 16 | 126 ± 4* | 134 ± 18 | 140 ± 16 |
| 180 | 91 ± 18 | 88 ± 11 | 99 ± 10 | 97 ± 5* | 100 ± 13 | 112 ± 13 |
| 240 | 85 ± 17 | 72 ± 10 | 75 ± 3 | 69 ± 9 | 84 ± 12 | 76 ± 3 |

*Significantly different from the case of a low-digestible dextrin (0.75 g/kg-body weight)
($P < 0.05$ or $P < 0.01$)

TABLE 29

| | | AUC value of blood-sugar level (mg/dl min) | | | | |
|---|---|---|---|---|---|---|
| | Partial starch hydrolyzate only | Branched α-glucan (Present invention) (g/kg-body weight) | | | Low-digestible dextrin (Control 2) (g/kg-body weight) | |
| Time (min) | (Control 1) | 0.15 | 0.30 | 0.75 | 0.15 | 0.75 |
| Just before ingestion | 0.0 | 0.0 | 0.0 | 0.0 | 0.0 | 0.0 |
| 15 | 553 ± 119 | 410 ± 127 | 336 ± 90 | 254 ± 14* | 383 ± 129 | 458 ± 30 |
| 30 | 2,377 ± 402 | 1,690 ± 206 | 1,358 ± 315 | 1,013 ± 54* | 1,577 ± 299 | 1,687 ± 149 |
| 60 | 6,796 ± 1,028 | 5,165 ± 23 | 4,270 ± 825 | 3,264 ± 219* | 4,869 ± 638 | 5,157 ± 457 |
| 120 | 12,354 ± 1,538 | 10,666 ± 1,385 | 9,612 ± 1,567 | 76,467 ± 494* | 10,555 ± 1,711 | 11,457 ± 1,013 |
| 180 | 15,372 ± 1,760 | 13,698 ± 1,735 | 13,043 ± 2,306 | 10,585 ± 759* | 14,215 ± 2,388 | 15,515 ± 1,558 |
| 240 | 17,612 ± 2,624 | 15,229 ± 1,788 | 14,679 ± 3,073 | 11,822 ± 1,144* | 16,376 ± 2,428 | 17,637 ± 1,716 |

*Significantly different from the case of a low-digestible dextrin (0.75 g/kg-body weight)
($P < 0.01$)

TABLE 30

| | | Insulin level (ng/ml) | | | | |
|---|---|---|---|---|---|---|
| | Partial starch hydrolyzate only | Branched α-glucan (Present invention) (g/kg-body weight) | | | Low-digestible dextrin (Control 2) (g/kg-body weight) | |
| Time (min) | (Control 1) | 0.15 | 0.30 | 0.75 | 0.15 | 0.75 |
| Just before ingestion | 0.67 ± 0.02 | 0.65 ± 0.04 | 0.67 ± 0.06 | 0.67 ± 0.10 | 0.68 ± 0.05 | 0.67 ± 0.06 |
| 15 | 1.14 ± 0.34 | 0.72 ± 0.10 | 0.80 ± 0.01 | 0.81 ± 0.08 | 0.94 ± 0.10 | 1.08 ± 0.33 |
| 30 | 2.54 ± 0.21 | 1.23 ± 0.36 | 1.14 ± 0.30 | 1.04 ± 0.04 | 1.65 ± 0.25 | 1.02 ± 0.07 |
| 60 | 1.06 ± 0.16 | 0.86 ± 0.07 | 0.83 ± 0.06 | 0.81 ± 0.11* | 1.02 ± 0.19 | 0.95 ± 0.05 |
| 120 | 0.81 ± 0.07 | 0.75 ± 0.03 | 0.76 ± 0.03 | 0.73 ± 0.03* | 0.82 ± 0.06 | 0.79 ± 0.60 |
| 180 | 0.50 ± 0.03 | 0.69 ± 0.08 | 0.56 ± 0.03 | 0.52 ± 0.26 | 0.57 ± 0.05 | 0.54 ± 0.04 |
| 240 | 0.51 ± 0.08 | 0.54 ± 0.05 | 0.53 ± 0.02 | 0.54 ± 0.03* | 0.50 ± 0.02 | 0.51 ± 0.01 |

*Significantly different from the case of a low-digestible dextrin (0.75 g/kg-body weight)
($P < 0.05$)

TABLE 31

| | AUC value of insulin level (ng/ml min) | | | | | |
|---|---|---|---|---|---|---|
| | Partial starch hydrolyzate only | Branched α-glucan (Present invention) (g/kg-body weight) | | | Low-digestible dextrin (Control 2) (g/kg-body weight) | |
| Time (min) | (Control 1) | 0.15 | 0.30 | 0.75 | 0.15 | 0.75 |
| Just before ingestion | 0.0 | 0.0 | 0.0 | 0.0 | 0.0 | 0.0 |
| 15 | 3.5 ± 2.6 | 0.5 ± 0.8 | 0.9 ± 0.5 | 1.1 ± 1.1 | 2.0 ± 1.2 | 3.1 ± 2.7 |
| 30 | 21.1 ± 5.9 | 5.4 ± 4.3 | 5.4 ± 2.2 | 4.9 ± 3.1 | 11.3 ± 2.1 | 8.8 ± 6.1 |
| 60 | 54.9 ± 6.1 | 17.1 ± 10.3 | 14.9 ± 6.1 | 12.7 ± 6.9 | 31.0 ± 6.6 | 18.2 ± 8.3 |
| 120 | 70.7 ± 4.6 | 26.2 ± 11.7 | 22.5 ± 7.2 | 19.7 ± 12.8 | 45.7 ± 12.4 | 30.2 ± 12.3 |
| 180 | 74.9 ± 6.8 | 30.8 ± 12.9 | 25.2 ± 8.6 | 23.0 ± 16.8 | 49.9 ± 13.1 | 34.0 ± 14.7 |
| 240 | — | 32.4 ± 13.8 | — | 24.2 ± 19.2 | — | — |

—: AUC value was not calculated because the insulin level was lowered than that of just before ingestion.

As is evident from the results in Tables 28 to 31, it was revealed that the branched α-glucan of the present invention showed a dose-dependent inhibition of elevating blood-sugar level, AUC value of blood-sugar level, insulin level, and AUC value of insulin level when a saccharide (partial starch hydrolyzate) was loaded in comparison with the case of administrating the partial starch hydrolyzate only (Control 1), similarly with the case of administrating the low-digestible dextrin (Control 2). Comparing the degree of the inhibitory effects between the branched α-glucan and the low-digestible dextrin, the branched α-glucan of the present invention shows relatively strong effects than the low-digestible dextrin.

Experiment 20-2

Effects of the Molecular Weight of the Branched α-Glucan on Blood-Sugar Level and Insulin Level when the Branched α-Glucan is Ingested Together with the Partial Starch Hydrolyzate In Experiment 20-1, it was revealed that the branched α-glucan of the present invention inhibits the elevation of blood-sugar level, AUC value of blood-sugar level, insulin level, and AUC value of insulin level when it was ingested together with a saccharide (partial starch hydrolyzate). Successively, effect of the molecular weight of the branched α-glucan on the inhibitory effect on blood-sugar level and insulin level was investigated. Varying the kinds of material partial starch hydrolyzate and the amounts of the α-glucosyl- transferase and the amylase, various branched α-glucans having the weight-average molecular weights, shown in Table 32, were prepared. As in the same manner in Experiment 20-1, nine groups of five Wister male rats (seven-weeks old)/group, purchased from Charles river Laboratories Japan Inc., Kanagawa, Japan, are preliminary reared for one week using the purified diet and then fasted for one day. Successively, an aqueous solution prepared by dissolving the partial starch hydrolyzate and any one of the branched α-glucan shown in Table 32 was orally administrated to 8 groups of rats using a gastric sonde. The doses of the partial starch hydrolyzate and the branched α-glucan were respectively set to 1.5 g-solid/kg-body weight and 0.75 g-solid/kg-body weight for each group. To the remaining one group of rats, 1.5 g/kg-body weight of the partial starch hydrolyzate only was orally administrated as a control group. Blood samples were withdrawn from the caudal vein of rats at just before administration and 30 min-after from the administration. Each blood sample was collected in a heparin-treated tube and then centrifuged at 2,000 rpm for 10 min to obtain blood plasma. The blood-sugar level and the inslin level in the blood plasma were measured and in Table 32. The timing of collecting blood sample after the administration was set to 30 min-after from the administration because blood-sugar level and insulin level reach peaks at the timing when the partial stach hydolyzate only is administrated.

TABLE 32

| Sample No. | Weight-average molecular weight | WSDF content (%, w/w) | Blood-sugar level (mg/dl) | | Insulin level (ng/ml) | |
|---|---|---|---|---|---|---|
| | | | Before ingestion | 30 min-later after ingestion | Before ingestion | 30 min-later after ingestion |
| Partial starch hydrolyzate only (Control) | — | — | 62 ± 6 | 225 ± 40 | 0.66 ± 0.02 | 2.78 ± 0.03 |
| 1 | 1,168 | 58.1 | 64 ± 7 | 173 ± 30 | 0.65 ± 0.07 | 1.86 ± 0.05 |
| 2 | 2,670 | 75.5 | 63 ± 12 | 144 ± 27 | 0.65 ± 0.05 | 1.36 ± 0.06 |
| 3 | 4,242 | 80.4 | 56 ± 9 | 132 ± 15 | 0.67 ± 0.04 | 1.02 ± 0.07 |
| 4 | 25,618 | 72.4 | 61 ± 3 | 139 ± 15 | 0.59 ± 0.03 | 1.21 ± 0.12 |
| 5 | 44,151 | 64.2 | 62 ± 8 | 142 ± 25 | 0.65 ± 0.03 | 1.31 ± 0.09 |
| 6 | 60,000 | 42.3 | 59 ± 7 | 157 ± 19 | 0.62 ± 0.05 | 1.74 ± 0.06 |
| 7 | 100,000 | 36.5 | 61 ± 10 | 185 ± 28 | 0.58 ± 0.03 | 2.05 ± 0.05 |
| 8 | 200,000 | 30.1 | 58 ± 4 | 198 ± 22 | 0.65 ± 0.02 | 2.26 ± 0.05 |

As is evident from the results in Table 32, the branched α-glucans having the weight-average molecular weights in the range of 1,168 to 200,000 inhibited the elevation of blood-sugar level and insulin level when the partial starch hydrolyzate was orally administrated. Comparing the degree of inhibiting the elevation of blood-sugar level and insulin level among the branched α-glucans, the inhibitory effect is significant in the cases of using the branched α-glucans having the molecular weights in the range of 1,168 to 60,000 (the WSDF contents in the range of 58.1 to 80.4% (w/w)), and is more significant in the cases of using the branched α-glucans having the molecular weights in the range of 2,670 to 44,151 (the WSDF contents in the range of 64.2 to 80.4% (w/w)).

Experiment 20-3

Effects of a Long-Period Ingestion of the Branched α-Glucan on Blood-Sugar Level and Insulin Level when the Partial Starch Hydrolyzate is Ingested In Experiment 20-1, it was revealed that the branched α-glucan of the present invention inhibits the elevation of blood-sugar level, AUC value of blood-sugar level, insulin level, and AUC value of insulin level when it was ingested together with a saccharide (partial starch hydrolyzate). In this experiment, effect of a long period (8 weeks) ingestion of the branched α-glucan on the inhibition of elevating blood-sugar level, AUC value of blood-sugar level, insulin level, and AUC value of insulin level when the partial starch hydrolyzate is ingested was investigated. Five groups of five Wister male rats (seven-weeks old)/group, purchased from Charles river Laboratories Japan Inc., Kanagawa, Japan, were preliminary reared for one week using the purified diet. Then, three groups of rats were rared for 8 weeks using three kinds of test diets incorporated the branched α-glucan in an amount of 1, 2, or 5% (w/w), shown in Table 33. The rats were allowed to ingest the test diet and water freely during the test period. At the point of rearing 4-weeks and 8-weeks, the rats were fasted for one day and then an aqueous solution prepared by dissolving the partial starch hydrolyzate was orally administrated to the rats using a gastric sonde to give a dose of 1.5 g-solid/kg-body weight. Blood samples were withdrawn from the caudal vein of rats at just before administration, 15 min-after, 30 min-after, 60 min-after, 120 min-after, 180 min-after, and 240 min-after from the administration. Each blood sample was collected in a heparin-treated tube and then centrifuged at 2,000 rpm for 10 min to obtain blood plasma. The blood-sugar level and the inslin level in the blood plasma were measured by the method described in Experiment 19-4. As Control 1, one group of rats (five rats/group) was reared using the purified diet only. As Control 2, the remaining one group of rats (five rats/group) was rared using a diet with a formula in Table 33, in which a part of corn starch in the purified diet was substituted with "FIBERSOL-2®", a low-digestible dextrin commercialized by Matsutani Chemical Industries Co., Ltd., Hyogo, Japan. Since almost the same results were obtained from samples at the point of rearing 4-weeks and 8-weeks, the results of measuring blood-sugar level, AUC value of blood-sugar level, insulin level, and AUC value of insulin level at the point of rearing 4-weeks for each group were are in Tables 34, 35, 36, and 37, respectively.

TABLE 33

| | Composition (%, w/w) | | | | |
|---|---|---|---|---|---|
| | | Branched α-glucan (%, w/w) | | | Low-digestible dextrin (%, w/w) |
| Ingredient | Purified diet | 1 | 2 | 5 | 5 |
| Corn starch | 39.7486 | 38.7486 | 37.7486 | 34.7486 | 34.7486 |
| α-Starch | 13.2 | 13.2 | 13.2 | 13.2 | 13.2 |
| Casein | 20 | 20 | 20 | 20 | 20 |
| Sucrose | 10 | 10 | 10 | 10 | 10 |
| Soybean oil | 7 | 7 | 7 | 7 | 7 |
| Cellulose | 5 | 5 | 5 | 5 | 5 |
| Mineral mix | 3.5 | 3.5 | 3.5 | 3.5 | 3.5 |
| Vitamin mix | 1 | 1 | 1 | 1 | 1 |
| L-Cystine | 0.3 | 0.3 | 0.3 | 0.3 | 0.3 |
| Colin bitartrate | 0.25 | 0.25 | 0.25 | 0.25 | 0.25 |
| t-Butyl-hydroquinone | 0.0014 | 0.0014 | 0.0014 | 0.0014 | 0.0014 |
| Branched α-glucan | 0 | 1 | 2 | 5 | 0 |
| Low-digestible dextrin | 0 | 0 | 0 | 0 | 5 |

TABLE 34

| | Blood-sugar level (mg/dl) | | | | |
|---|---|---|---|---|---|
| Time (min) | Purified diet (Control 1) | Diet containing 1% (w/w) Branched α-glucan | Diet containing 2% (w/w) Branched α-glucan | Diet containing 5% (w/w) Branched α-glucan | Diet containing 5% (w/w) Low-digestible dextrin (Control 2) |
| Just before ingestion | 80 ± 4 | 66 ± 5 | 53 ± 4 | 54 ± 4 | 59 ± 5 |
| 15 | 180 ± 8 | 123 ± 16 | 70 ± 8 | 79 ± 8* | 97 ± 19 |
| 30 | 245 ± 11 | 184 ± 16 | 122 ± 17 | 120 ± 17 | 120 ± 14 |
| 60 | 218 ± 13 | 190 ± 15 | 142 ± 29 | 126 ± 29* | 161 ± 26 |
| 120 | 149 ± 10 | 162 ± 12 | 108 ± 32 | 101 ± 32* | 154 ± 12 |
| 180 | 115 ± 9 | 120 ± 9 | 88 ± 19 | 84 ± 19* | 111 ± 9 |
| 240 | 91 ± 8 | 87 ± 10 | 71 ± 18 | 65 ± 18* | 95 ± 4 |

*Significantly different from the case of the diet containing 5% (w/w) low-digestible dextrin (P < 0.05 or P < 0.01)

TABLE 35

| | AUC value of blood-sugar level (mg/dl min) | | | | |
|---|---|---|---|---|---|
| Time (min) | Purified diet (Control 1) | Diet containing 1% (w/w) Branched α-glucan | Diet containing 2% (w/w) Branched α-glucan | Diet containing 5% (w/w) Branched α-glucan | Diet containing 5% (w/w) Low-digestible dextrin (Control 2) |
| Just before ingestion | 0.0 | 0.0 | 0.0 | 0.0 | 0.0 |
| 15 | 751 ± 59 | 427 ± 158 | 126 ± 26 | 184 ± 98 | 272 ± 69 |
| 30 | 2,746 ± 179 | 1,746 ± 299 | 772 ± 85 | 860 ± 272* | 986 ± 268 |
| 60 | 7,303 ± 526 | 5,394 ± 273 | 3,147 ± 425 | 2,925 ± 510* | 3,368 ± 820 |
| 120 | 13,525 ± 1,032 | 12,012 ± 1,177 | 7,457 ± 1,308 | 6,488 ± 1,002* | 9,141 ± 2,311 |
| 180 | 16,661 ± 1,216 | 16,520 ± 1,476 | 10,153 ± 1,670 | 8,791 ± 1,450* | 13,413 ± 3,479 |
| 240 | 18,073 ± 1,262 | 18,778 ± 1,717 | 11,771 ± 1,933 | 10,022 ± 1,734 | 15,939 ± 4,382 |

*Significantly different from the case of the diet containing 5% (w/w) low-digestible dextrin ($P < 0.05$ or $P < 0.01$)

TABLE 36

| | Insulin level (ng/ml) | | | | |
|---|---|---|---|---|---|
| Time (min) | Purified diet (Control 1) | Diet containing 1% (w/w) Branched α-glucan | Diet containing 2% (w/w) Branched α-glucan | Diet containing 5% (w/w) Branched α-glucan | Diet containing 5% (w/w) Low-digestible dextrin (Control 2) |
| Just before ingestion | 0.61 ± 0.14 | 0.51 ± 0.04 | 0.49 ± 0.11 | 0.46 ± 0.07 | 0.53 ± 0.05 |
| 15 | 1.78 ± 0.40 | 1.16 ± 0.30 | 0.88 ± 0.16 | 0.90 ± 0.18* | 1.26 ± 0.23 |
| 30 | 3.16 ± 0.29 | 1.99 ± 0.52 | 1.17 ± 0.36 | 1.28 ± 0.31* | 1.72 ± 0.31 |
| 60 | 1.41 ± 0.23 | 1.23 ± 0.30 | 0.85 ± 0.14 | 0.79 ± 0.16* | 1.15 ± 0.11 |
| 120 | 0.95 ± 0.23 | 0.82 ± 0.16 | 0.63 ± 0.17 | 0.64 ± 0.13 | 0.72 ± 0.86 |
| 180 | 0.63 ± 0.07 | 0.56 ± 0.09 | 0.58 ± 0.11 | 0.55 ± 0.17 | 0.67 ± 0.09 |
| 240 | 0.63 ± 0.06 | 0.53 ± 0.07 | 0.47 ± 0.08 | 0.46 ± 0.07 | 0.62 ± 0.10 |

*Significantly different from the case of the diet containing 5% (w/w) low-digestible dextrin ($P < 0.05$ or $P < 0.01$)

TABLE 37

| | AUC value of insulin level (ng/ml min) | | | | |
|---|---|---|---|---|---|
| Time (min) | Purified diet (Control 1) | Diet containing 1% (w/w) Branched α-glucan | Diet containing 2% (w/w) Branched α-glucan | Diet containing 5% (w/w) Branched α-glucan | Diet containing 5% (w/w) Low-digestible dextrin (Control 2) |
| Just before ingestion | 0.0 | 0.0 | 0.0 | 0.0 | 0.0 |
| 15 | 8.8 ± 3.0 | 4.9 ± 2.4 | 2.9 ± 1.4 | 3.3 ± 1.5* | 5.5 ± 2.1 |
| 30 | 36.7 ± 5.8 | 20.9 ± 8.6 | 11.0 ± 3.1 | 12.7 ± 4.8* | 19.9 ± 6.1 |
| 60 | 87.1 ± 11.2 | 53.9 ± 19.1 | 26.5 ± 5.7 | 29.8 ± 11.9* | 46.0 ± 11.5 |
| 120 | 121.6 ± 14.0 | 84.7 ± 30.0 | 41.5 ± 10.0 | 45.0 ± 20.5* | 71.0 ± 14.1 |
| 180 | 134.0 ± 17.2 | 95.8 ± 35.0 | 48.5 ± 15.2 | 53.9 ± 24.8* | 80.7 ± 16.1 |
| 240 | 137.8 ± 23.5 | 98.7 ± 36.2 | 51.8 ± 16.7 | 57.4 ± 26.7* | 87.4 ± 20.0 |

*Significantly different from the case of the diet containing 5% (w/w) low-digestible dextrin ($P < 0.05$ or $P < 0.01$)

As is evident from the results in Tables 33 to 37, it was revealed that the branched α-glucan of the present invention inhibited the elevation of blood-sugar level, AUC value of blood-sugar level, insulin level, and AUC value of insulin level when a saccharide (partial starch hydrolyzate) was loaded in comparison with the case of raring rats using the purified diet only (Control 1), similarly with the case of raring rats using the low-digestible dextrin (Control 2). It was also revealed that the inhibitory effect is dependent on the amount of the branched α-glucan incorporated into the test diet, and the inhibitory effect is significant in the case of incorporating the branched α-glucan in an amount of 2% (w/w), and more significant in the case of incorporating the branched α-glucan in an amount of 5% (w/w). In the case of using a test diet incorporated with 5% (w/w) of the commercially available low-digestible dextrin, the degree of the inhibitory effect was almost equal with the case of using a test diet incorporated with 1% (w/w) of the branched α-glucan. From the results, it was confirmed that the branched α-glucan of the present invention is advantageous in the effect of inhibiting the elevation of blood-sugar level, AUC value of blood-sugar level, insulin level, and AUC value of insulin level when a saccharide (partial starch hydrolyzate) is loaded, in comparison with the low-digestible dextrin. Comparing the blood-sugar level and insulin level just before ingestion among the test groups, those values in the groups ingested the test diet incorporated with 2 or 5% (w/w) of the branched α-glucan is lower than those in the groups ingested the control diet or the test diet incorporated with 5% (w/w) of the low digestible dextrin. From the results, it was revealed that the branched α-glucan of the present invention lowered fasting blood-sugar level and insulin level effectively when it was used for a long period than the commercially available low-digestible dextrin. While, the body weights of rats were compared between the test group and control group at the point of raring 4 and 8 weeks but no significant difference was observed in the average body weight between the groups. From the results, it was considered that the effect of inhibiting the elevation of blood-sugar level and insulin level by the branched α-glucan, confirmed by this experiment, does not influence the health of rats.

Experiment 21

Effects of the Ingestion of the Branched α-Glucan on Blood-Sugar Level and Insulin Level of Humans From the above experiments using rats, it was revealed that the elevations of blood-sugar level and insulin level are inhibited by ingesting the branched α-glucan together with the partial starch hydrolyzate in comparison with the case of ingesting the partial starch hydrolyzate only. Successively, the effects of the ingestion of the branched α-glucan on the blood-sugar level and insulin level of humans were investigated as follows: By using "PINEDEX #1®", a partial starch hydrolyzate commercialized by Matsutani Chemical Industries Co., Ltd., Hyogo, Japan, and the branched α-glucan prepared according to the method in Example 5 described later, the elevation of blood-sugar level and insulin level of humans were investigated. Twelve healthy male volunteers (age 26 to 54, average age 41±1) were used as subjects, and their ingestion of foods except for water was restricted during 21 o'clock of the previous day to 9 o'clock of the next day (time of starting the test). The subjects were allowed to ingest the test preparation, prepared by dissolving 50 g-solid of the partial starch hydrolyzate into water and filling up to 200 ml, within a time frame of 2 min, and the blood samples were collected at the points of just before ingestion, 15 min-after, 30 min-after, 45 min-after, 60 min-after 90 min-after, and 120 min-after the ingestion. After the one week or more interval, the same subjects were allowed to ingest the test preparation, prepared by dissolving 50 g-solid of the branched α-glucan into water and filling up to 200 ml, and the blood samples were collected in the same manner. The blood-sugar level and insulin level of each blood sample were measured by entrusting to Medical Center of Okayama Medical Association, a private clinical laboratory, Okayama, Japan. Time courses of blood-sugar level and insulin level, AUC value of blood-sugar from just after ingestion to 120 min-after ingestion ($AUC^{0-2\ hr}$ (mg hr/dl)), AUC value of insulin level of the period ($AUC^{0-2\ hr}$ (μU hr/dl)), and the increase of AUC values of blood-sugar level and insulin level of the period ($\Delta AUC^{0-2\ hr}$) are summarized in Table 38.

TABLE 38

| | Blood-sugar level (mg/dl) | | Insulin level (μU/ml) | |
|---|---|---|---|---|
| Time (min) | Partial starch hydrolyzate (Control) | Branched α-glucan | Partial starch hydrolyzate (Control) | Branched α-glucan |
| Just before ingestion | 87 ± 6 | 87 ± 1 | 5.7 ± 2.1 | 4.9 ± 1.7 |
| 15 | 113 ± 12 | 102 ± 8 | 22.7 ± 13.4 | 17.5 ± 15.3 |
| 30 | 132 ± 15 | 112 ± 10* | 36.8 ± 13.3 | 25.6 ± 18.5 |
| 60 | 137 ± 21 | 113 ± 19* | 40.9 ± 14.8 | 22.4 ± 9.6* |

TABLE 38-continued

| | Blood-sugar level (mg/dl) | | Insulin level (μU/ml) | |
|---|---|---|---|---|
| Time (min) | Partial starch hydrolyzate (Control) | Branched α-glucan | Partial starch hydrolyzate (Control) | Branched α-glucan |
| 120 | 121 ± 20 | 108 ± 24 | 39.6 ± 17.1 | 18.8 ± 7.3* |
| 180 | 90 ± 17 | 89 ± 12 | 26.9 ± 13.5 | 11.9 ± 4.6* |
| 240 | 79 ± 17 | 80 ± 3 | 12.7 ± 7.2 | 6.7 ± 2.0* |
| $AUC^{0-2\ hr}$ | 217 ± 23 | 197 ± 20* | 57.3 ± 21.2 | 31.7 ± 11.1* |
| $\Delta AUC^{0-2\ hr}$ | 47.4 ± 12.8 | 28.5 ± 15.2* | 45.8 ± 17.5 | 22.0 ± 8.4* |

*Significantly different from the case of Control (P < 0.05 or P < 0.01)

As is evident from the results in Table 38, in the case of ingesting the branched α-glucan of the present invention, it was revealed that blood-sugar level, AUC value of blood-sugar level, insulin level, and AUC value of insulin level were significantly low in comparison with the case of ingesting the partial starch hydrolyzate, similarly with the case in Experiment 20 using rats.

Experiment 22

Effect of the Branched α-Glucan on the Lowering of Lipids in Living Bodies

From the results in Experiments 19-4 and 21, it was revealed that the elevation of blood-sugar level and insulin level was inhibited by ingesting the branched α-glucan. Successively, the effect of the ingestion of the branched α-glucan on the amount of lipids in living bodies was investigated.

Experiment 22-1

Effect of the Ingestion of the Branched α-Glucan on the Absorption of Lipids

Seven-weeks old of Wister male rats, purchased from Charles river Laboratories Japan Inc., Kanagawa, Japan, were randomly divided into four groups, 15 rats/group, and preliminary reared for one week using the purified diet shown in Table 33. The branched α-glucan prepared by the method in Example 5 described later was used in this experiment. Then, two groups of rats were reared for 4 weeks or 8 weeks using the test diets incorporated with the branched α-glucan in an amount of 5% (w/w), shown in Table 33. The remaining two groups of rats were reared for 4 weeks or 8 weeks using the purified diet as control groups. After rearing 4 weeks or 8 weeks, rats in the test group, reared using the test diet incorporated with the branched α-glucan, and those in the control group were killed by collecting blood from postcaval vein under ether anesthesia and dissected; and then the amount of lipids accumulated in the internal organ, the level of serum lipids, the wet-weight of intestinal mucosa, the contents in cecum, etc. were investigated. The results are in Table 39. Rats were reared with measuring the body-weight and the feed intake at 2 or 3 days interval and were allowed to ingest the diet and water freely during the test period. Rats were fasted for one night before the dessection. The body weight gain, feed intake, food efficacy (body weight gain/feed intake), body weight at the point of dissection, weights of organs, weight of intestinal mucosa, weights of lipids of internal organs, weight of the content of cecum, moisture content of the content of cecum, and pH of the content of cecum are in Table 39. The levels of serum lipids are also in Table 39. In the sreum lipids, the levels of triglyceride, total cholesterol, and HDL-cholesterol were determined by using "TRIGLYCERIDE E-TEST WAKO", a kit for measuring triglyceride commercialized by Wako Pure Chemical Industries Ltd., Osaka, Japan, "CHOLESTEROL E-TEST WAKO", a kit for measuring total cholesterol commercialized by Wako Pure Chemical Industries Ltd., Osaka, Japan, and "HDL-CHOLESTEROL E-TEST WAKO", a kit for measuring HDL-cholesterol commercialized by Wako Pure Chemical Industries Ltd., Osaka, Japan, respectively. The level of LDL-cholesterol was calculated by subtracting the value of HDL-cholesterol from that of total cholesterol.

ther, the weight of intestinal mucosa was increased in the test group. From the result, it is suggested that the thickening of intestinal mucosa accompanying the increase of mucin secration, the decrease of digestive enzyme activities caused by the thickening, and the inhibition or delay of the digestion or absorption of glucose and lipids play important roles on the inhibition of excess accumulation of lipids and enhancement of carbohydrate tolerance, confirmed by Experiments 20 and 21.

TABLE 39

| | | 4 weeks-rearing | | 8 weeks-rearing | |
| --- | --- | --- | --- | --- | --- |
| | Measurement | Purified diet (Control) | Diet containing 5% (w/w) Branched α-glucan | Purified diet (Control) | Diet containing 5% (w/w) Branched α-glucan |
| Food efficacy | Body weight gain (g) | 107.7 ± 9.0 | 109.0 ± 16.9 | 174.1 ± 21.2 | 171.8 ± 11.6 |
| | Intake (g) | 486.7 ± 32.2 | 488.7 ± 53.1 | 938.2 ± 43.6 | 962.1 ± 80.7 |
| | Efficacy | 0.22 ± 0.01 | 0.22 ± 0.01 | 0.19 ± 0.02 | 0.18 ± 0.02 |
| Weight of internal organ | Body weight (g) | 348.0 ± 11.6 | 345.0 ± 24.9 | 429.2 ± 22.6 | 424.6 ± 13.1 |
| | Liver | 9.76 ± 0.85 | 9.59 ± 1.49 | 10.44 ± 0.74 | 10.42 ± 0.98 |
| | Kidney | 1.28 ± 0.11 | 1.23 ± 0.19 | 2.84 ± 0.30 | 2.43 ± 0.89 |
| | Spleen | 0.86 ± 0.09 | 0.82 ± 0.10 | 0.90 ± 0.08 | 0.85 ± 0.06 |
| Weight of intestinal mucosa | Jejunal mucosa (g) | 1.06 ± 0.16 | 1.31 ± 0.25* | 1.26 ± 0.14 | 1.55 ± 0.23** |
| | Ileal mucosa (g) | 0.96 ± 0.22 | 1.15 ± 0.12* | 1.10 ± 0.22 | 1.51 ± 0.20** |
| | Cecal tissue (g) | 0.99 ± 0.18 | 1.03 ± 0.16 | 1.11 ± 0.20 | 1.46 ± 0.21** |
| Weight of lipids in internal organ | Around mesenterium (g) | 4.37 ± 1.40 | 4.49 ± 0.84 | 6.02 ± 1.19 | 6.99 ± 1.37 |
| | Around kidney (g) | 6.24 ± 3.36 | 4.15 ± 0.98 | 8.05 ± 2.69 | 4.74 ± 1.70* |
| | Around testis (g) | 5.70 ± 1.86 | 3.32 ± 1.12* | 9.25 ± 2.23 | 3.68 ± 0.84** |
| Contents in cecum | Weight (g) | 2.17 ± 0.70 | 2.17 ± 0.70 | 2.37 ± 0.73 | 2.39 ± 0.74 |
| | Moisture content (%) | 76.8 ± 3.0 | 76.3 ± 4.0 | 76.7 ± 3.1 | 77.2 ± 3.7 |
| | pH | 8.75 ± 0.23 | 8.59 ± 0.19 | 8.70 ± 0.35 | 8.28 ± 0.48* |
| Serum lipid | Triglyceride (mg/dl) | 55.7 ± 11.7 | 56.9 ± 14.9 | 58.2 ± 13.8 | 47.2 ± 10.5 |
| | Total cholesterol (mg/dl) | 68.1 ± 11.3 | 59.2 ± 10.4 | 62.1 ± 10.2 | 54.7 ± 11.2 |
| | HDL-Cholesterol (mg/dl) | 53.1 ± 7.4 | 47.4 ± 9.3 | 37.6 ± 5.0 | 33.5 ± 5.5 |
| | LDL-Cholesterol (mg/dl) | 15.0 ± 4.9 | 11.8 ± 3.1 | 24.4 ± 6.1 | 21.2 ± 5.5 |

*Significantly different from the case of Control ($P < 0.05$)
**Significantly different from the case of Control ($P < 0.01$)

As is evident from the results in Table 39, in the case of allowing rats to ingest the test diet incorporated with 5% (w/w) of the branched α-glucan of the present invention, the weights of lipids around kidney and testis were lower at the point of rearing for 4 weeks in comparison with the case of allowing rats to ingest the purified diet only. At the point of rearing for 8 weeks, the weights of lipids around kidney and testis were, particularly, the weight of lipids around testis was significantly lower than those of control. Also, the weight of intestinal mucosa was significantly increased in the test group at the point of rearing for 4 and 8 weeks, and more significantly at the point of rearing for 8 weeks. Further, the pH of the content in cecum in the test group was significantly lowered at the point of rearing for 8 weeks. Regarding the level of serum lipids, the value of triglyceride in the test group tended to decrease at the point of rearing 8 weeks, and the values of total cholesterol and LDL-cholesterol tended to decrease at the points of rearing 4 and 8 weeks. Other results except for those described above were almost equal between the test group and the control group. The level of organic acids in cecum was not different between the test group and the control group (data not shown). These results described above indicate that the branched α-glucan of the present invention exercises the effect of lowering lipids in living bodies. Fur- Experiment 22-2

Effects of the Molecular Weight of the Branched α-Glucan on the Inhibition of Excess Accumulation of Lipids in Living Bodies In Experiment 22-1, it was revealed that the ingestion of the branched α-glucan of the present invention inhibits the excess accumulation of lipids in living bodies. Successively, effect of the weight-average molecular weight of the branched α-glucan on the inhibitory effect was investigated. Eight kinds of test diets were prepared by incorporating 8 kinds of branched α-glucan with different weight average molecular weight, used in Experiment 20-2, into the purified diet to give a content of 5% (w/w). Forty-five Wister male rats (seven-weeks old), purchased from Charles river Laboratories Japan Inc., Kanagawa, Japan, were divided into 9 groups, 5 rats/group, and preliminary reared for one week using the purified diet. Eight groups of rats were reared for 8 weeks using any one of the test diets (test diet Nos. 1 to 8) incorporated with the branched α-glucan with different weight-average molecular weight, shown in Table 40. The remaining one group of rats was reared using the purified diet for 8 weeks as a control group. After rearing 8 weeks, 8 groups of rats as test groups and one group of rats as control group were killed by collecting blood under ether anesthesia; and then, the weights of lipids (wet-weight) around mesenterium, kidney, and testis, and the levels of triglyceride and total cholesterol were measured by the same method in Experiment 22-1. The results are in Table 40.

TABLE 40

| Test diet No. used for breeding | Branched α-glucan incorporated into the purified diet | | Weight of lipids in internal organ (g) | | | Serum lipids (mg/dl) | |
|---|---|---|---|---|---|---|---|
| | Weight-average molecular weight | WSDF content (%, w/w) | Around mesenterium | Around kidney | Around testis | Triglyceride | Total cholesterol |
| Reared Using purified diet only (Control) | — | — | 6.22 ± 1.09 | 8.65 ± 2.79 | 8.95 ± 2.16 | 60.1 ± 12.6 | 63.1 ± 9.8 |
| 1 | 1,168 | 58.1 | 6.24 ± 1.48 | 6.28 ± 1.79 | 7.28 ± 2.32 | 49.8 ± 9.1 | 54.7 ± 8.9 |
| 2 | 2,670 | 75.5 | 5.92 ± 1.29 | 5.12 ± 1.43 | 4.65 ± 1.01 | 45.4 ± 8.2 | 48.5 ± 9.1 |
| 3 | 4,242 | 80.4 | 5.64 ± 1.18 | 4.43 ± 1.55 | 3.26 ± 0.72 | 46.5 ± 11.5 | 50.1 ± 10.3 |
| 4 | 25,618 | 72.4 | 5.53 ± 1.32 | 4.86 ± 1.75 | 4.32 ± 1.25 | 47.1 ± 7.8 | 49.8 ± 8.9 |
| 5 | 44,151 | 64.2 | 5.78 ± 1.57 | 5.36 ± 1.88 | 5.89 ± 1.37 | 50.1 ± 6.9 | 53.2 ± 10.1 |
| 6 | 60,000 | 42.3 | 6.01 ± 1.41 | 5.86 ± 1.77 | 6.45 ± 1.96 | 52.9 ± 9.1 | 55.3 ± 9.4 |
| 7 | 100,000 | 36.5 | 6.35 ± 1.85 | 6.81 ± 2.06 | 7.22 ± 2.08 | 57.7 ± 8.6 | 58.7 ± 12.3 |
| 8 | 200,000 | 30.1 | 6.29 ± 1.98 | 7.45 ± 2.26 | 8.05 ± 2.13 | 58.3 ± 9.9 | 60.9 ± 8.2 |

As is evident from the results in Table 40, in the case of allowing rats to ingest the branched α-glucan of the present invention, with different weight-average molecular weight, the weights of lipids in internal organs and in serum were lowered in any one of the test groups in comparison with those of control group. From the results, it was revealed that the branched α-glucan of the present invention inhibits the increase of the weights of lipids in internal organs and in serum. Comparing the degree of the inhibitory effect among the branched α-glucan with different weight-average molecular weight, the inhibitory effect is significant in the case of using the branched α-glucans with the molecular weights in the range of 2,670 to 44,151, and is more significant in the cases of using the branched α-glucans with the molecular weights in the range of 2,670 to 25,618.

From the results in Experiments 19-2 to 19-5, it was revealed that the branched α-glucan of the present invention has low-cariogenic and low-digestible characteristics and can be advantageously used as a low-calorie WSDF. Further, from the results in Experiments 20 to 22, it was revealed that the branched α-glucan of the present invention can be used as agents for inhibiting the elevation of blood-sugar level and for lowering the lipids in living bodies.

The following Examples 1 and 2 explain the process for producing the α-glucosyltransferase of the present invention. Examples 3 to 6 explain the process for producing the branched α-glucan of the present invention. Example 7 explains physicochemical properties of the branched α-glucan of the present invention. Example 8 explains a quality-improving agent containing the α-glucosyltransferase of the present invention. Further, Examples 9 to 22 explain compositions prepared by incorporating the branched α-glucan of the present invention.

Example 1

According to the method in Experiment 5, *Bacillus circulans* PP710 (FERN BP-10771) was cultivated using a fermenter for about 24 hours. After completion of the cultivation, the culture supernatant was collected by centrifuging culture broth and admixed with ammonium sulfate to give a 80% saturation and allowed to stand at 4° C. for 24 hours. The resulting precipitate was collected by centrifugation and dissolved in 20 mM acetate buffer, pH 6.0. Then, the solution was dialyzed against the same buffer and concentrated using a membrane to make into a concentrated crude enzyme solution. The α-glucosyltransferase activity of the concentrated crude enzyme solution was 200 units/ml. The concentrated crude enzyme solution also contained about 25 units/ml of amylase activity. The crude enzyme solution can be advantageously used for producing the branched α-glucan of the present invention from amylaceous substrates and used as a quality-improving agent for amylaceous substances in foods and beverages.

Example 2

According to the method in Experiment 8, *Arthrobacter globiformis* PP349 (FERM BP-10770) was cultivated using a fermenter for about 24 hours. After completion of the cultivation, culture supernatant was collected by centrifuging culture broth and admixed with ammonium sulfate to give a 80% saturation and stand at 4° C. for 24 hours. The resulting precipitate was collected by centrifugation and dissolved in 20 mM acetate buffer, pH 6.0. Then, the solution was dialyzed against the same buffer and concentrated using a membrane to make into a concentrated crude enzyme solution. The α-glucosyltransferase activity of the concentrated crude enzyme solution was 50 units/ml. The crude enzyme solution can be advantageously used for producing the branched α-glucan of the present invention from amylaceous substrates and used as a quality-improving agent for amylaceous substances in foods and beverages.

Example 3

"PINEDEX® #100", a partial starch hydrolyzate commercialized by Matsutani Chemical Industries Co., Ltd., Hyogo, Japan, was dissolved in water to give a concentration of 30% (w/w) and the pH of the solution was adjusted to 6.0. The concentrated crude enzyme solution, obtained by the method in Example 1, was admixed with the above solution to give an α-glucosyltransferase activity of 10 units/g-dry solid of substrate, and followed by the enzyme reaction at 40° C. for 48 hours. After completion of the reaction, the reaction mixture was heated at 95° C. for 10 minutes, cooled, and then filtrated.

According to the conventional methods, the resulting filtrate was decolored using activated charcoal, deionized using H- and OH-form ion-exchanger resins, and concentrated to obtain the branched α-glucan solution with a concentration of 50% (w/w). On the methylation analysis of the branched α-glucan, a ratio of 2,3,6-trimethylated product and 2,3,4-trimethylated product was 1:1.3, and the total content of 2,3,6-trimethylated product and 2,3,4-trimethylated product was 70.3% in the partially methylated products. Further, contents of 2,4,6-trimethylated product and 2,4-dimethylated product were 3.0% and 4.8%, respectively, in the partially methylated products. The weight-average molecular weight of the branched α-glucan was 6,220 daltons and the value of dividing the weight-average molecular weight with the number average molecular weight (Mw/Mn) was 2.2. In addition, 35.1% (w/w) of isomaltose, on a dry solid basis of hydrolyzate, was formed from the branched α-glucan by isomaltodextranase digestion. The WSDF content of the branched α-glucan was 75.8% (w/w) by Enzyme-HPLC method. Since the product has a non-cariogenicity, hardly digestible property, and adequate viscosity, it can be advantageously used in various compositions such as foods and beverages, cosmetics, and pharmaceuticals as a WSDF, substitute of fat for foods, foods and beverages for diet, quality-improving agent, stabilizer, excipient, thickener, and filler.

Example 4

A tapioca starch was prepared into a 30% (w/v) starch suspension, admixed with calcium carbonate to give a concentration of 0.1% (w/w), adjusted to pH 6.5, and admixed with 0.2%/g-starch of "THERMAMYL™ 60 L", an α-amylase commercialized by Novo Industries A/S, Copenhagen, Denmark, and then incubated at 95° C. for 15 min. After autoclaving at 120° C. for 10 min, the reaction mixture was cooled to about 40° C. The liquefied starch solution was admixed with 10 units/g-dry solid starch of the concentrated crude enzyme solution containing α-glucosyltransferase, prepared by the method in Example 2, and one unit/g-dry solid starch of CGTase from *Bacillus stearothermophilus*, commercialized by Hayashibara Biochemical Laboratories Inc., Okayama, Japan, and followed by the enzymatic reaction at pH 6.0 and 40° C. for 72 hours. After heating the reaction mixture at 95° C. for 10 minutes, it was cooled and filtrated. According to the conventional methods, the resulting filtrate was decolored using activated charcoal, deionized using H- and OH-form ion-exchanger resins, concentrated, and spray-dried to obtain the powdery branched α-glucan. On the methylation analysis of the branched α-glucan, a ratio of 2,3,6-trimethylated product and 2,3,4-trimethylated product was 1:1.6, and the total content of 2,3,6-trimethylated product and 2,3,4-trimethylated product was 80.0% in the partially methylated products. Further, contents of 2,4,6-trimethylated product and 2,4-dimethylated product were 1.4% and 1.7%, respectively, in the partially methylated products. The weight-average molecular weight of the branched α-glucan was 10,330 daltons and the value of dividing the weight-average molecular weight with the number average molecular weight (Mw/Mn) was 2.9. In addition, 40.7% (w/w) of isomaltose, on a dry solid basis of hydrolyzate, was formed from the branched α-glucan by isomaltodextranase digestion. The WSDF content of the branched α-glucan was 68.6% (w/w) by Enzyme-HPLC method. Since the branched α-glucan has a non-cariogenicity, hardly digestible property, and adequate viscosity, it can be advantageously used in various compositions such as foods and beverages, cosmetics, and pharmaceuticals as a WSDF, substitute of fat for foods, foods and beverages for diet, quality-improving agent, stabilizer, excipient, thickener, and filler.

Example 5

To 27.1% (w/w) of liquefied corn starch (hydrolysis: 3.6%), sodium bisulfite and calcium chloride were added to give final concentrations of 0.3% (w/w) and 1 mM, respectively. Then the solution was cooled to 50° C. and admixed with 11.1 units/g-solid of the concentrated crude enzyme solution, prepared by the method in Example 1, and followed by the enzyme reaction at pH 6.0 and 50° C. for 68 hours. After heating the reaction mixture at 80° C. for 60 minutes, it was cooled and filtrated. According to the conventional methods, the resulting filtrate was decolored using activated charcoal, deionized using H- and OH-form ion-exchanger resins, concentrated, and spray-dried to obtain the powdery branched α-glucan. On the methylation analysis of the branched α-glucan, a ratio of 2,3,6-trimethylated product and 2,3,4-trimethylated product was 1:2.5, and the total content of 2,3,6-trimethylated product and 2,3,4-trimethylated product was 68.4% in the partially methylated products. Further, contents of 2,4,6-trimethylated product and 2,4-dimethylated product were 2.6% and 6.8%, respectively, in the partially methylated products. The weight-average molecular weight of the branched α-glucan was 4,097 daltons and the value of dividing the weight-average molecular weight with the number average molecular weight (Mw/Mn) was 2.1. In addition, 35.6% (w/w) of isomaltose, on a dry solid basis of hydrolyzate, was formed from the branched α-glucan by isomaltodextranase digestion. The WSDF content of the branched α-glucan was 79.4% (w/w) by Enzyme-HPLC method. Since the branched α-glucan has a non-cariogenicity, hardly digestible property, and adequate viscosity, it can be advantageously used in various compositions such as foods and beverages, cosmetics, and pharmaceuticals as a WSDF, substitute of fat for foods, foods and beverages for diet, quality-improving agent, stabilizer, excipient, thickener, and filler.

Example 6

Except for using the purified α-glucosyltransferase from *Bacillus circulans* PP710, FERM BP-10771, prepared by the method in Experiment 6, instead of the concentrated crude enzyme preparation, and using 1,000 units/g-solid of isoamylase from *Pseudomonas amyloderamosa*, commercialized by Hayashibara Biochemical Laboratories Inc., Okayama, Japan; the powdery branched α-glucan was obtained according to the method in Example 5. On the methylation analysis of the branched α-glucan, a ratio of 2,3,6-trimethylated product and 2,3,4-trimethylated product was 1:4, and the total content of 2,3,6-trimethylated product and 2,3,4-trimethylated product was 67.9% in the partially methylated products. Further, contents of 2,4,6-trimethylated product and 2,4-dimethylated product were 2.3% and 5.3%, respectively, in the partially methylated products. The weight-average molecular weight of the branched α-glucan was 2,979 daltons and the value of dividing the weight-average molecular weight with the number average molecular weight (Mw/Mn) was 2.0. In addition, 40.6% (w/w) of isomaltose, on a dry solid basis of hydrolyzate, was formed from the branched α-glucan by isomaltodextranase digestion. The WSDF content of the branched α-glucan was 77% (w/w) by Enzyme-HPLC method. Since the branched α-glucan has a non-cariogenicity, hardly digestible property, and adequate viscosity, it can be advantageously used in various compositions such as foods and beverages, cosmetics, and pharmaceuticals as a WSDF, substitute of fat for foods, foods and beverages for diet, quality-improving agent, stabilizer, excipient, thickener, and filler.

Example 7

According to the conventional methods, physicochemical properties of the branched α-glucan prepared in Example 5 were investigated and the results are summarized in Table 41 as an example of properties of the branched α-glucan of the present invention.

TABLE 41

| Aspect | Tasteless and odorless white amorphous powder |
|---|---|
| Solubility | Not soluble in alcohol, acetone, hexane, benzene, ethyl-acetate, carbon tetrachloride, chloroform, and ether. Soluble in water, formamide, and dimethyl sulfoxide |
| pH of aqueous solution | Slightly acidic |
| Component sugar | Glucose only |
| Specific optical rotation | +194.1° to +194.4° (Concentration, 20° C.) |
| Color reaction | Positive: Anthrone-sulfate reaction, Phenol-sulfate reaction Negative: Biuret reaction, Lowry-Foline reaction, Elson-Morgan reaction |
| Melting point | Not showing clear melting point |
| Methylation analysis | Showing the presence of glucose residues involving non-reducing end, 1,3-linkage, 1,4-linkage, 1,6-linkage, 1,3,6-linkage, and 1,4,6-linkage |
| Infrared resonance spectrum | Showing a characteristic absorption to α-anomer of D-glucose around 844 $cm^{-1}$ |
| C-NMR spectrum | Showing a characteristic signal to α-1,6 linkage around 68 ppm |
| Enzymatic digestibility | Forming isomaltose by dextranase treatment |

Example 8

Quality-Improving Agent

Four hundred parts by weight of "FINETOSE®", an anhydrous maltose commercialized by Hayashibara Shoji Inc., Okayama, Japan, 200 parts by weight of "TREHA®", trehalose commercialized by Hayashibara Shoji Inc., Okayama, Japan, and two parts by weight of purified α-glucosyltransferase solution, prepared from *Bacillus circulans* PP710 (FERM BP-10771) by the method in Example 6, were mixed to homogeneity and dried by conventional circulation drying to make into an enzyme preparation comprising α-glucosyltransferase. The product can be used for modifying amylaceous substances and inhibiting the retrogradation of starch by incorporating into amylaceous substances for producing foods and beverages. Therefore, it can be advantageously used as a quality-improving agent, particularly, as a starch-retrogradation inhibiting agent.

Example 9

"Mochi" (Rice Cake)

Five hundred parts by weight of "shiratamako" (rice flour) and 500 parts by weight of "joshinko" (rice flour) were mixed to homogeneity, then, 700 parts by weight of water was admixed with the mixture and steamed with vapor for 40 minutes. Successively, the steamed rice flour was kneaded into dough using "ACM20LVW", a mixer commercialized by Aicoh, Saitama, Japan. After cooling the dough to about 55° C., 360 parts by weight of sucrose and 240 parts by weight of "TREHA®", trehalose commercialized by Hayashibara Shoji Inc., Okayama, Japan, were admixed with the dough. Then, the α-glucosyltransferase of the present invention, purified by the method in Experiment 6, was admixed with the above mixture to give a final enzyme activity of 50 units/g-starchy substance by dividing to four times. Successively, the mixture was further kneaded for three minutes, and then shaped by filling the dough into a plastic container with the internal diameter of 60 mm and the height of 22 mm, and cooled and preserved. The product is a "mochi" (rice cake) with a high quality, soft texture, and extendibility because amylaceous substance in the dough is converted into branched α-glucan by the action of α-glucosyltransferase and it inhibits the retrogradation of starch.

Example 10

"Ohagi" (Rice Dumpling Covered with Bean Jam)

Three hundred-fifty parts by weight of "SUNMALT®", maltose commercialized by Hayashibara Shoji Inc., Okayama, Japan, and 150 parts by weight of "TREHA®", trehalose commercialized by Hayashibara Shoji Inc., Okayama, Japan, were dissolved into hot water to make into a saccharide solution with a concentration of 70% (w/w), and then kept at a temperature of 55° C. Successively, 1,000 parts by weight of glutinous rice, which had been soaked in water, was steamed by the conventional method using a steamer, and then cooled to 55° C. To the steamed glutinous rice, 500 parts by weight of the above saccharide solution and 25 units/g-starchy substance of the α-glucosyltransferase of the present invention, purified by the method in Experiment 9, were admixed and stirred to homogeneity. After keeping the mixture at 45 to 50° C. for about one hour in a heated container, it was made into "ohagi" (rice dumpling covered with bean jam) using bean jam. The product is "ohagi" with a high quality, which keeps soft texture just after preparation and shows no syneresis when thawed after refrigeration or freezing, because gelatinized starch is converted into branched α-glucan by the action of α-glucosyltransferase and it inhibits the retrogradation of starch.

Example 11

Sweetened Condensed Milk

Two parts by weight of the branched α-glucan, obtained by the method in Example 3, and three parts by weight of sucrose were dissolved in 100 parts by weight of material milk. The resulting mixture was sterilized by heating with a plate heater, concentrated to give a concentration of 70%, and then packed in a can under a sterile condition to make into a product. Since the product has a mild sweetness and good flavor, it can be advantageously used as a sweetened condensed milk rich in WSDF for seasoning fruits, coffee, cocoa, black tea, and the like.

Example 12

Lactic Acid Bacteria Beverage

One hundred seventy-five parts by weight of skim milk, 50 parts by weight of the powdery branched α-glucan, obtained by the method in Example 4, and 50 parts by weight of "NYUKA-OLIGO®", a lactosucrose high content powder commercialized by Hayashibara Shoji Inc., Okayama, Japan, were dissolved into 1,500 parts by weight of water, and then the resulting mixture was sterilized at 65° C. for 30 min. After cooling the mixture to 40° C., 30 parts by weight of a lactic acid bacterium was inoculated to the mixture as a starter according to conventional method, and cultured at 37° C. for eight hours to obtain a lactic acid bacteria beverage. The product has a satisfactory flavor and keeps the lactic acid bacterium stably because it comprises branched α-glucan as a WSDF and oligosaccharide. Further, the product is preferably used as a lactic acid bacteria beverage having a growth-promoting activity for bifidobacteria and a function-regulating activity for intestine.

Example 13

Powdery Juice

To 33 parts by weight of a powdery orange juice, produced by a spray-drying method, 10 parts by weight of a powdery branched α-glucan, obtained by the method in Example 4, 20 parts by weight of hydrous crystalline trehalose, 20 parts by weight of anhydrous crystalline maltitol, 0.65 part by weight of anhydrous citric acid, 0.1 part by weight of malic acid, 0.2 part by weight of 2-O-α-glucosyl-L-ascorbic acid, 0.1 part by weight of sodium citrate, 0.5 part by weight of pullulan, and suitable amount of powdery flavor were mixed with stirring and the resulting powdery mixture was pulverized to make into a fine powdery product. Then, the powdery product was subjected to a fluidized bed granulator and its exhaust temperature was set to 40° C. A suitable amount of a solution comprising branched α-glucan, obtained by the method in Example 2, was sprayed as a binder on the powdery product and granulated for 30 min and the resulting product was weighted and packed to make into a product. The product is a powdery juice with a fruit-juice content of about 30%. Since the product shows no strange taste and smell, it has a high quality and commercial value as a low-calorie juice rich in WSDF.

Example 14

Custard Cream

One hundred parts by weight of corn starch, 30 parts by weight of the solution comprising branched α-glucan, obtained by the method in Example 3, 70 parts by weight of hydrous crystalline trehalose, 40 parts by weight of sucrose, and one part by weight of sodium chloride were mixed well, and then 280 parts by weight of whole egg was further admixed with the mixture. Successively, 1,000 parts by weight of boiled milk was gradually admixed with the resulting mixture and the resulting solution was continuously stirred on an open flame. The heating was stopped at the point that corn starch was completely gelatinized to give a transparency. After cooling the mixture, a suitable amount of vanilla essence was admixed with the mixture, weighted, and packed to make into a custard cream product. The product is a high quality custard cream with a satisfactory gloss and flavor and rich in WSDF.

Example 15

"Ann" (Sweetened Bean Jam)

According to the conventional method, 10 parts by weight of material adzuki bean was boiled in water, and removing astringents, lixivium, and water-soluble contaminant, and made into about 21 parts by weight of adzuki "ann" (bean jam). Then, 14 parts by weight of sucrose, 5 parts by weight of a solution comprising branched α-glucan, obtained by the method in Example 3, and four parts by weight of water were admixed with the above bean jam and boiled. After adding a small amount of salad oil, the bean jam was kneaded without crushing bean to make into about 35 parts by weight of product. Since the product is stable bean jam without color-deterioration and syneresis and rich in branched α-glucan as a WSDF, it can be preferably used as confectionery material such as bun filled with bean jam, bean jam cake, ice milk and the like.

Example 16

Bread

One hundred parts by weight of wheat flour, two parts by weight of yeast, five parts by weight of sucrose, 1 part by weight of the branched α-glucan obtained by the method in Example 4, 0.1 parts by weight of inorganic salts and water were mixed and kneaded by the conventional method. Then, the resulting dough was fermented at 26° C. for two hours, further fermented for 30 minutes, and baked.

The product show satisfactory color, a fluffy bulge, and rich in the branched α-glucan as a WSDF. The product is bread with a high quality showing satisfactory elasticity and mild sweetness.

Example 17

Powdery Peptide Product

To one part by weight of "HI-NUTE S®", 40% soybean peptides solution for foods, commercialized by Fuji Oil Co., Ltd., Osaka, Japan, two parts by weight of the powdery branched α-glucan, obtained by the method in Example 4, was mixed and the resulting mixture was put into a plastic tray, dried at 50° C. under a reduced pressure, and pulverized to make into a powdery peptide product. The product has a satisfactory flavor and is useful as a material for premix, low-calorie confectionaries for ice dessert. Further, the product is useful as a dietary fiber and antiflaturent for a fluid diet for oral- or tube-intake.

Example 18

Cosmetic Cream

According to conventional method, two parts by weight of polyoxyethylenglycol mono-stearate, five parts by weight of self-emulsified glycerin mono-stearate, two parts by weight of the powdery branched α-glucan, obtained by the method in Example 4, one part by weight of "αG-RUTIN", α-glucosyl rutin, commercialized by Hayashibara Inc., Okayama, Japan, one part by weight of liquid paraffin, 10 parts by weight of glycerin-trioctanoate and a suitable amount of preservative were mixed and dissolved by heating. The resulting mixture was further admixed with two parts by weight of L-lactic acid, five parts by weight of 1,3-butylen glycol, and 66 parts by weight of purified water, and the resulting mixture was emulsified using a homogenizer. The homogenized mixture was further admixed with a suitable amount of flavor and stirred to make into a cosmetic cream. The product has a satisfactory moisture-retaining property because it comprises the branched α-glucan. The product has a satisfactory stability and can be advantageously used as a sunburn preventive, skin-care agent and whitening agent for skin.

Example 19

Toothpaste

Forty-five parts by weight of calcium monohydrogen phosphate, 1.5 parts by weight of sodium lauryl sulfate, 25 parts by weight of glycerin, 0.5 part by weight of polyoxyethylene sorbitan laurate, 15 parts by weight of the solution comprising branched α-glucan, obtained by the method in Example 3, 0.02 part by weight of saccharin, and 18 parts by weight of water were mixed to make into a toothpaste. The product is toothpaste which shows a satisfactory availability without losing the washing property of surfactant.

Example 20

Solid Agent for a Fluid Diet

One hundred parts by weight of the powdery branched α-glucan, obtained by the method in Example 4, 200 parts by weight of hydrous crystalline trehalose, 200 parts by weight of a maltotetraose high content powder, 270 parts by weight of powdery egg yolk, 209 parts by weight of skim milk, 4.4 parts by weight of sodium chloride, 1.8 parts by weight of potassium chloride, four parts by weight of magnesium sulfate, 0.01 part by weight of thiamine, 0.1 part by weight of sodium L-ascorbate, 0.6 parts by weight of vitamin E acetate, and 0.04 part by weight of nicotinic acid-amide were mixed to make into a composition. Twenty-five grams each of the composition was packed into a dampproof laminate pouch, and the pouch was heat-sealed to make into a product. The product contains WSDF, and can be advantageously used for supplying energy to living bodies as a fluid diet to regulate the function of intestine by taking orally or through tube into nasal cavity, stomach, and intestine.

Example 21

Tablet

To 50 parts by weight of aspirin, 14 parts by weight of powdery hydrous crystalline trehalose and four parts by weight of the powdery branched α-glucan, obtained by the method in Example 4, were admixed to homogeneity. According to the conventional method, the resulting mixture was made into tablet with 680 mg/tablet and thickness of 5.25 mm using a tableting machine. The product was made by using the hardly digestive glucan and trehalose as excipients. The product shows no hygroscopicity and satisfactory physical strength but easily disrupted in water. Further, since the branched α-glucan acts as WSDF, the tablet can be used for regulating the functions of the intestine.

Example 22

Ointment for Curing Wound

To 400 parts by weight of maltose, 50 parts by weight of a methanol solution containing three parts by weight of iodine and 200 parts by weight of 10% (w/v) aqueous solution containing the powdery branched α-glucan, obtained by the method in Example 4, were mixed to make into an ointment for curing wound with an adequate extendibility and adhesive property. The product shows an adequate viscosity and moisture-retaining property, and is an ointment with a high marketability and less change over time. Since iodine in the product has an antimicrobial activity and maltose in the product acts as an energy-supplement for cells, the curing period is shortened and wound surface is cured completely.

INDUSTRIAL APPLICABILITY

Since the branched α-glucan of the present invention shows a high safety and almost equal digestibility with a commercially available low-digestible dextrin, it can be advantageously used as WSDF. Further, since the branched α-glucan of the present invention exhibits effects of inhibiting the increase of blood-sugar level and lowering lipids in living bodies, it is useful as a health food. According to the present invention, the branched α-glucan, having almost equal digestibility with the low-digestible dextrin which has been produced from starch by chemical reaction or complicated and inefficient method, can be produced efficiently in a large scale by the enzymatic reaction. The present invention, providing the low-digestible branched α-glucan and the process for producing it, is a significantly important invention that greatly contributes to various fields such as food and beverages, cosmetics, and pharmaceuticals.

The invention claimed is:

1. A process for producing a saccharide composition comprising branched α-glucan, comprising the steps of:
    allowing an α-glucosyltransferase and cyclomaltodextrin glucanotransferase to act on maltose and/or α-1,4 glucan having a glucose polymerization degree of 3 or higher; and
    collecting the formed saccharide composition comprising branched α-glucan;
    said saccharide composition is characterized in that the content of water-soluble dietary fiber of the saccharide composition, obtained by applying a high performance liquid chromatography method (Enzyme-HPLC method), is 40% (w/w) or higher.

2. The process of claim 1, wherein said saccharide composition has the following characteristics upon methylation analysis:
    (1) Ratio of 2,3,6-trimethyl-1,4,5-triacetyl-glucitol to 2,3,4-trimethyl-1,5,6-triacetyl-glucitol, which indicates the ratio of glucose residues with α-1,4 linkages to glucose residues with α-1,6 linkages, is in the range of 1:0.6 to 1:4; and
    (2) Total content of 2,3,6-trimethyl-1,4,5-triacetyl-glucitol and 2,3,4-trimethyl-1,5,6-triacetyl-glucitol, which indicates that the total content of glucose residues with α-1,4 linkages and glucose residues with α-1,6 linkages, is 60% or higher in the partially methylated glucitol acetates.

3. The process of claim 2, wherein said saccharide composition has the following characteristics upon methylation analysis:
    (3) Content of 2,4,6-trimethyl-1,3,5-triacetyl-glucitol, which indicates that the content of glucose residues with α-1,3 linkage, is 0.5% or higher but less than 10% in the partially methylated glucitol acetates; and
    (4) Content of 2,4-dimethyl-1,3,5,6-tetraacetyl-glucitol, which indicates that the content of glucose residues with both α-1,3 and α-1,6 linkages, is 0.5% or higher in the partially methylated glucitol acetates.

4. The process of claim 1, wherein said saccharide composition is characterized in that it forms isomaltose in an amount of 25% (w/w) or higher but 50% (w/w) or lower, on a dry solid basis, when the saccharide composition is digested by isomaltodextranase (EC 3.2.1.94).

5. The process of claim 1, wherein said α-glucosyltransferase, which has the following physicochemical properties:
  (1) Molecular weight
    90,000±10,000 daltons on SDS-polyacrylamide gel electrophoresis;
  (2) Optimum temperature
    50 to 55° C. when reacted at pH 6.0 for 30 min;
  (3) Optimum pH
    pH 5.0 to 6.3 when reacted at 40° C. for 30 min;
  (4) Thermal stability
    Stable up to the temperature of 40° C. when incubated at pH 6.0 for 60 min; and
  (5) pH Stability
Stable at least in the range of pH 4.0 to 8.0 when incubated at 4° C. for 24 hours.

\* \* \* \* \*